United States Patent [19]
Darnell, Jr. et al.

[11] Patent Number: 5,976,835
[45] Date of Patent: Nov. 2, 1999

[54] NUCLEIC ACIDS ENCODING RECEPTOR RECOGNITION FACTOR STAT1α AND STAT1β, AND METHODS OF USE THEREOF

[75] Inventors: James E. Darnell, Jr., Larchmont; Christian W. Schindler, New York; Xin-Yuan Fu, Forrest Hills; Zilong Wen; Zhong Zhong, both of New York, all of N.Y.

[73] Assignee: The Rockefeller University, New York, N.Y.

[21] Appl. No.: 08/820,754

[22] Filed: Mar. 19, 1997

Related U.S. Application Data

[60] Division of application No. 08/212,185, Mar. 11, 1994, which is a continuation-in-part of application No. 08/126,588, Sep. 24, 1993, abandoned, and application No. 08/126,595, Sep. 24, 1993, abandoned, each is a continuation-in-part of application No.07/980,498, Nov. 23, 1992, abandoned, which is a continuation-in-part of application No. 07/854,296, Mar. 19, 1992, abandoned.

[51] Int. Cl.$^6$ .......................... C07H 21/00; C12N 15/12
[52] U.S. Cl. ................. 435/69.1; 435/172.3; 435/325; 435/252.3; 435/320.1; 530/350; 530/358; 536/23.5; 536/24.3; 935/8; 935/9
[58] Field of Search ................ 536/23.5, 24.3; 435/69.1, 172.3, 325, 252.3, 320.1; 530/350, 358; 935/8, 9

[56] References Cited

U.S. PATENT DOCUMENTS

| | | | |
|---|---|---|---|
| 5,534,409 | 7/1996 | Groner et al. ......................... | 435/6 |
| 5,618,693 | 4/1997 | McKnight et al. .................... | 435/69.1 |
| 5,639,858 | 6/1997 | Hoey et al. ........................... | 530/350 |

FOREIGN PATENT DOCUMENTS

WO 96/29341  9/1996  WIPO.

*Primary Examiner*—Lorraine Spector
*Attorney, Agent, or Firm*—Klauber & Jackson

[57] ABSTRACT

Receptor recognition factors exist that recognizes the specific cell receptor to which a specific ligand has been bound, and that may thereby signal and/or initiate the binding of the transcription factor to the DNA site. The receptor recognition factor is in one instance, a part of a transcription factor, and also may interact with other transcription factors to cause them to activate and travel to the nucleus for DNA binding. The receptor recognition factor appears to be second-messenger-independent in its activity, as overt perturbations in second messenger concentrations are of no effect. The concept of the invention is illustrated by the results of studies conducted with interferon (IFN)-stimulated gene transcription, and particularly, the activation caused by both IFNα and IFN-γ. Specific DNA and amino acid sequences for various human and murine receptor recognition factors are provided, as are polypeptide fragments of two of the ISGF-3 genes, and antibodies have also been prepared and tested. The polypeptides confirm direct involvement of tyrosine kinase in intracellular message transmission. Numerous diagnostic and therapeutic materials and utilities are also disclosed.

36 Claims, 46 Drawing Sheets

FIG.1A

```
                                            1
                                          met ala gln trp glu met leu gln
ACTGCAACCCTAATCAGAGCCCAA                  ATG GCG CAG TGG GAA ATG CTG CAG 10                                                      20
asn leu asp ser pro phe gln asp gln leu his gln leu tyr ser
AAT CTT GAC AGC CCC TTT CAG GAT CAG CTG CAC CAG CTT TAC TCG 30
his ser leu leu pro val asp ile arg gln tyr leu ala val trp
CAC AGC CTC CTG CCT GTG GAC ATT CGA CAG TAC TTG GCT GTC TGG 40                                            50
ile glu asp gln asn trp gln glu ala ala leu gly ser asp asp
ATT GAA GAC CAG AAC TGG CAG GAA GCT GCA CTT GGG AGT GAT GAT 60
ser lys ala thr met leu phe phe his phe leu asp gln leu asn
TCC AAG GCT ACC ATG CTA TTC TTC CAC TTC TTG GAT CAG CTG AAC 70                                                 80
tyr glu cys gly arg cys ser gln asp pro glu ser leu leu leu
TAT GAG TGT GGC CGT TGC AGC CAG GAC CCA GAG TCC TTG TTG CTG 90
gln his asn leu arg lys phe cys arg asp ile gln pro phe ser
CAG CAC AAT TTG CGG AAA TTC TGC CGG GAC ATT CAG CCC TTT TCC 100                                              110
gln asp pro thr gln leu ala glu met ile phe asn leu leu leu
CAG GAT CCT ACC CAG TTG GCT GAG ATG ATC TTT AAC CTC CTT CTG 120
glu glu lys arg ile leu ile gln ala gln arg ala gln leu glu
GAA GAA AAA AGA ATT TTG ATC CAG GCT CAG AGG GCC CAA TTG GAA 130                                              140
gln gly glu pro val leu glu thr pro val glu ser gln gln his
CAA GGA GAG CCA GTT CTC GAA ACA CCT GTG GAG AGC CAG CAA CAT 150
glu ile glu ser arg ile leu asp leu arg ala met met glu lys
GAG ATT GAA TCC CGG ATC CTG GAT TTA AGG GCT ATG ATG GAG AAG 160                                              170
leu val lys ser ile ser gln leu lys asp gln gln asp val phe
CTG GTA AAA TCC ATC AGC CAA CTG AAA GAC CAG CAG GAT GTC TTC

180
```

Session Name: rb    FIG. 1B

```
cys phe arg tyr lys ile gln ala lys gly lys thr pro ser leu
TGC TTC CGA TAT AAG ATC CAG GCC AAA GGG AAG ACA CCC TCT CTG 190                                     200
asp pro his gln thr lys glu gln lys ile leu gln glu thr leu
GAC CCC CAT CAG ACC AAA GAG CAG AAG ATT CTG CAG GAA ACT CTC 210
asn glu leu asp lys arg arg lys glu val leu asp ala ser lys
AAT GAA CTG GAC AAA AGG AGA AAG GAG GTG CTG GAT GCC TCC AAA 220                                     230
ala leu leu gly arg leu thr thr leu ile glu leu leu leu pro
GCA CTG CTA GGC CGA TTA ACT ACC CTA ATC GAG CTA CTG CTG CCA 240
lys leu glu glu trp lys ala gln gln gln lys ala cys ile arg
AAG TTG GAG GAG TGG AAG GCC CAG CAG CAA AAA GCC TGC ATC AGA 250                                     260
ala pro ile asp his gly leu glu gln leu glu thr trp phe thr
GCT CCC ATT GAC CAC GGG TTG GAA CAG CTG GAG ACA TGG TTC ACA 270
ala gly ala lys leu leu phe his leu arg gln leu leu lys glu
GCT GGA GCA AAG CTG TTG TTT CAC CTG AGG CAG CTG CTG AAG GAG 280                                     290
leu lys gly leu ser cys leu val ser tyr gln asp asp pro leu
CTG AAG GGA CTG AGT TGC CTG GTT AGC TAT CAG GAT GAC CCT CTG 300
thr lys gly val asp leu arg asn ala gln val thr glu leu leu
ACC AAA GGG GTG GAC CTA CGC AAC GCC CAG GTC ACA GAG TTG CTA 310                                     320
gln arg leu leu his arg ala phe val val glu thr gln pro cys
CAG CGT CTG CTC CAC AGA GCC TTT GTG GTA GAA ACC CAG CCC TGC 330
met pro gln thr pro his arg pro leu ile leu lys thr gly ser
ATG CCC CAA ACT CCC CAT CGA CCC CTC ATC CTC AAG ACT GGC AGC 340                                     350
lys phe thr val arg thr arg leu leu val arg leu gln glu gly
AAG TTC ACC GTC CGA ACA AGG CTG CTG GTG AGA CTC CAG GAA GGC 360
asn glu ser leu thr val glu val ser ile asp arg asn pro pro
AAT GAG TCA CTG ACT GTG GAA GTC TCC ATT GAC AGG AAT CCT CCT 370                                     380
gln leu gln gly phe arg lys phe asn ile leu thr ser asn gln
CAA TTA CAA GGC TTC CGG AAG TTC AAC ATT CTG ACT TCA AAC CAG 390
lys thr leu thr pro glu lys gly gln ser gln gly leu ile trp
```

FIG. 1C

Session Name: rb

```
AAA ACT TTG ACC CCC GAG AAG GGG CAG AGT CAG GGT TTG ATT TGG
        400                                 410
asp phe gly tyr leu thr leu val glu gln arg ser gly gly ser
GAC TTT GGT TAC CTG ACT CTG GTG GAG CAA CGT TCA GGT GGT TCA
                            420
gly lys gly ser asn lys gly pro leu gly val thr glu glu leu
GGA AAG GGC AGC AAT AAG GGG CCA CTA GGT GTG ACA GAG GAA CTG
        430                                 440
his ile ile ser phe thr val lys tyr thr tyr gln gly leu lys
CAC ATC ATC AGC TTC ACG GTC AAA TAT ACC TAC CAG GGT CTG AAG
                            450
gln glu leu lys thr asp thr leu pro val val ile ile ser asn
CAG GAG CTG AAA ACG GAC ACC CTC CCT GTG GTG ATT ATT TCC AAC
        460                                 470
met asn gln leu ser ile ala trp ala ser val leu trp phe asn
ATG AAC CAG CTC TCA ATT GCC TGG GCT TCA GTT CTC TGG TTC AAT
                            480
leu leu ser pro asn leu gln asn gln gln phe phe ser asn pro
TTG CTC AGC CCA AAC CTT CAG AAC CAG CAG TTC TTC TCC AAC CCC
        490                                 500
pro lys ala pro trp ser leu leu gly pro ala leu ser trp gln
CCC AAG GCC CCC TGG AGC TTG CTG GGC CCT GCT CTC AGT TGG CAG
                            510
phe ser ser tyr val gly arg gly leu asn ser asp gln leu ser
TTC TCC TCC TAT GTT GGC CGA GGC CTC AAC TCA GAC CAG CTG AGC
        520                                 530
met leu arg asn lys leu phe gly gln asn cys arg thr glu asp
ATG CTG AGA AAC AAG CTG TTC GGG CAG AAC TGT AGG ACT GAG GAT
                            540
pro leu leu ser trp ala asp phe thr lys arg glu ser pro pro
CCA TTA TTG TCC TGG GCT GAC TTC ACT AAG CGA GAG AGC CCT CCT
        550                                 560
gly lys leu pro phe trp thr trp leu asp lys ile leu glu leu
GGC AAG TTA CCA TTC TGG ACA TGG CTG GAC AAA ATT CTG GAG TTG
                            570
val his asp his leu lys asp leu trp asn asp gly arg ile met
GTA CAT GAC CAC CTG AAG GAT CTC TGG AAT GAT GGA CGC ATC ATG
        580                                 590
gly phe val ser arg ser gln glu arg arg leu leu lys lys thr
GGC TTT GTG AGT CGG AGC CAG GAG CGC CGG CTG CTG AAG AAG ACC
                            600
met ser gly thr phe leu leu arg phe ser glu ser ser glu gly
ATG TCT GGC ACC TTT CTA CTG CGC TTC AGT GAA TCG TCA GAA GGG
```

Session Name: rb

FIG. 1D

```
       610                                              620
gly ile thr cys ser trp val glu his gln asp asp asp lys val
GGC ATT ACC TGC TCC TGG GTG GAG CAC CAG GAT GAT GAC AAG GTG 630
leu ile tyr ser val gln pro tyr thr lys glu val leu gln ser
CTC ATC TAC TCT GTG CAA CCG TAC ACG AAG GAG GTG CTG CAG TCA 640                                              650
leu pro leu thr glu ile ile arg his tyr gln leu leu thr glu
CTC CCG CTG ACT GAA ATC ATC CGC CAT TAC CAG TTG CTC ACT GAG 660
glu asn ile pro glu asn pro leu arg phe leu tyr pro arg ile
GAG AAT ATA CCT GAA AAC CCA CTG CGC TTC CTC TAT CCC CGA ATC 670                                              680
pro arg asp glu ala phe gly cys tyr tyr gln glu lys val asn
CCC CGG GAT GAA GCT TTT GGG TGC TAC TAC CAG GAG AAA GTT AAT 690
leu gln glu arg arg lys tyr leu lys his arg leu ile val val
CTC CAG GAA CGG AGG AAA TAC CTG AAA CAC AGG CTC ATT GTG GTC 700                                              710
ser asn arg gln val asp glu leu gln gln pro leu glu leu lys
TCT AAT AGA CAG GTG GAT GAA CTG CAA CAA CCG CTG GAG CTT AAG 720
pro glu pro glu leu glu ser leu glu leu glu leu gly leu val
CCA GAG CCA GAG CTG GAG TCA TTA GAG CTG GAA CTA GGG CTG GTG 730                                              740
pro glu pro glu leu ser leu asp leu glu pro leu leu lys ala
CCA GAG CCA GAG CTC AGC CTG GAC TTA GAG CCA CTG CTG AAG GCA 750
gly leu asp leu gly pro glu leu glu ser val leu glu ser thr
GGG CTG GAT CTG GGG CCA GAG CTA GAG TCT GTG CTG GAG TCC ACT 760                                              770
leu glu pro val ile glu pro thr leu cys met val ser gln thr
CTG GAG CCT GTG ATA GAG CCC ACA CTA TGC ATG GTA TCA CAA ACA 780
val pro glu pro asp gln gly pro val ser gln pro val pro glu
GTG CCA GAG CCA GAC CAA GGA CCT GTA TCA CAG CCA GTG CCA GAG 790                                              800
pro asp leu pro cys asp leu arg his leu asn thr glu pro met
CCA GAT TTG CCC TGT GAT CTG AGA CAT TTG AAC ACT GAG CCA ATG 810
glu ile phe arg asn cys val lys ile glu glu ile met pro asn
GAA ATC TTC AGA AAC TGT GTA AAG ATT GAA GAA ATC ATG CCG AAT
```

FIG. 1E

Session Name: rb

```
     820                                              830
gly asp pro leu leu ala gly gln asn thr val asp glu val tyr
GGT GAC CCA CTG TTG GCT GGC CAG AAC ACC GTG GAT GAG GTT TAC 840
val ser arg pro ser his phe tyr thr asp gly pro leu met pro
GTC TCC CGC CCC AGC CAC TTC TAC ACT GAT GGA CCC TTG ATG CCT 850 851
ser asp phe AM
TCT GAC TTC TAG GAACCACATTTCCTCTGTTCTTTTCATATCTCTTTGCCCTTCCTA
```

CTCCTCATAGCATGATATTGTTCTCCAAGGATGGGAATCAGGCATGTGTCCCTTCCAAGC

TGTGTTAACTGTTCAAACTCAGGCCTGTGTGACTCCATTGGGGTGAGAGGTGAAAGCATA

ACATGGGTACAGAGGGGACAACAATGAATCAGAACAGATGCTGAGCCATAGGTCTAAATA

GGATCCTGGAGGCTGCCTGCTGTGCTGGGAGGTATAGGGGTCCTGGGGGCAGGCCAGGGC

AGTTGACAGGTACTTGGAGGGCTCAGGGCAGTGGCTTCTTTCCAGTATGGAAGGATTTCA

ACATTTTAATAGTTGGTTAGGCTAAACTGGTGCATACTGGCATTGGCCTTGGTGGGGAGC

ACAGACACAGGATAGGACTCCATTTCTTTCTTCCATTCCTTCATGTCTAGGATAACTTGC

TTTCTTCTTTCCTTTACTCCTGGCTCAAGCCCTGAATTTCTTCTTTTCCTGCAGGGGTTG

AGAGCTTTCTGCCTTAGCCTACCATGTGAAACTCTACCCTGAAGAAAGGGATGGATAGGA

AGTAGACCTCTTTTTCTTACCAGTCTCCTCCCCTACTCTGCCCCCTAAGCTGGCTGTACC

TGTTCCTCCCCCATAAAATGATCCTGCCAATCTAAAAAAAAA

FIG. 2A

```
ATTAAACCTCTCGCCGAGCCCCTCCGCAGACTCTGCGCCGGAAAGTTTCATTTGCTGTATGCC

ATCCTCGAGAGCTGTCTAGGTTAACGTTCGCACTCTGTGTATATAACCTCGACAGTCTTGGCA

CCTAACGTGCTGTGCGTAGCTGCTCCTTTGGTTGAATCCCCAGGCCCTTGTTGGGGCACAAGG
```

```
                   1                                           10
           met ser gln trp tyr glu leu gln gln leu asp ser lys
    TGGCAGG ATG TCT CAG TGG TAC GAA CTT CAG CAG CTT GAC TCA AAA 20
    phe leu glu gln val his gln leu tyr asp asp ser phe pro met
    TTC CTG GAG CAG GTT CAC CAG CTT TAT GAT GAC AGT TTT CCC ATG 30                                          40
    glu ile arg gln tyr leu ala gln trp leu glu lys gln asp trp
    GAA ATC AGA CAG TAC CTG GCA CAG TGG TTA GAA AAG CAA GAC TGG 50
    glu his ala ala asn asp val ser phe ala thr ile arg phe his
    GAG CAC GCT GCC AAT GAT GTT TCA TTT GCC ACC ATC CGT TTT CAT 60                                          70
    asp leu leu ser gln leu asp asp gln tyr ser arg phe ser leu
    GAC CTC CTG TCA CAG CTG GAT GAT CAA TAT AGT CGC TTT TCT TTG 80
    glu asn asn phe leu leu gln his asn ile arg lys ser lys arg
    GAG AAT AAC TTC TTG CTA CAG CAT AAC ATA AGG AAA AGC AAG CGT 90                                         100
    asn leu gln asp asn phe gln glu asp pro ile gln met ser met
    AAT CTT CAG GAT AAT TTT CAG GAA GAC CCA ATC CAG ATG TCT ATG 110
    ile ile tyr ser cys leu lys glu glu arg lys ile leu glu asn
    ATC ATT TAC AGC TGT CTG AAG GAA GAA AGG AAA ATT CTG GAA AAC 120                                         130
    ala gln arg phe asn gln ala gln ser gly asn ile gln ser thr
    GCC CAG AGA TTT AAT CAG GCT CAG TCG GGG AAT ATT CAG AGC ACA 140
    val met leu asp lys gln lys glu leu asp ser lys val arg asn
    GTG ATG TTA GAC AAA CAG AAA GAG CTT GAC AGT AAA GTC AGA AAT 150                                         160
    val lys asp lys val met cys ile glu his glu ile lys ser leu
    GTG AAG GAC AAG GTT ATG TGT ATA GAG CAT GAA ATC AAG AGC CTG 170
    glu asp leu gln asp glu tyr asp phe lys cys lys thr leu gln
    GAA GAT TTA CAA GAT GAA TAT GAC TTC AAA TGC AAA ACC TTG CAG
```

FIG. 2B

```
       180                                                      190
asn arg glu his glu thr asn gly val ala lys ser asp gln lys
AAC AGA GAA CAC GAG ACC AAT GGT GTG GCA AAG AGT GAT CAG AAA 200
gln glu gln leu leu leu lys lys met tyr leu met leu asp asn
CAA GAA CAG CTG TTA CTC AAG AAG ATG TAT TTA ATG CTT GAC AAT 210                                        220
lys arg lys glu val val his lys ile ile glu leu leu asn val
AAG AGA AAG GAA GTA GTT CAC AAA ATA ATA GAG TTG CTG AAT GTC 230
thr glu leu thr gln asn ala leu ile asn asp glu leu val glu
ACT GAA CTT ACC CAG AAT GCC CTG ATT AAT GAT GAA CTA GTG GAG 240                                             250
trp lys arg arg gln gln ser ala cys ile gly gly pro pro asn
TGG AAG CGG AGA CAG CAG AGC GCC TGT ATT GGG GGG CCG CCC AAT 260
ala cys leu asp gln leu gln gln val arg gln gln leu lys lys
GCT TGC TTG GAT CAG CTG CAG CAA GTT CGG CAG CAG CTT AAA AAG 270                                             280
leu glu glu leu glu gln lys tyr thr tyr glu his asp pro ile
TTG GAG GAA TTG GAA CAG AAA TAC ACC TAC GAA CAT GAC CCT ATC 290
thr lys asn lys gln val leu trp asp arg thr phe ser leu phe
ACA AAA AAC AAA CAA GTG TTA TGG GAC CGC ACC TTC AGT CTT TTC 300                                             310
gln gln leu ile gln ser ser phe val val glu arg gln pro cys
CAG CAG CTC ATT CAG AGC TCG TTT GTG GTG GAA AGA CAG CCC TGC 320
met pro thr his pro gln arg pro leu val leu lys thr gly val
ATG CCA ACG CAC CCT CAG AGG CCG CTG GTC TTG AAG ACA GGG GTC 330                                             340
gln phe thr val lys leu arg leu leu val lys leu gln glu leu
CAG TTC ACT GTG AAG TTG AGA CTG TTG GTG AAA TTG CAA GAG CTG 350
asn tyr asn leu lys val lys val leu phe asp lys asp val asn
AAT TAT AAT TTG AAA GTC AAA GTC TTA TTT GAT AAA GAT GTG AAT 360                                             370
glu arg asn thr val lys gly phe arg lys phe asn ile leu gly
GAG AGA AAT ACA GTA AAA GGA TTT AGG AAG TTC AAC ATT TTG GGC 380
thr his thr lys val met asn met glu glu ser thr asn gly ser
ACG CAC ACA AAA GTG ATG AAC ATG GAG GAG TCC ACC AAT GGC AGT
```

FIG. 2C

```
       390                                              400
leu ala ala glu phe arg his leu gln leu lys glu gln lys asn
CTG GCG GCT GAA TTT CGG CAC CTG CAA TTG AAA GAA CAG AAA AAT 410
ala gly thr arg thr asn glu gly pro leu ile val thr glu glu
GCT GGC ACC AGA ACG AAT GAG GGT CCT CTC ATC GTT ACT GAA GAG 420                                              430
leu his ser leu ser phe glu thr gln leu cys gln pro gly leu
CTT CAC TCC CTT AGT TTT GAA ACC CAA TTG TGC CAG CCT GGT TTG 440
val ile asp leu glu thr thr ser leu pro val val val ile ser
GTA ATT GAC CTC GAG ACG ACC TCT CTG CCC GTT GTG GTG ATC TCC 450                                              460
asn val ser gln leu pro ser gly trp ala ser ile leu trp tyr
AAC GTC AGC CAG CTC CCG AGC GGT TGG GCC TCC ATC CTT TGG TAC 470
asn met leu val ala glu pro arg asn leu ser phe phe leu thr
AAC ATG CTG GTG GCG GAA CCC AGG AAT CTG TCC TTC TTC CTG ACT 480                                              490
pro pro cys ala arg trp ala gln leu ser glu val leu ser trp
CCA CCA TGT GCA CGA TGG GCT CAG CTT TCA GAA GTG CTG AGT TGG 500
gln phe ser ser val thr lys arg gly leu asn val asp gln leu
CAG TTT TCT TCT GTC ACC AAA AGA GGT CTC AAT GTG GAC CAG CTG 510                                              520
asn met leu gly glu lys leu leu gly pro asn ala ser pro asp
AAC ATG TTG GGA GAG AAG CTT CTT GGT CCT AAC GCC AGC CCC GAT 530
gly leu ile pro trp thr arg phe cys lys glu asn ile asn asp
GGT CTC ATT CCG TGG ACG AGG TTT TGT AAG GAA AAT ATA AAT GAT 540                                              550
lys asn phe pro phe trp leu trp ile glu ser ile leu glu leu
AAA AAT TTT CCC TTC TGG CTT TGG ATT GAA AGC ATC CTA GAA CTC 560
ile lys lys his leu leu pro leu trp asn asp gly cys ile met
ATT AAA AAA CAC CTG CTC CCT CTC TGG AAT GAT GGG TGC ATC ATG 570                                              580
gly phe ile ser lys glu arg glu arg ala leu leu lys asp gln
GGC TTC ATC AGC AAG GAG CGA GAG CGT GCC CTG TTG AAG GAC CAG 590
gln pro gly thr phe leu leu arg phe ser glu ser ser arg glu
CAG CCG GGG ACC TTC CTG CTG CGG TTC AGT GAG AGC TCC CGG GAA 600                                              610
```

FIG. 2D

```
        gly ala ile thr phe thr trp val glu arg ser gln asn gly gly
        GGG GCC ATC ACA TTC ACA TGG GTG GAG CGG TCC CAG AAC GGA GGC
                                    620
        glu pro asp phe his ala val glu pro tyr thr lys lys glu leu
        GAA CCT GAC TTC CAT GCG GTT GAA CCC TAC ACG AAG AAA GAA CTT
            630                                     640
        ser ala val thr phe pro asp ile ile arg asn tyr lys val met
        TCT GCT GTT ACT TTC CCT GAC ATC ATT CGC AAT TAC AAA GTC ATG
                            650
        ala ala glu asn ile pro glu asn pro leu lys tyr leu tyr pro
        GCT GCT GAG AAT ATT CCT GAG AAT CCC CTG AAG TAT CTG TAT CCA
            660                                     670
        asn ile asp lys asp his ala phe gly lys tyr tyr ser arg pro
        AAT ATT GAC AAA GAC CAT GCC TTT GGA AAG TAT TAC TCC AGG CCA
                                    680
        lys glu ala pro glu pro met glu leu asp gly pro lys gly thr
        AAG GAA GCA CCA GAG CCA ATG GAA CTT GAT GGC CCT AAA GGA ACT
            690                                     700
        gly tyr ile lys thr glu leu ile ser val ser glu val his pro
        GGA TAT ATC AAG ACT GAG TTG ATT TCT GTG TCT GAA GTT CAC CCT
                                    710
        ser arg leu gln thr thr asp asn leu leu pro met ser pro glu
        TCT AGA CTT CAG ACC ACA GAC AAC CTG CTC CCC ATG TCT CCT GAG
            720                                     730
        glu phe asp glu val ser arg ile val gly ser val glu phe asp
        GAG TTT GAC GAG GTG TCT CGG ATA GTG GGC TCT GTA GAA TTC GAC
                            739
        ser met met asn thr val AM
        AGT ATG ATG AAC ACA GTA TAG AGCATGAATTTTTTTCATCTTCTCTGGCGACAC
        TTTTCCTTCTCATCTGTGATTCCCTCCTGCTACTCTGTTCCTTCACATCCTGTGTTTCTA
        GGGAAATGAAAGAAAGGCCAGCAAATTCGCTGCAACCTGTTGATAGCAAGTGAATTTTTC
        TCTAACTCAGAAACATCAGTTACTCTGAAGGGCATCATGCATCTTACTGAAGGTAAAATT
        GAAAGGCATTCTCTGAAGAGTGGGTTTCACAAGTGAAAAACATCCAGATACACCCAAAGT
        ATCAGGACGAGAATGAGGGTCCTTTGGGAAAGGAGAAGTTAAGCAACATCTAGCAAATGT
        TATGCATAAAGTCAGTGCCCAACTGTTATAGGTTGTTGGATAAATCAGTGGTTATTTAGG
        GAACTGCTTGACGTAGGAACGGTAAATTTCTGTGGGAGAATTCTTACATGTTTTCTTTGC
        TTTAAGTGTAACTGGCAGTTTTCCATTGGTTTACCTGTGAAATAGTTCAAAGCCAAGTTT
        ATATACAATTATATCAGTCCTCTTTCAAAGGTAGCCATCATGGATCTGGTAGGGGGAAAA
```

FIG. 2E

```
TGTGTATTTTATTACATCTTTCACATTGGCTATTTAAAGACAAAGACAAATTCTGTTTCT
TGAGAAGAGAATATTAGCTTTACTGTTTGTTATGGCTTAATGACACTAGCTAATATCAAT
AGAAGGATGTACATTTCCAAATTCACAAGTTGTGTTTGATATCCAAAGCTGAATACATTC
TGCTTTCATCTTGGTCACATACAATTATTTTTACAGTTCTCCCAAGGGAGTTAGGCTATT
CACAACCACTCATTCAAAAGTTGAAATTAACCATAGATGTAGATAAACTCAGAAATTTAA
TTCATGTTTCTTAAATGGGCTACTTTGTCCTTTTTGTTATTAGGGTGGTATTTAGTCTAT
TAGCCACAAAATTGGGAAAGGAGTAGAAAAAGCAGTAACTGACAACTTGAATAATACACC
AGAGATAATATGAGAATCAGATCATTTCAAAACTCATTTCCTATGTAACTGCATTGAGAA
CTGCATATGTTTCGCTGATATATGTGTTTTCACATTTGCGAATGGTTCCATTCTCTCTC
CTGTACTTTTTCCAGACACTTTTTTGAGTGGATGATGTTTCGTGAAGTATACTGTATTTT
TACCTTTTTCCTTCCTTATCACTGACACAAAAAGTAGATTAAGAGATGGGTTTGACAAGG
TTCTTCCCTTTTACATACTGCTGTCTATGTGGCTGTATCTTGTTTTTCCACTACTGCTAC
CACAACTATATTATCATGCAAATGCTGTATTCTTCTTTGGTGGAGATAAAGATTTCTTGA
GTTTTGTTTTAAAATTAAAGCTAAAGTATCTGTATTGCATTAAATATAATATCGACACAG
TGCTTTCCGTGGCACTGCATACAATCTGAGGCCTCCTCTCTCAGTTTTTATATAGATGGC
GAGAACCTAAGTTTCAGTTGATTTTACAATTGAAATGACTAAAAAACAAAGAAGACAACA
TTAAAAACAATATTGTTTCTA
```

FIG.3A

ATTAAACCTCTCGCCGAGCCCCTCCGCAGACTCTGCGCCGGAAAGTTTCATTTGCTGTATGCC

ATCCTCGAGAGCTGTCTAGGTTAACGTTCGCACTCTGTGTATATAACCTCGACAGTCTTGGCA

CCTAACGTGCTGTGCGTAGCTGCTCCTTTGGTTGAATCCCCAGGCCCTTGTTGGGGCACAAGG

```
                    1                                           10
            met ser gln trp tyr glu leu gln gln leu asp ser lys
    TGGCAGG ATG TCT CAG TGG TAC GAA CTT CAG CAG CTT GAC TCA AAA 20
    phe leu glu gln val his gln leu tyr asp asp ser phe pro met
    TTC CTG GAG CAG GTT CAC CAG CTT TAT GAT GAC AGT TTT CCC ATG 30                                              40
    glu ile arg gln tyr leu ala gln trp leu glu lys gln asp trp
    GAA ATC AGA CAG TAC CTG GCA CAG TGG TTA GAA AAG CAA GAC TGG 50
    glu his ala ala asn asp val ser phe ala thr ile arg phe his
    GAG CAC GCT GCC AAT GAT GTT TCA TTT GCC ACC ATC CGT TTT CAT 60                                              70
    asp leu leu ser gln leu asp asp gln tyr ser arg phe ser leu
    GAC CTC CTG TCA CAG CTG GAT GAT CAA TAT AGT CGC TTT TCT TTG 80
    glu asn asn phe leu leu gln his asn ile arg lys ser lys arg
    GAG AAT AAC TTC TTG CTA CAG CAT AAC ATA AGG AAA AGC AAG CGT 90                                              100
    asn leu gln asp asn phe gln glu asp pro ile gln met ser met
    AAT CTT CAG GAT AAT TTT CAG GAA GAC CCA ATC CAG ATG TCT ATG 110
    ile ile tyr ser cys leu lys glu glu arg lys ile leu glu asn
    ATC ATT TAC AGC TGT CTG AAG GAA GAA AGG AAA ATT CTG GAA AAC 120                                             130
    ala gln arg phe asn gln ala gln ser gly asn ile gln ser thr
    GCC CAG AGA TTT AAT CAG GCT CAG TCG GGG AAT ATT CAG AGC ACA 140
    val met leu asp lys gln lys glu leu asp ser lys val arg asn
    GTG ATG TTA GAC AAA CAG AAA GAG CTT GAC AGT AAA GTC AGA AAT 150                                             160
    val lys asp lys val met cys ile glu his glu ile lys ser leu
    GTG AAG GAC AAG GTT ATG TGT ATA GAG CAT GAA ATC AAG AGC CTG 170
    glu asp leu gln asp glu tyr asp phe lys cys lys thr leu gln
```

FIG. 3B

```
                GAA GAT TTA CAA GAT GAA TAT GAC TTC AAA TGC AAA ACC TTG CAG
      180                                             190
asn arg glu his glu thr asn gly val ala lys ser asp gln lys
AAC AGA GAA CAC GAG ACC AAT GGT GTG GCA AAG AGT GAT CAG AAA
                              200
gln glu gln leu leu leu lys lys met tyr leu met leu asp asn
CAA GAA CAG CTG TTA CTC AAG AAG ATG TAT TTA ATG CTT GAC AAT
      210                                             220
lys arg lys glu val val his lys ile ile glu leu leu asn val
AAG AGA AAG GAA GTA GTT CAC AAA ATA ATA GAG TTG CTG AAT GTC
                              230
thr glu leu thr gln asn ala leu ile asn asp glu leu val glu
ACT GAA CTT ACC CAG AAT GCC CTG ATT AAT GAT GAA CTA GTG GAG
      240                                             250
trp lys arg arg gln gln ser ala cys ile gly gly pro pro asn
TGG AAG CGG AGA CAG CAG AGC GCC TGT ATT GGG GGG CCG CCC AAT
                              260
ala cys leu asp gln leu gln gln val arg gln gln leu lys lys
GCT TGC TTG GAT CAG CTG CAG CAA GTT CGG CAG CAG CTT AAA AAG
      270                                             280
leu glu glu leu glu gln lys tyr thr tyr glu his asp pro ile
TTG GAG GAA TTG GAA CAG AAA TAC ACC TAC GAA CAT GAC CCT ATC
                              290
thr lys asn lys gln val leu trp asp arg thr phe ser leu phe
ACA AAA AAC AAA CAA GTG TTA TGG GAC CGC ACC TTC AGT CTT TTC
      300                                             310
gln gln leu ile gln ser ser phe val val glu arg gln pro cys
CAG CAG CTC ATT CAG AGC TCG TTT GTG GTG GAA AGA CAG CCC TGC
                              320
met pro thr his pro gln arg pro leu val leu lys thr gly val
ATG CCA ACG CAC CCT CAG AGG CCG CTG GTC TTG AAG ACA GGG GTC
      330                                             340
gln phe thr val lys leu arg leu leu val lys leu gln glu leu
CAG TTC ACT GTG AAG TTG AGA CTG TTG GTG AAA TTG CAA GAG CTG
                              350
asn tyr asn leu lys val lys val leu phe asp lys asp val asn
AAT TAT AAT TTG AAA GTC AAA GTC TTA TTT GAT AAA GAT GTG AAT
      360                                             370
glu arg asn thr val lys gly phe arg lys phe asn ile leu gly
GAG AGA AAT ACA GTA AAA GGA TTT AGG AAG TTC AAC ATT TTG GGC
                              380
thr his thr lys val met asn met glu glu ser thr asn gly ser
ACG CAC ACA AAA GTG ATG AAC ATG GAG GAG TCC ACC AAT GGC AGT
```

FIG.3C

```
        390                                                     400
leu ala ala glu phe arg his leu gln leu lys glu gln lys asn
CTG GCG GCT GAA TTT CGG CAC CTG CAA TTG AAA GAA CAG AAA AAT 410
ala gly thr arg thr asn glu gly pro leu ile val thr glu glu
GCT GGC ACC AGA ACG AAT GAG GGT CCT CTC ATC GTT ACT GAA GAG 420                                             430
leu his ser leu ser phe glu thr gln leu cys gln pro gly leu
CTT CAC TCC CTT AGT TTT GAA ACC CAA TTG TGC CAG CCT GGT TTG 440
val ile asp leu glu thr thr ser leu pro val val val ile ser
GTA ATT GAC CTC GAG ACG ACC TCT CTG CCC GTT GTG GTG ATC TCC 450                                             460
asn val ser gln leu pro ser gly trp ala ser ile leu trp tyr
AAC GTC AGC CAG CTC CCG AGC GGT TGG GCC TCC ATC CTT TGG TAC 470
asn met leu val ala glu pro arg asn leu ser phe phe leu thr
AAC ATG CTG GTG GCG GAA CCC AGG AAT CTG TCC TTC TTC CTG ACT 480                                             490
pro pro cys ala arg trp ala gln leu ser glu val leu ser trp
CCA CCA TGT GCA CGA TGG GCT CAG CTT TCA GAA GTG CTG AGT TGG 500
gln phe ser ser val thr lys arg gly leu asn val asp gln leu
CAG TTT TCT TCT GTC ACC AAA AGA GGT CTC AAT GTG GAC CAG CTG 510                                             520
asn met leu gly glu lys leu leu gly pro asn ala ser pro asp
AAC ATG TTG GGA GAG AAG CTT CTT GGT CCT AAC GCC AGC CCC GAT 530
gly leu ile pro trp thr arg phe cys lys glu asn ile asn asp
GGT CTC ATT CCG TGG ACG AGG TTT TGT AAG GAA AAT ATA AAT GAT 540                                             550
lys asn phe pro phe trp leu trp ile glu ser ile leu glu leu
AAA AAT TTT CCC TTC TGG CTT TGG ATT GAA AGC ATC CTA GAA CTC 560
ile lys lys his leu leu pro leu trp asn asp gly cys ile met
ATT AAA AAA CAC CTG CTC CCT CTC TGG AAT GAT GGG TGC ATC ATG 570                                             580
gly phe ile ser lys glu arg glu arg ala leu leu lys asp gln
GGC TTC ATC AGC AAG GAG CGA GAG CGT GCC CTG TTG AAG GAC CAG 590
gln pro gly thr phe leu leu arg phe ser glu ser ser arg glu
CAG CCG GGG ACC TTC CTG CTG CGG TTC AGT GAG AGC TCC CGG GAA
```

FIG. 3D

```
      600                                              610
gly ala ile thr phe thr trp val glu arg ser gln asn gly gly
GGG GCC ATC ACA TTC ACA TGG GTG GAG CGG TCC CAG AAC GGA GGC 620
glu pro asp phe his ala val glu pro tyr thr lys lys glu leu
GAA CCT GAC TTC CAT GCG GTT GAA CCC TAC ACG AAG AAA GAA CTT 630                                              640
ser ala val thr phe pro asp ile ile arg asn tyr lys val met
TCT GCT GTT ACT TTC CCT GAC ATC ATT CGC AAT TAC AAA GTC ATG 650
ala ala glu asn ile pro glu asn pro leu lys tyr leu tyr pro
GCT GCT GAG AAT ATT CCT GAG AAT CCC CTG AAG TAT CTG TAT CCA 660                                              670
asn ile asp lys asp his ala phe gly lys tyr tyr ser arg pro
AAT ATT GAC AAA GAC CAT GCC TTT GGA AAG TAT TAC TCC AGG CCA 680
lys glu ala pro glu pro met glu leu asp gly pro lys gly thr
AAG GAA GCA CCA GAG CCA ATG GAA CTT GAT GGC CCT AAA GGA ACT 690                                              700 701
gly tyr ile lys thr glu leu ile ser val ser glu val OC
GGA TAT ATC AAG ACT GAG TTG ATT TCT GTG TCT GAA GTG TAA GTGAAC
```

ACAGAAGAGTGACATGTTTACAAACCTCAAGCCAGCCTTGCTCCTGGCTGGGGCCTGTTG

AAGATGCTTGTATTTTACTTTTCCATTGTAATTGCTATCGCCATCACAGCTGAACTTGTT

GAGATCCCCGTGTTACTGCCTATCAGCATTTTACTACTTTAAAAAAAAAAAAAAAAGCCA

AAAACCAAATTTGTATTTAAGGTATATAAATTTTCCCAAAACTGATACCCTTTGAAAAAG

TATAAATAAAATGAGCAAAAGTTGAA

FIG. 5A
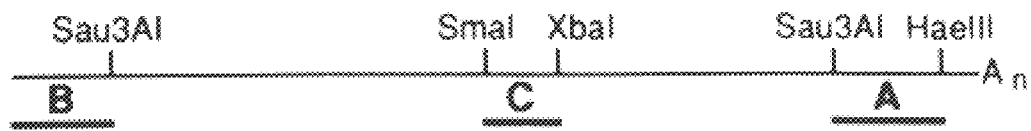
FIG. 5B
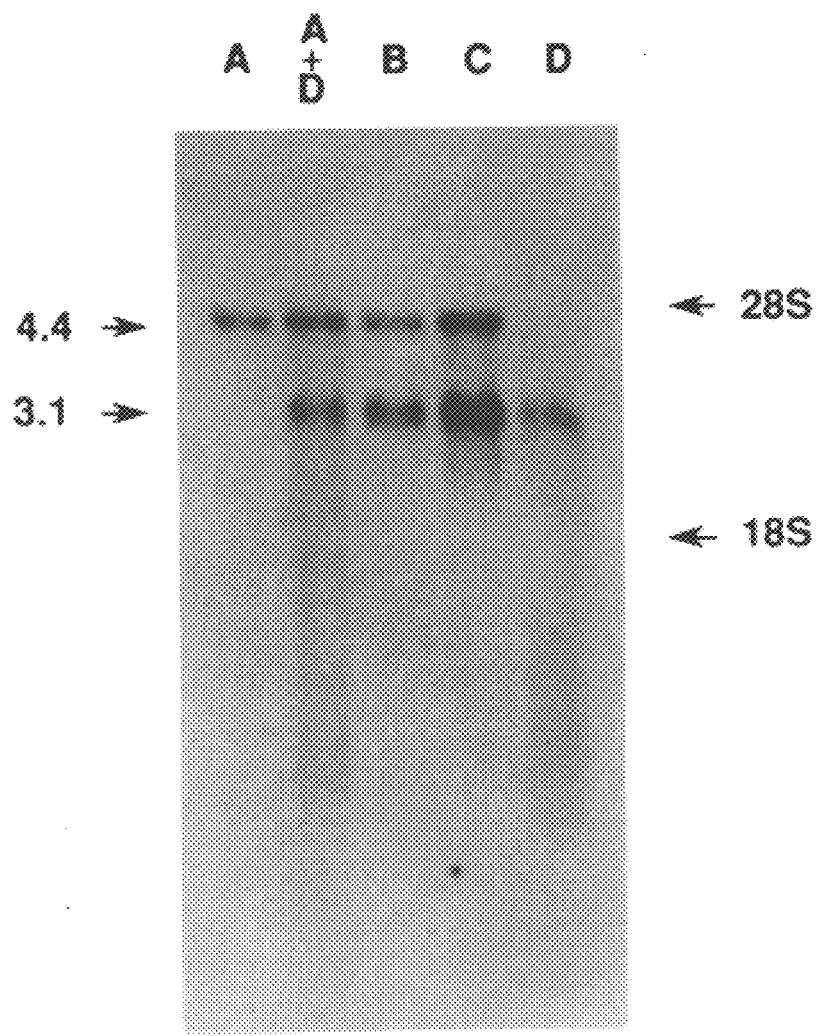

FIG.6

```
  1  MSQWYELQQLDSKFLEQVHQLYDDSFPMEIRQYLAQWLEKQDWEHAANDV

51  SFATIRFHDLLSQLDDQYSRFSLENNFLLQHNIRKSKRNLQDNFQEDPIQ

101  MSMIIYSCLKEERKILENAQRFNQAQSGNIQSTVMLDKQKELDSKVRNVK

151  DKVMCIEHEIKSLEDLQDEYDFKCKTLQNREHETNGVAKSDQKQEQLLLK

201  KMYLMLDNKRKEVVHKIIELLNVTELTQNALINDELVEWKRRQQSACIGG

251  PPNACLDQLQQVRQQLKKLEELEQKYTYEHDPITKNKQVLWDRTFSLFQQ

301  LIQSSFVVERQPCMPTHPQRPLVLKTGVQFTVKLRLLVKLQELNYNLKVK

351  VLFDKDVNERNTVKGFRKFNILGTH KVMNMEESTNGSLAAEFRHLQLKE

401  QKNAGTRTHEGPLIVTEELHSLSFETQLCQPGLVIDLETTSLPVVVISNV

451  SQLPSGWASILWYNMLVAEPRNLSFFLTPPCARWAQLSEVLSWQFSSVTK
                 127
501  RGLNVDQLNMLGEKLLGPNASPDGLIPWTRFCKENINDKNFPFWLWIESI
        119
551  LELIKKHLLPLWNDGCIMGFISKERERALLKDQQPGTFLLRFSESSREGA

601  ITFTWVERSQNGGEPDFHAVEPYTKKELSAVTFPDIIRNYKVMAAENIPE
                                                113a
651  NPLKYLYPNIDKDHAFGKYYSRPKEAPEPMELDGPKGTGYIKTELISVSE
           113b
701  VHPSRLQTTDNLLPMSPEEFDEVSRIVGSVEFDSMMNTV
     ↑
last amino acid of 84 kd
```

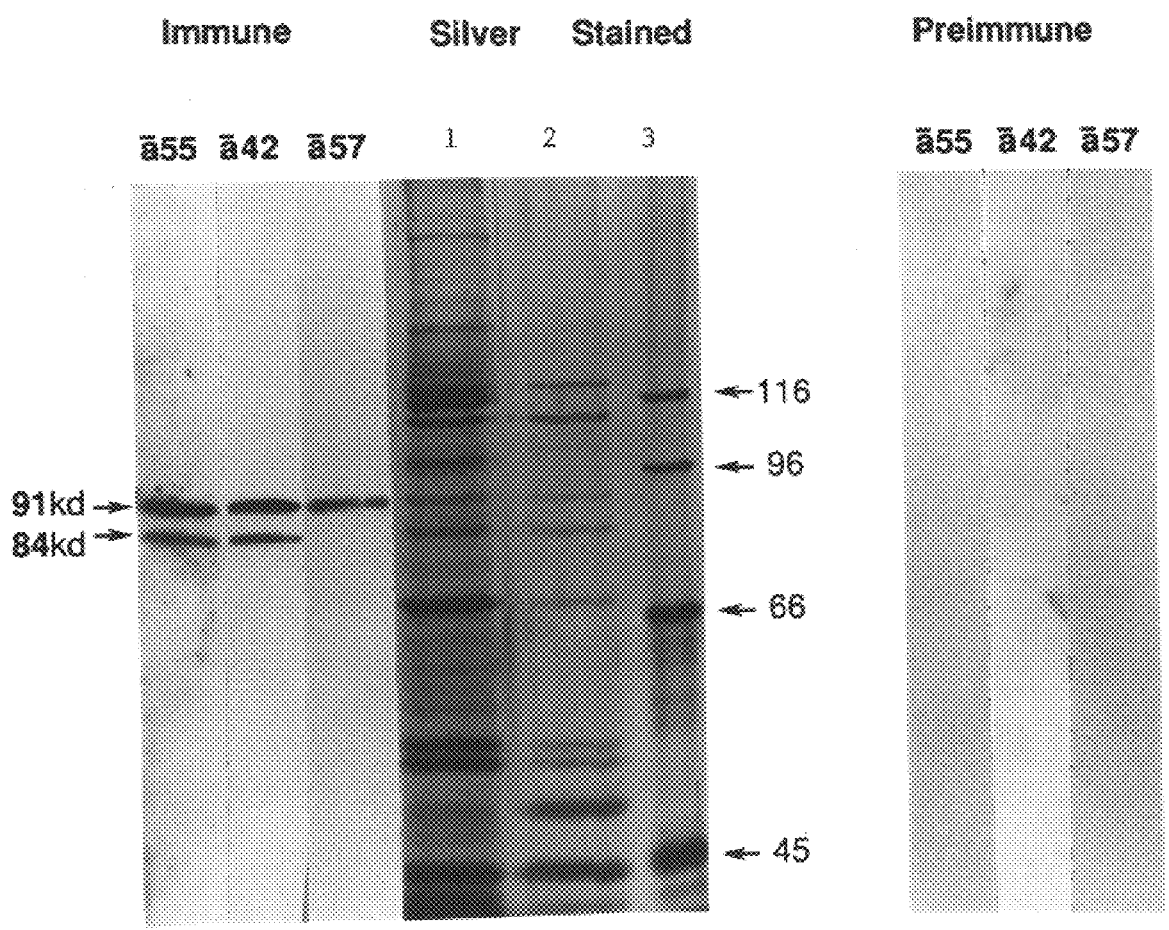

FIG. 8A

```
  1:  MAQWEMLQNLDSPFQDQLHQLYSHSLLPVDIRQYLAVWIEDQNWQEAALGSDDSKATMLF
 61:  FHFLDQLNYECGRCSQDPESLLLQHNLRKFCRDIQPFSQDPTQLAEMIFNLLEEKRILI
121:  QAQRAQLEQGEPVLETPVESQQHEIESRILDLRAMMEKLVKSISQLKDQQDVECFRYKIQ
                            ────────────────────────
                                    Helix 1
181:  AKGKTPSLDPHQTKEQKILQETLNELDKRRKEVLDASKALLGRLTTLIELLLPKLEEWKA
             ──                ────────────────────
              A                      Helix 2
241:  QQQKACIRAPIDHGLEQLETWETAGAKLLFHLRQLLKELKGLSCLVSYQDDPLTKGVDLR
      ───                ─────────────────────
       B                        Helix 3
301:  NAQVTELLQRLLHRAFVVETQPCMPQTPHRPLILKTGSKFTVRTRLLVRLQEGNESLTVE
361:  VSIDRNPPQLQGFRKFNLLTSNQKTLTPEKGQSQGLIWDFGYLTLVEQRSGGSGKGSNKG
421:  PLGVTEELHIISFTVKYTYQGLKQELKTDTLPVVIISNMNQLSIAWASVLWFNLLSPNLQ
481:  NQQFFSNPPKAPWSLLGPALSWQFSSYVGRGLNSDQLSMLRNKLFGQNCRTEDPLLSWAD
                                                         ────────
                                                             C
541:  FTKRESPPGKLPFWTWLDKIELVHDHLKDLWNDGRIMGFVSRSQERRLLKKTMSGTFLL
601:  RFSESSEGGITCSWVEHQDDDKVLIYSVQPYTKEVLQSLPLTEIIRHYQLLTEENIPNP
                                                        ──────────
                                                            D
661:  LRFLYPRIPRDEAFGCYYQEKVNLQERRKYLKHRLIVVSNRQVDELQQPLEKPEPELES
721:  LLELGLVPEPEPELSLDLEPLLKAGLDLGPELESVLESTLEPVIEPTLCMVSQTVPEPDQG
781:  PVSQPVPEPDLPCDLRHLNTEPMEIERNCVKIEEIMPNGDPLLAGQNTVDEVYVSRPSHF
                                      ─
                                      E
841:  YTDGPLMPSDF
```

FIG. 8B

| | |
|---|---|
| 113 kDa | MAQWEMLQNLDSPFQDQLHQLYSHSLLPVDIRQYLAVWIEDQNWQEAALGSDDSKATMLF |
| 91/84 kDa | MSQWYELQQLDSKFLEQVHQLYDDS-FPMEIRQYLAQWLEKQDWEHAA--NDVSFATIRF |
| 61 | FHFLDQLNYECGRCSQDPESLLLQHNLRKFCRDIQP-FSQDPTQLAEMIFNLLLEEKRIL |
| 57 | HDLLSQLDDQYSRFSLE-NNFLLQHNIRKSKRNLQDNFQEDPIQMSMIIYSCLKEERKIL |
| 120 | IQAQRAQLEQGEPVLETPVESQQHEIESRILDLRAMMEKLVKSISQLKDQQDVFCFRYK- |
| 117 | ENAQRFNQAQSGNIQSTVMLDKQKELDSKVRNVKDKVMCIEHEIKSLEDLQDEYDFKCKT |
| 179 | IQAKGKTPS--LDPHQTKEQKILQETLNELDKRRKEVLDASKALLGRLTTLIE--LLLPK |
| 177 | LQNREHETNGVAKSDQKQEQLLLKKMYLMLDNKRKEVVHKIIELL-NVTELTQNALINDE |
| 235 | LEEWKAQQQKACIRAPIDHGLEQIETWFTAGAKLLFHLRQLLKELKGLSCLVSYQDDPLT |
| 236 | IVEWKRRQQSACIGGEPPNACLDQLQ-----------QVRQQLKKLEELEQKYTYEHDPIT |
| 295 | KGVDLRNAQVTELLQRLLHRAFVVETQPCMPQTPHRPLILKTGSKFTVRTRLLVRLQEGN |
| 285 | KNKQVLWDRTFSLFQQLIQSSFVVERQPCMPTHPQRPLVLKTGVQFTVKLRLLVKLQELN |
| 355 | ESLTVEVSIDRNPPQ---LQGFRKFNILTSNQKTLTPEKGQSQGLIWDFGYLTLVEQRSG |
| 345 | YNLKVKVLFDKDVNERNTVKGFRKFNILGTHTKVMNMEESTNGSLAAEFRHLQLKEQKNA |
| 412 | GSGKGSNKGPLGVTEELHIISFTVKYTYQGLKQELKTDTLPVVISNMNQLSIAWASVLW |
| 405 | GT--RTNEGPLIVTEELHSLSFETQLCQPGLVIDLETTSLPVVVISNVSQLPSGWASILW |
| 472 | FNLLSPNLQNQQFFSNPPKAPWSILGPALSWQFSSYVGRGLNSDQLSMLRNKLFGQNCRT |
| 463 | YNMLVAEPRNLSFFLTPPCARWAQLSEVLSWQFSSVTKRGLNVDQLNMLGEKLLGPNASP |
| 532 | EDPLLSWADFTKRESPPGKLPFWTWLDKILELVHDHLKDLWNDGRIMGFVSRSQERRLLK |
| 523 | DG-LIPWTRFCKENINDKNFPFWLWIESILELIKKHLLPLWNDGCIMGFISKERERALLK |
| 592 | KTMSGTFLLRFSESS-EGGITCSWVEH-QDDDKVLIYSVQPYTKEVLQSLPLTEIIRHYQ |
| 582 | DQQPGTFLLRFSESSREGAITFTWVERSQNGGEPDFHAVEPYTKKELSAVTFPDIIRNYK |
| 650 | LLTEENIPENPLRFLYPRIPRDEAFGCYY------QEKVNIQERR--KYLKHRLIVVSNR |
| 642 | VMAAENIPENPLKYLYPNIDKDHAFGKYYSRPKEAPEPMELDGPKGTGMIKTELISVSEV |
| 702 | QVDELQQPLELKP |
| 702 | HPSRLQTTDNLLP |

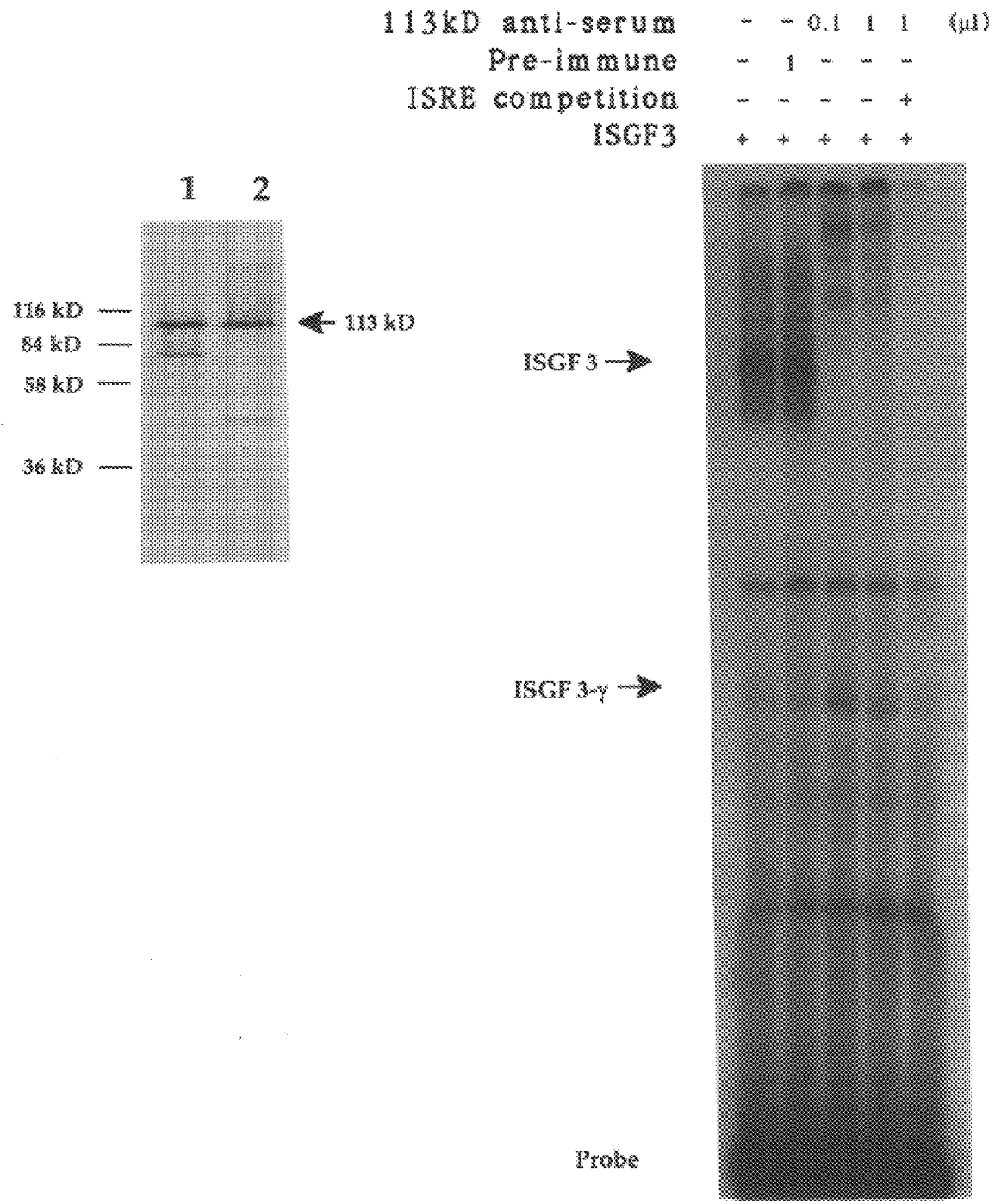

FIG. 13A

```
  1  MSQWFELQQL DSKFLEQVHQ LYDDSFPMEI RQYLAQWLEK QDWEHAAYDV

51  SFATIRFHDL LSQLDDQYSR FSLENNFLLQ HNIRKSKRNL QDNFQEDPVQ

101  MSMIIYNCLK EERKILENAQ RFNQAQEGNI QNTVMLDKQK ELDSKVRNVK

151  DQVMCIEQEI KTLEELQDEY DFKCKTSQNR EGEANGVAKS DQKQEQLLLH

201  KMFLMLDNKR KEIIHKIREL LNSIELTQNT LINDELVEWK RRQQSACIGG

251  PPNACLDQLQ TWFTIVAETL QQIRQQLKKL EELEQKFTYE PDPITKNKQV

301  LSDRTFLLFQ QLIQSSFVVE RQPCMPTHPQ RPLVLKTGVQ FTVKSRLLVK

351  LQESNLLTKV KCHFDKDVNE KNTVKGFRKF NILGTHTKVM NMEESTNGSL

401  AAELRHLQLK EQKNAGNRTN EGPLIVTEEL HSLSFETQLC QPGLVIDLET

451  TSLPVVVISN VSQLPSGWAS ILWYNMLVTE PRNLSFFLNP PCAWWSQLSE

501  VLSWQFSSVT KRGLNADQLS MLGEKLLGPN AGPDGLIPWT RFCKENINDK

551  NFSFWPWIDT ILELIKNDLL CLWNDGCIMG FISKERERAL LKDQQPGTFL

601  LRFSESSREG AITFTWVERS QNGGEPDFHA VEPYTKKELS AVTFPDIIRN

651  YKVMAAENIP ENPLKYLYPN IDKDHAFGKY YSRPKEAPEP MELDDPKRTG

701  YIKTELISVS EVHPSRLQTT DNLLPMSPEE FDEMSRIVGP EFDSMMSTV
```

FIG. 13B

```
   1  caggatgtca cagtggttcg agcttcagca gctggactcc aagttcctgg
  51  agcaggtcca ccagctgtac gatgacagtt tccccatgga aatcagacag
 101  tacctggccc agtggctgga aaagcaagac tgggagcacg ctgcctatga
 151  tgtctcgttt gcgaccatcc gcttccatga cctcctctca cagctggacg
 201  accagtacag ccgcttttct ctggagaata atttcttgtt gcagcacaac
 251  atacggaaaa gcaagcgtaa tctccaggat aacttccaag aagatcccgt
 301  acagatgtcc atgatcatct acaactgtct gaaggaagaa aggaagattt
 351  tggaaaatgc ccaaagattt aatcaggccc aggagggaaa tattcagaac
 401  actgtgatgt tagataaaca gaaggagctg acagtaaag tcagaaatgt
 451  gaaggatcaa gtcatgtgca tagagcagga aatcaagacc ctagaagaat
 501  tacaagatga atatgacttt aaatgcaaaa cctctcagaa cagagaaggt
 551  gaagccaatg gtgtggcgaa gagcgaccaa aaacaggaac agctgctgct
 601  ccacaagatg tttttaatgc ttgacaataa gagaaaggag ataattcaca
 651  aaatcagaga gttgctgaat tccatcgagc tcactcagaa cactctgatt
 701  aatgacgagc tcgtggagtg gaagcgaagg cagcagagcg cctgcatcgg
 751  gggaccgccc aacgcctgcc tggatcagct gcaaacgtgg ttcaccattg
 801  ttgcagagac cctgcagcag atccgtcagc agcttaaaaa gctggaggag
 851  ttggaacaga aattcaccta tgagcccgac cctattacaa aaaacaagca
 901  ggtgttgtca gatcgaacct tcctcctctt ccagcagctc attcagagct
 951  ccttcgtggt agaacgacag ccgtgcatgc ccactcaccc gcagaggccc
1001  ctggtcttga agactggggt acagttcact gtcaagtcga gactgttggt
1051  gaaattgcaa gagtcgaatc tattaacgaa agtgaaatgt cactttgaca
1101  aagatgtgaa cgagaaaaac acagttaaag gatttcggaa gttcaacatc
1151  ttgggtacgc acacaaaagt gatgaacatg aagaatcca ccaacggaag
1201  tctggcagct gagctccgac acctgcaact gaaggaacag aaaaacgctg
1251  ggaacagaac taatgagggg cctctcattg tcaccgaaga acttcactct
1301  cttagctttg aaacccagtt gtgccagcca ggcttggtga ttgacctgga
1351  gaccacctct cttcctgtcg tggtgatctc caacgtcagc cagctcccca
```

FIG.13C

```
1401   gtggctgggc gtctatcctg tggtacaaca tgctggtgac agagcccagg
1451   aatctctcct tcttcctgaa ccccccgtgc gcgtggtggt cccagctctc
1501   agaggtgttg agttggcagt tttcatcagt caccaagaga ggtctgaacg
1551   cagaccagct gagcatgctg ggagagaagc tgctgggccc taatgctggc
1601   cctgatggtc ttattccatg gacaaggttt tgtaaggaaa atattaatga
1651   taaaaatttc tccttctggc cttggattga caccatccta gagctcatta
1701   agaacgacct gctgtgcctc tggaatgatg ggtgcattat gggcttcatc
1751   agcaaggagc gagaacgcgc tctgctcaag gaccagcagc cagggacgtt
1801   cctgcttaga ttcagtgaga gctcccggga agggccatc acattcacat
1851   gggtggaacg gtcccagaac ggaggtgaac ctgacttcca tgccgtggag
1901   ccctacacga aaaagaact ttcagctgtt actttcccag atattattcg
1951   caactacaaa gtcatggctg ccgagaacat accagagaat cccctgaagt
2001   atctgtaccc caatattgac aaagaccacg cctttgggaa gtattattcc
2051   agaccaaagg aagcaccaga accgatggag cttgacgacc ctaagcgaac
2101   tggatacatc aagactgagt tgatttctgt gtctgaagtc caccttcta
2151   gacttcagac cacagacaac ctgcttccca tgtctccaga ggagtttgat
2201   gagatgtccc ggatagtggg ccccgaattt gacagtatga tgagcacagt
2251   ataaacacga atttctctct ggcgaca
```

FIG. 14A

```
  1  MSQWNQVQQL EIKFLEQVDQ FYDDNFPMEI RHLLAQWIET QDWEVASNNE

51  TMATILLQNL LIQLDEQLGR VSKEKNLLLI HNLKRIRKVL QGKFHGNPMH

101  VAVVISNCLR EERRILAAAN MPIQGPLEKS LQSSSVSERQ RNVEHKVSAI

151  KNSVQMTEQD TKYLEDLQDE FDYRYKTIQT MDQGDKNSIL VNQEVLTLLQ

201  EMLNSLDFKR KEALSKMTQI VNETDLLMNS MLLEELQDWK KRHRIACIGG

251  PLHNGLDQLQ NCFTLLAESL FQLRQQLEKL QEQSTKMTYE GDPIPAQRAH

301  LLERATFLIY NLFKNSFVVE RHACMPTHPQ RPMVLKTLIQ FTVKLRLLIK

351  LPELNYQVKV KASIDKNVST LSNRRFVLCG THVKAMSSEE SSNGSLSVEL

401  DIATQGDEVQ YWSKGNEGCH MVTEELHSIT FETQICLYGL TINLETSSLP

451  VVMISNVSQL PNAWASIIWY NVSTNDSQNL VFFNNPPSVT LGQLLEVMSW

501  QFSSYVGRGL NSEQLNMLAE KLTVQSNYND GHLTWAKFCK EHLPGKTFTF

551  WTWLEAILDL IKKHILPLWI DGYIMGFVSK EKERLLLKDK MPGTFLLRFS

601  ESHLGGITFT WVDQSENGEV RFHSVEPYNK GRLSALAFAD ILRDYKVIMA

651  ENIPENPLKY LYPDIPKDKA FGKHYSSQPC EVSRPTERGD KGYVPSVFIP

701  ISTIRSDSTE PQSPSDLLPM SPSAYAVLRE NLSPTTIETA MNSPYSAE
```

FIG.14B

```
  1  tgccactacc tggacggaga gagagagagc agcatgtctc agtggaatca
 51  agtccaacaa ttagaaatca agttttgga gcaagtagat cagttctatg
101  atgacaactt tcctatggaa atccggcatc tgctagctca gtggattgag
151  actcaagact gggaagtagc ttctaacaat gaaactatgg caacaattct
201  gcttcaaaac ttactaatac aattggatga acagttgggg cgggtttcca
251  aagaaaaaaa tctgctattg attcacaatc taaagagaat tagaaaagtt
301  cttcagggca agtttcatgg aaatccaatg catgtagctg tggtaatttc
351  aaattgctta agggaagaga ggagaatatt ggctgcagcc aacatgccta
401  tccagggacc tctggagaaa tccttacaga gttcttcagt ttctgaaaga
451  caaaggaatg tggaacacaa agtgtctgcc attaaaaaca gtgtgcagat
501  gacagaacaa gataccaaat acttagaaga cctgcaagat gagtttgact
551  acaggtataa acaattcag acaatggatc agggtgacaa aaacagtatc
601  ctggtgaacc aggaagtttt gacactgctg caagaaatgc ttaatagtct
651  ggacttcaag agaaaggaag cactcagtaa gatgacgcag atagtgaacg
701  agacagacct gctcatgaac agcatgcttc tagaagagct gcaggactgg
751  aaaaagcggc acaggattgc ctgcattggt ggcccgctcc acaatgggct
801  ggaccagctt cagaactgct ttaccctact ggcagagagt cttttccaac
851  tcagacagca actggagaaa ctacaggagc aatctactaa aatgacctat
```

FIG.14C

```
 901  gaaggggatc ccatccctgc tcaaagagca cacctcctgg aaagagctac 951  cttcctgatc tacaaccttt tcaagaactc atttgtggtc gagcgacacg 1001  catgcatgcc aacgcaccct cagaggccga tggtacttaa aaccctcatt 1051  cagttcactg taaaactgag attactaata aaattgccgg aactaaacta 1101  tcaggtgaaa gtaaaggcgt ccattgacaa gaatgtttca actctaagca 1151  atagaagatt tgtgctttgt ggaactcacg tcaaagctat gtccagtgag 1201  gaatcttcca atgggagcct ctcagtggag ttagacattg caacccaagg 1251  agatgaagtg cagtactgga gtaaaggaaa cgagggctgc cacatggtga 1301  cagaggagtt gcattccata acctttgaga cccagatctg cctctatggc 1351  ctcaccatta acctagagac cagctcatta cctgtcgtga tgatttctaa 1401  tgtcagccaa ctacctaatg catgggcatc catcatttgg tacaatgtat 1451  caactaacga ctcccagaac ttggtttttct ttaataaccc tccatctgtc 1501  actttgggcc aactcctgga agtgatgagc tggcaatttt catcctatgt 1551  cggtcgtggc cttaattcag agcagctcaa catgctggca gagaagctca 1601  cagttcagtc taactacaat gatggtcacc tcacctgggc caagttctgc 1651  aaggaacatt tgcctggcaa acatttacc ttctggactt ggcttgaagc 1701  aatattggac ctaattaaaa aacatattct tccctctgg attgatgggt 1751  acatcatggg atttgttagt aaagagaagg aacggcttct gctcaaagat 1801  aaaatgcctg ggacattttt gttaagattc agtgagagcc atcttggagg
```

FIG.14D

```
1851  gataaccttc acctgggtgg accaatctga aaatggagaa gtgagattcc 1901  actctgtaga accctacaac aaagggagac tgtcggctct ggccttcgct 1951  gacatcctgc gagactacaa ggttatcatg gctgaaaaca tccctgaaaa 2001  ccctctgaag tacctctacc ctgacattcc caaagacaaa gcctttggca 2051  aacactacag ctcccagccg tgcgaagtct caagaccaac cgaacgggga 2101  gacaagggtt acgtcccctc tgtttttatc cccatttcaa caatccgaag 2151  cgattccacg gagccacaat ctccttcaga ccttctcccc atgtctccaa 2201  gtgcatatgc tgtgctgaga gaaaacctga gcccaacgac aattgaaact 2251  gcaatgaatt ccccatattc tgctgaatga cggtgcaaac ggacacttta 2301  aagaaggaag cagatgaaac tggagagtgt tctttaccat agatcacaat 2351  ttatttcttc ggctttgtaa atacc
```

FIG. 15A

```
  1  MAQWNQLQQL DTRYLKQLHQ LYSDTFPMEL RQFLAPWIES QDWAYAASKE

51  SHATLVFHNL LGEIDQQYSR FLQESNVLYQ HNLRRIKQFL QSRYLEKPME

101  IARIVARCLW EESRLLQTAA TAAQQGGQAN HPTAAVVTEK QQMLEQHLQD

151  VRKRVQDLEQ KMKVVENLQD DFDFNYKTLK SQGDMQDLNG NNQSVTRQKM

201  QQLEQMLTAL DQMRRSIVSE LAGLLSAMEY VQKTLTDEEL ADWKRRPEIA

251  CIGGPPNICL DRLENWITSL AESQLQTRQQ IKKLEELQQK VSYKGDPIVQ

301  HRPMLEERIV ELFRNLMKSA FVVERQPCMP MHPDRPLVIK TGVQFTTKVR

351  LLVKFPELNY QLKIKVCIDK DSGDVAALRG SRKFNILGTN TKVMNMEESN

401  NGSLSAEFKH LTLREQRCGN GGRANCDASL IVTEELHLIT FETEVYHQGL

451  KIDLETHSLP VVVISNICQM PNAWASILWY NMLTNNPKNV NFFTKPPIGT

501  WDQVAEVLSW QFSSTTKRGL SIEQLTTLAE KLLGPGVNYS GCQITWAKFC

551  KENMAGKGFS FWVWLDNIID LVKKYILALW NEGYIMGFIS KERERAILST

601  KPPGTFLLRF SESSKEGGVT FTWVEKDISG KTQIQSVEPY TKQQLNNMSF

651  AEIIMGYKIM DATNILVSPL VYLYPDIPKE EAFGKYCRPE SQEHPEADPG

701  SAAPYLKTKF ICVTPTTCSN TIDLPMSPRT LDSLMQFGNN GEGAEPSAGG

751  QFESLTFDMD LTSECATSPM
```

FIG. 15B

```
  1  gccgcgacca gccaggccgg ccagtcgggc tcagcccgga gacagtcgag 51  acccctgact gcagcaggat ggctcagtgg aaccagctgc agcagctgga 101  cacacgctac ctgaagcagc tgcaccagct gtacagcgac acgttcccca 151  tggagctgcg gcagttcctg gcaccttgga ttgagagtca agactgggca 201  tatgcagcca gcaaagagtc acatgccacg ttggtgtttc ataatctctt 251  gggtgaaatt gaccagcaat atagccgatt cctgcaagag tccaatgtcc 301  tctatcagca caaccttcga agaatcaagc agtttctgca gagcaggtat 351  cttgagaagc caatggaaat tgcccggatc gtggcccgat gcctgtggga 401  agagtctcgc ctcctccaga cggcagccac ggcagcccag caaggggggcc 451  aggccaacca cccaacagcc gccgtagtga cagagaagca gcagatgttg 501  gagcagcatc ttcaggatgt ccggaagcga gtgcaggatc tagaacagaa 551  aatgaaggtg gtggagaacc tccaggacga ctttgatttc aactacaaaa 601  ccctcaagag ccaaggagac atgcaggatc tgaatggaaa caaccagtct 651  gtgaccagac agaagatgca gcagctggaa cagatgctca cagccctgga 701  ccagatgcgg agaagcattg tgagtgagct ggcggggctc ttgtcagcaa 751  tggagtacgt gcagaagaca ctgactgatg aagagctggc tgactggaag 801  aggcggccag agatcgcgtg catcggaggc cctcccaaca tctgcctgga 851  ccgtctggaa aactggataa cttcattagc agaatctcaa cttcagaccc
```

FIG.15C

```
 901  gccaacaaat taagaaactg gaggagctgc agcagaaagt gtcctacaag 951  ggcgaccota tcgtgcagca ccggcccatg ctggaggaga ggatcgtgga 1001  gctgttcaga aacttaatga agagtgcctt cgtggtggag cggcagccct 1051  gcatgcccat gcacccggac cggcccttag tcatcaagac tggtgtccag 1101  tttaccacga aagtcaggtt gctggtcaaa tttcctgagt tgaattatca 1151  gcttaaaatt aaagtgtgca ttgataaaga ctctggggat gttgctgccc 1201  tcagagggtc tcggaaattt aacattctgg gcacgaacac aaaagtgatg 1251  aacatggagg agtctaacaa cggcagcctg tctgcagagt tcaagcacct 1301  gaccottagg gagcagagat gtgggaatgg aggccgtgcc aattgtgatg 1351  cctccttgat cgtgactgag gagctgcacc tgatcaccct cgagactgag 1401  gtgtaccacc aaggcctcaa gattgaccta gagacccact ccttgccagt 1451  tgtggtgatc tccaacatct gtcagatgcc aaatgcttgg gcatcaatcc 1501  tgtggtataa catgctgacc aataacccca agaacgtgaa cttcttcact 1551  aagccgccaa ttggaacctg ggaccaagtg gccgaggtgc tcagctggca 1601  gttctcgtcc accaccaagc gagggctgag catcgagcag ctgacaacgc 1651  tggctgagaa gctcctaggg cctggtgtga actactcagg gtgtcagatc 1701  acatgggcta aattctgcaa agaaaacatg gctggcaagg gcttctcctt 1751  ctgggtctgg ctagacaata tcatcgacct tgtgaaaaag tatatcttgg 1801  ccctttggaa tgaagggtac atcatgggtt tcatcagcaa ggagcgggag
```

FIG. 15D

```
1851  cgggccatcc taagcacaaa gccccgggc accttcctac tgcgcttcag 1901  cgagagcagc aaagaaggag gggtcacttt cacttgggtg gaaaaggaca 1951  tcagtggcaa gacccagatc cagtctgtag agccatacac caagcagcag 2001  ctgaacaaca tgtcatttgc tgaaatcatc atgggctata agatcatgga 2051  tgcgaccaac atcctggtgt ctccacttgt ctacctctac cccgacattc 2101  ccaaggagga ggcatttgga aagtactgta ggcccgagag ccaggagcac 2151  cccgaagccg acccaggtag tgctgccccg tacctgaaga ccaagttcat 2201  ctgtgtgaca ccaacgacct gcagcaatac cattgacctg ccgatgtccc 2251  cccgcacttt agattcattg atgcagtttg gaaataacgg tgaaggtgct 2301  gagccctcag caggagggca gtttgagtcg ctcacgtttg acatggatct 2351  gacctcggag tgtgctacct cccccatgtg aggagctgaa accagaagct 2401  gcagagacgt gacttgagac acctgccccg tgctccaccc ctaagcagcc 2451  gaaccccata tcgtctgaaa ctcctaactt tgtggttcca gatttttttt 2501  tttaatttcc tacttctgct atctttgggc aatctgggca cttttaaaa 2551  gagagaaatg agtgagtgtg ggtgataaac tgttatgtaa agaggagaga 2601  cctctgagtc tggggatggg gctgagagca gaagggaggc aaaggggaac 2651  acctcctgtc ctgcccgcct gccctccttt ttcagcagct cgggggttgg 2701  ttgttagaca agtgcctcct ggtgcccatg gctacctgtt gccccactct 2751  gtgagctgat accccattct gggaactcct ggctctgcac tttcaacctt
```

FIG.15E 2801 gctaatatcc acatagaagc taggactaag cccaggaggt tcctctttaa 2851 attaaaaaaa aaaaaaaa

FIG. 23A

```
              βA1          αA2                                          βB5
stat91 (569) LLPL WND GRCIMGFI SKERERALLK DQQP  G TFLLRFS ESSRE G AITFWVER (619)
src    (145) AEE  WYF GKI     TRRESERLLL NPENPRG TFLVRES ETTK  G AYCLSVSD (188)
lck    (127) WFF  KNL         SRKDAERQLL APGNTHG SFLIRES ESTA  G SFSLSVRD (168)
abl    (141) EKHS WYH GPV     SRNAAEYLLS SGIN   G SFLVRES DRRP  G QRSISLRY (184)
p85αN  (330) QDAE WYW GDI     SREEVNEKLR DTAD   G TFLVRDA STKMH G DYTLTLRK (374)

SCR'S        XXX  [-] [------] XXXXXXXX [-----] XXXXX [-----] XXX [-----] XXXXXX [-----]
Name         NA   βA  AA       αA        AB     βB    BC     βC
```

```
                                                                βD6
stat91 (620) S Q N  GGEPDFHAVEPYTKKELSAVTFP IIRNYKV MAAENIPENPL (664)
                   D
src    (189) F FD NAK GL                    NVRHYKI RKLDS       G (210)
lck    (169) D FD QNQ GE                    VVKHYKI RNLDN       G (189)
abl    (185) E  E    G                      RVYHYRI NTASD       G (200)
p85αN  (375)         GG                     NNKLIKI FHR D       G (388)

SCR'S        [------------------------------] XXXXXXX X [-----] DE
Name                    CD                     βD  βD'
```

FIG. 23B

```
                                                      αB9
                                                       |
stat91 (665)  KYLY  P   NID K KDHAFGKYYSRP PK EA PEP M     ELD GPKGTGYIKT (704)
src    (211)  GFYI TSR  TQF S SLQQLVAYYSKH AD GL CH        RLT NVC PTS   (248)
lck    (190)  GFYI SPR  ITF P GLHDLVRHYTNA SD GL CT        RLS RPC QTQ   (227)
abl    (201)  KLYV SSE  SRF N TLAELVHHSTV  AD GL IT        TLH YPA PKR   (238)
p85αN  (389)  KYGF SDP  LTF N SVVELINHYRHE S  LA QYN PKLDV KL LYP        (427)

SCR'S    XXX                     XXXXXXXXXX                      
         [--] [-] [-]            [----------]    [-----------]   [-] [-]
          βE  EF  βF                 αB               BG          βG GΩ

Name
```

NUCLEIC ACIDS ENCODING RECEPTOR RECOGNITION FACTOR STAT1α AND STAT1β, AND METHODS OF USE THEREOF

CROSS-REFERENCE TO RELATED APPLICATIONS

The present Application is a Division of U.S. Ser. No. 08/212/185, filed Mar. 11, 1994 which is a Continuation-In-Part of copending U.S. Ser. No. 08/126,588 and copending U.S. Ser. No. 08/126,595, both filed Sep. 24, 1993, both now abandoned which are both Continuations-In-Part of copending U.S. Ser. No. 07/980,498, filed Nov. 23, 1992, now abandoned which is a Continuation-In-Part of U.S. Ser. No. 07/854,296, filed Mar. 19, 1992, now abandoned the disclosures of which are hereby incorporated by reference in their entireties. Applicants claim the benefits of these Applications under 35 U.S.C. § 120.

RELATED PUBLICATIONS

The Applicants are authors or co-authors of several articles directed to the subject matter of the present invention. (1) Darnell et al., "Interferon-Dependent Transcriptional Activation: Signal Transduction Without Second Messenger Involvement?" THE NEW BIOLOGIST, 2(10): 1–4, (1990); (2) X. Fu et al., "ISGF3, The Transcriptional Activator Induced by Interferon α, Consists of Multiple Interacting Polypeptide Chains" PROC. NATL. ACAD. SCI. USA, 87: 8555–8559 (1990); (3) D. S. Kessler et al., "IFNα Regulates Nuclear Translocation and DNA-Binding Affinity of ISGF3, A Multimeric Transcriptional Activator" GENES AND DEVELOPMENT, 4: 1753 (1990). All of the above listed articles are incorporated herein by reference.

TECHNICAL FIELD OF THE INVENTION

The present invention relates generally to intracellular receptor recognition proteins or factors(i.e. groups of proteins), and to methods and compositions including such factors or the antibodies reactive toward them, or analogs thereof in assays and for diagnosing, preventing and/or treating cellular debilitation, derangement or dysfunction. More particularly, the present invention relates to particular IFN-dependent receptor recognition molecules that have been identified and sequenced, and that demonstrate direct participation in intracellular events, extending from interaction with the liganded receptor at the cell surface to transcription in the nucleus, and to antibodies or to other entities specific thereto that may thereby selectively modulate such activity in mammalian cells.

BACKGROUND OF THE INVENTION

There are several possible pathways of signal transduction that might be followed after a polypeptide ligand binds to its cognate cell surface receptor. Within minutes of such ligand-receptor interaction, genes that were previously quiescent are rapidly transcribed (Murdoch et al., 1982; Larner et al., 1984; Friedman et al., 1984; Greenberg and Ziff, 1984; Greenberg et al., 1985). One of the most physiologically important, yet poorly understood, aspects of these immediate transcriptional responses is their specificity: the set of genes activated, for example, by platelet-derived growth factor (PDGF), does not completely overlap with the one activated by nerve growth factor (NGF) or tumor necrosis factor (TNF) (Cochran et al., 1983; Greenberg et al., 1985; Almendral et al., 1988; Lee et al., 1990). The interferons (IFN) activate sets of other genes entirely. Even IFNα and IFNγ, whose presence results in the slowing of cell growth and in an increased resistance to viruses (Tamm et al., 1987) do not activate exactly the same set of genes (Larner et al., 1984; Friedman et al., 1984; Celis et al., 1987, 1985; Larner et al., 1986).

The current hypotheses related to signal transduction pathways in the cytoplasm do not adequately explain the high degree of specificity observed in polypeptide-dependent transcriptional responses. The most commonly discussed pathways of signal transduction that might ultimately lead to the nucleus depend on properties of cell surface receptors containing tyrosine kinase domains [for example, PDGF, epidermal growth factor (EGF), colony-stimulating factor (CSF), insulin-like growth factor-1 (IGF-1); see Gill, 1990; Hunter, 1990) or of receptors that interact with G-proteins (Gilman, 1987). These two groups of receptors mediate changes in the intracellular concentrations of second messengers that, in turn, activate one of a series of protein phosphokinases, resulting in a cascade of phosphorylations (or dephosphorylations) of cytoplasmic proteins.

It has been widely conjectured that the cascade of phosphorylations secondary to changes in intracellular second messenger levels is responsible for variations in the rates of transcription of particular genes (Bourne, 1988, 1990; Berridge, 1987; Gill, 1990; Hunter, 1990). However, there are at least two reasons to question the suggestion that global changes in second messengers participate in the chain of events leading to specific transcriptional responses dependent on specific receptor occupation by polypeptide ligands.

First, there is a limited number of second messengers (cAMP, diacyl glycerol, phosphoinositides, and $Ca^{2+}$ are the most prominently discussed), whereas the number of known cell surface receptor-ligand pairs of only the tyrosine kinase and G-protein varieties, for example, already greatly outnumbers the list of second messengers, and could easily stretch into the hundreds (Gill, 1990; Hunter, 1990). In addition, since many different receptors can coexist on one cell type at any instant, a cell can be called upon to respond simultaneously to two or more different ligands with an individually specific transcriptional response each involving a different set of target genes. Second, a number of receptors for polypeptide ligands are now known that have neither tyrosine linase domains nor any structure suggesting interaction with G-proteins. These include the receptors for interleulin-2 (IL-2) (Leonard et al., 1985), IFNα (Uze et al., 1990), IFNγ (Aguet et al., 1988), NGF (Johnson et al., 1986), and growth hormone (Leung et al., 1987). The binding of each of these receptors to its specific ligand has been demonstrated to stimulate transcription of a specific set of genes. For these reasons it seems unlikely that global intracellular fluctuations in a limited set of second messengers are integral to the pathway of specific, polypeptide ligand-dependent, immediate transcriptional responses.

In PCT International Publication No. WO 92/08740 published May 29, 1992by the applicant herein, the above analysis was presented and it was discovered and proposed that a receptor recognition factor or factors, served in some capacity as a type of direct messenger between liganded receptors at the cell surface and the cell nucleus. One of the characteristics that was ascribed to the receptor recognition factor was its apparent lack of requirement for changes in second messenger concentrations. Continued investigation of the receptor recognition factor through study of the actions of the interferons IFNα and IFNγ has further elucidated the characteristics and structure of the interferon-related factor ISGF-3, and more broadly, the characterization and structure of the receptor recognition factor in a manner that extends beyond earlier discoveries previously described. It is accordingly to the presentation of this updated characterization of the receptor recognition factor and the materials and methods both diagnostic and therapeutic corresponding thereto that the present disclosure is directed.

SUMMARY OF THE INVENTION

In accordance with the present invention, receptor recognition factors have been further characterized that appear to interact directly with receptors that have been occupied by their ligand on cellular surfaces, and which in turn either become active transcription factors, or activate or directly associate with transcription factors that enter the cells' nucleus and specifically binds on predetermined sites and thereby activates the genes. It should be noted that the receptor recognition proteins thus possess multiple properties, among them: 1) recognizing and being activated during such recognition by receptors; 2) being translocated to the nucleus by an inhibitable process (eg. NaF inhibits translocation); and 3) combining with transcription activating proteins or acting themselves as transcription activation proteins, and that all of these properties are possessed by the proteins described herein.

A further property of the receptor recognition factors (also termed herein signal transducers and activators of transcription—STAT) is dimerization to form homodimers or heterodimers upon activation by phosphorylation of tyrosine. In a specific embodiment, infra, Stat91 and Stat84 form homodimers and a Stat915–Stat84 heterodimer. Accordingly, the present invention is directed to such dimers, which can form spontaneously by phophorylation of the STAT protein, or which can be prepared synthetically by chemically cross-linking two like or unlike STAT proteins.

The receptor recognition factor is proteinaceous in composition and is believed to be present in the cytoplasm. The recognition factor is not demonstrably affected by concentrations of second messengers, however does exhibit direct interaction with tyrosine kinase domains, although it exhibits no apparent interaction with G-proteins. More particularly, as is shown in a co-pending, co-owned application entitled "INTERFERON-ASSOCIATED RECEPTOR RECOGNITION FACTORS, NUCLEIC ACIDS ENCODING THE SAME AND METHODS OF USE THEREOF," filed on even date herewith, the 91 kD human interferon (IFN)-γ factor, represented by SEQ ID NO:4 directly interacts with DNA after acquiring phosphate on tyrosine located at position 701 of the amino acid sequence.

The recognition factor is now known to comprise several proteinaceous substituents, in the instance of IFNα and IFNγ. Particularly, three proteins derived from the factor ISGF-3 have been successfully sequenced and their sequences are set forth in FIG. 1 (SEQ ID NOS:1, 2), FIG. 2 (SEQ ID NOS:3, 4) and FIG. 3 (SEQ. ID NOS.5, 6) herein. Additionally, a murine gene encoding the 91 kD protein (i.e. the murine homologue of the human protein having the sequence of SEQ ID NO:4) has been identified and sequenced. The nucleotide sequence (SEQ ID NO:7) and deduced amino acid sequence (SEQ ID NO:8) are shown in FIG. 13A–13C.

In a further embodiment, murine genes encoding homologs of the recognition factor have been succefully sequenced and cloned into plasmids. A gene in plasmid 13sf1 has the nucleotide sequence (SEQ ID NO:9) and deduced amino acid sequence (SEQ ID NO:10) as shown in FIG. 14A–14C. A gene in plasmid 19sf6 has the nucleotide sequence (SEQ ID NO:11) and deduced amino acid sequence (SEQ ID NO:12) shown in FIG. 15A–15C.

It is particularly noteworthy that the protein sequence of FIG. 1 (SEQ ID NO:2) and the sequence of the proteins of FIGS. 2 (SEQ ID NO:4) and 3 (SEQ ID NO:6) derive, respectively, from two different but related genes. Moreover, the protein sequence of FIG. 13 (SEQ ID NO:8) derives from a murine gene that is analogous to the gene encoding the protein of FIG. 2 (SEQ ID NO:4). Of further note is that the protein sequences of FIGS. 14 (SEQ ID NO:10) and 15 (SEQ ID NO:12) derive from two genes that are different from, but related to, the protein of FIG. 13 (FIG ID NO:8). It is clear from these discoveries that a family of genes exists, and that further family members likewise exist. Accordingly, as demonstrated herein, by use of hybridization techniques, additional such family members will be found.

Further, the capacity of such family members to function in the manner of the receptor recognition factors disclosed, herein may be assessed by determining those ligand that cause the phosphorylation of the particular family members.

In its broadest aspect, the present invention extends to a receptor recognition factor implicated in the transcriptional stimulation of genes in target cells in response to the binding of a specific polypeptide ligand to its cellular receptor on said target cell, said receptor recognition factor having the following characteristics:

a) apparent direct interaction with the ligand-bound receptor complex and activation of one or more transcription factors capable of binding with a specific gene;

b) an activity demonstrably unaffected by the presence or concentration of second messengers;

c) direct interaction with tyrosine kinase domains; and d) a perceived absence of interaction with G-proteins.

In a further aspect, the receptor recognition (STAT) protein forms a dimer upon activation by phosphorylation.

In a specific example, the receptor recognition factor represented by SEQ ID NO:4 possesses the added capability of acting as a transcription factor and, in particular, as a DNA binding protein in response to interferon-γ stimulation. This discovery presages an expanded role for the proteins in question, and other proteins and like factors that have heretofore been characterized as receptor recognition factors. It is therefore apparent that a single factor may indeed provide the nexus between the liganded receptor at the cell surface and direct participation in DNA transcriptional activity in the nucleus. This pleiotypic factor has the following characteristics:

a) It interacts with an interferon-γ-bound receptor kinase complex;

b) It is a tyrosine kinase substrate; and c) When phosphorylated, it serves as a DNA binding protein.

More particularly, the factor represented by SEQ ID NO:4 is interferon-dependent in its activity and is responsive to interferon stimulation, particularly that of interferon-γ. It has further been discovered that activation of the factor represented by SEQ ID NO:4 requires phosphorylation of tyrosine-701 of the protein, and further still that tyrosine phosphorylation requires the presence of a functionally active SH2 domain in the protein. Preferably, such SH2 domain contains an amino acid residue corresponding to an arginine at position 602 of the protein.

In a still further aspect, the present invention extends to a receptor recognition factor interactive with a liganded interferon receptor, which receptor recognition factor possesses the following characteristics:
a) it is present in cytoplasm;
b) it undergoes tyrosine phosphorylation upon treatment of cells with IFNα or IFNγ;
c) it activates transcription of an interferon stimulated gene;
d) it stimulates either an ISRE-dependent or a gamma activated site (GAS)-dependent transcription in vivo;
e) it interacts with IFN cellular receptors, and
f) it undergoes nuclear translocation upon stimulation of the IFN cellular receptors with IFN.

The factor of the invention represented by SEQ ID NO:4 appears to act in similar fashion to an earlier determined site-specific DNA binding protein that is interferon-γ dependent and that has been earlier called the γ activating factor (GAF). Specifically, interferon-γ-dependent activation of this factor occurs without new protein synthesis and appears within minutes of interferon-γ treatment, achieves maximum extent between 15 and 30 minutes thereafter, and then disappears after 2–3 hours. These further characteristics of identification and action assist in the evaluation of the present factor for applications having both diagnostic and therapeutic significance.

In a particular embodiment, the present invention relates to all members of the herein disclosed family of receptor recognition factors except the 91 kD protein factors, specifically the proteins whose sequences are represented by one or more of SEQ ID NO:4, SEQ ID NO:6 or SEQ ID NO:8.

The present invention also relates to a recombinant DNA molecule or cloned gene, or a degenerate variant thereof, which encodes a receptor recognition factor, or a fragment thereof, that possesses a molecular weight of about 113 kD and an amino acid sequence set forth in FIG. 1 (SEQ ID NO:2); preferably a nucleic acid molecule, in particular a recombinant DNA molecule or cloned gene, encoding the 113 kD receptor recognition factor has a nucleotide sequence or is complementary to a DNA sequence shown in FIG. 1 (SEQ ID NO:1). In another embodiment, the receptor recognition factor has a molecular weight of about 91 kD and the amino acid sequence set forth in FIG. 2 (SEQ ID NO:4) or FIG. 13 (SEQ ID NO:8); preferably a nucleic acid molecule, in particular a recombinant DNA molecule or cloned gene, encoding the 91 kD receptor recognition factor has a nucleotide sequence or is complementary to a DNA sequence shown in FIG. 2 (SEQ ID NO:3) or FIG. 13 (SEQ ID NO:8). In yet a further embodiment, the receptor recognition factor has a molecular weight of about 84 kD and the amino acid sequence set forth in FIG. 3 (SEQ ID NO:6); preferably a nucleic acid molecule, in particular a recombinant DNA molecule or cloned gene, encoding the 84 kD receptor recognition factor has a nucleotide sequence or is complementary to a DNA sequence shown in FIG. 3 (SEQ ID NO:5). In yet another embodiment, the receptor recognition factor has an amino acid sequence set forth in FIG. 14 (SEQ ID NO:10); preferably a nucleic acid molecule, in particular a recombinant DNA molecule or cloned gene, encoding such receptor recognition factor has a nucleotide sequence or is complementary to a DNA sequence shown in FIG. 14 (SEQ ID NO:9). In still another embodiment, the receptor recognition factor has an amino acid sequence set forth in FIG. 15 (SEQ ID NO:12); preferably a nucleic acid molecule, in particular a recombinant DNA molecule or cloned gene, encoding such receptor recognition factor has a nucleotide sequence or is complementary to a DNA sequence shown in FIG. 15 (SEQ ID NO:11).

The human and murine DNA sequences of the receptor recognition factors of the present invention or portions thereof, may be prepared as probes to screen for complementary sequences and genomic clones in the same or alternate species. The present invention extends to probes so prepared that may be provided for screening cDNA and genomic libraries for the receptor recognition factors. For example, the probes may be prepared with a variety of known vectors, such as the phage λ vector. The present invention also includes the preparation of plasmids including such vectors, and the use of the DNA sequences to construct vectors expressing antisense RNA or ribozymes which would attack the mRNAs of any or all of the DNA sequences set forth in FIGS. 1, 2, 3, 13, 14 and 15 (SEQ ID NOS:1, 3, 5, 7, 9, and 11, respectively). Correspondingly, the preparation of antisense RNA and ribozymes are included herein.

The present invention also includes receptor recognition factor proteins having the activities noted herein, and that display the amino acid sequences set forth and described above and selected from SEQ ID NO:2, SEQ ID NO:4, SEQ ID NO:6, SEQ ID NO:8, SEQ ID NO:10 and SEQ ID NO:12.

In a further embodiment of the invention, the full DNA sequence of the recombinant DNA molecule or cloned gene so determined may be operatively linked to an expression control sequence which may be introduced into an appropriate host. The invention accordingly extends to unicellular hosts transformed with the cloned gene or recombinant DNA molecule comprising a DNA sequence encoding the present receptor recognition factor(s), and more particularly, the complete DNA sequence determined from the sequences set forth above and in SEQ ID NO:1, SEQ ID NO:3, SEQ ID NO:5, SEQ ID NO:7, SEQ ID NO:9 and SEQ ID NO:11.

According to other preferred features of certain preferred embodiments of the present invention, a recombinant expression system is provided to produce biologically active animal or human receptor recognition factor.

The concept of the receptor recognition factor contemplates that specific factors exist for correspondingly specific ligands, such as tumor necrosis factor, nerve growth factor and the like, as described earlier. Accordingly, the exact structure of each receptor recognition factor will understandably vary so as to achieve this ligand and activity specificity. It is this specificity and the direct involvement of the receptor recognition factor in the chain of events leading to gene activation, that offers the promise of a broad spectrum of diagnostic and therapeutic utilities.

The present invention naturally contemplates several means for preparation of the recognition factor, including as illustrated herein known recombinant techniques, and the invention is accordingly intended to cover such synthetic preparations within its scope. The isolation of the cDNA amino acid sequences disclosed herein facilitates the reproduction of the recognition factor by such recombinant techniques, and accordingly, the invention extends to expression vectors prepared from the disclosed DNA sequences for expression in host systems by recombinant DNA techniques, and to the resulting transformed hosts.

The invention includes an assay system for screening of potential drugs effective to modulate transcriptional activity of target mammalian cells by interrupting or potentiating the recognition factor or factors. In one instance, the test drug could be administered to a cellular sample with the ligand that activates the receptor recognition factor, or an extract containing the activated recognition factor, to determine its effect upon the binding activity of the recognition factor to any chemical sample (including DNA), or to the test drug, by comparison with a control.

The assay system could more importantly be adapted to identify drugs or other entities that are capable of binding to the receptor recognition and/or transcription factors or proteins, either in the cytoplasm or in the nucleus, thereby inhibiting or potentiating transcriptional activity. Such assay would be useful in the development of drugs that would be specific against particular cellular activity, or that would potentiate such activity, in time or in level of activity. For example, such drugs might be used to modulate cellular response to shock, or to treat other pathologies, as for example, in making IFN more potent against cancer.

In yet a further embodiment, the invention contemplates antagonists of the activity of a receptor recognition factor (STAT). In particular, an agent or molecule that inhibits dimerization (homodimerization or heterodimerization) can be used to block transcription activation effected by an activated, phosphorylated STAT protein. In a specific embodiment, the antagonist can be a peptide having the sequence of a portion of an SH2 domain of a STAT protein, or the phophotyrosine domaine of a STAT protein, or both. If the peptide contains both regions, preferably the regions are located in tandem, more preferably with the SH2 domain portion N-terminal to the phosphotyrosine portion. In a specific example, infra, such peptides are shown to be capable of disrupting dimerization of STAT proteins.

One-of the characteristics of the present receptor recognition factors is their participation in rapid phosphorylation and dephosphorylation during the course of and as part of their activity. Significantly, such phosphorylation takes place in an interferon-dependent manner and within a few minutes in the case of the ISGF-3 proteins identified herein, on the tyrosine residues defined thereon. This is strong evidence that the receptor recognition factors disclosed herein are the first true substrates whose intracellular function is well understood and whose intracellular activity depends on tyrosine kinase phosphorylation. In particular, the addition of phosphate to the tyrosine of a transcription factor is novel. This suggests further that tyrosine kinase takes direct action in the transmission of intracellular signals to the nucleus, and does not merely serve as a promoter or mediator of serine and/or serinine kinase activity, as has been theorized to date. Also, the role of the factor represented by SEQ ID NO:2 in its activated phosphorylated form suggests possible independent therapeutic use for this activated form. Likewise, the role of the factor as a tyrosine kinase substrate suggests its interaction with kinase in other theatres apart from the complex observed herein.

The diagnostic utility of the present invention extends to the use of the present receptor recognition factors in assays to screen for tyrosine kinase inhibitors.

Because the activity of the receptor recognition-transcriptional activation proteins described herein must maintain tyrosine phosphorylation, they can and presumably are dephosphorylated by specific tyrosine phosphatases. Blocking of the specific phosphatase is therefore an avenue of pharmacological intervention that would potentiate the activity of the receptor recognition proteins.

The present invention likewise extends to the development of antibodies against the receptor recognition factor(s), including naturally raised and recombinantly prepared antibodies. For example, the antibodies could be used to screen expression libraries to obtain the gene or genes that encode the receptor recognition factor(s). Such antibodies could include both polyclonal and monoclonal antibodies prepared by known genetic techniques, as well as bi-specific (chimeric) antibodies, and antibodies including other functionalities suiting them for additional diagnostic use conjunctive with their capability of modulating transcriptional activity.

In particular, antibodies against specifically phosphorylated factors can be selected and are included within the scope of the present invention for their particular ability in following activated protein. Thus, activity of the recognition factors or of the specific polypeptides believed to be causally connected thereto may therefore be followed directly by the assay techniques discussed later on, through the use of an appropriately labeled quantity of the recognition factor or antibodies or analogs thereof.

Thus, the receptor recognition factors, their analogs and/or analogs, and any antagonists or antibodies that may be raised thereto, are capable of use in connection with various diagnostic techniques, including immunoassays, such as a radioimmunoassay, using for example, an antibody to the receptor recognition factor that has been labeled by either radioactive addition, reduction with sodium borohydride, or radioiodination.

In an immunoassay, a control quantity of the antagonists or antibodies thereto, or the like may be prepared and labeled with an enzyme, a specific binding partner and/or a radioactive element, and may then be introduced into a cellular sample. After the labeled material or its binding partner(s) has had an opportunity to react with sites within the sample, the resulting mass may be examined by known techniques, which may vary with the nature of the label attached. For example, antibodies against specifically phosphorylated factors may be selected and appropriately employed in the exemplary assay protocol, for the purpose of following activated protein as described above.

In the instance where a radioactive label, such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

The present invention includes an assay system which may be prepared in the form of a test kit for the quantitative analysis of the extent of the presence of the recognition factors, or to identify drugs or other agents that may mimic or block their activity. The system or test kit may comprise a labeled component prepared by one of the radioactive and/or enzymatic techniques discussed herein, coupling a label to the recognition factors, their agonists and/or antagonists, and one or more additional immunochemical reagents, at least one of which is a free or immobilized ligand, capable either of binding with the labeled component, its binding partner, one of the components to be determined or their binding partner(s).

In a further embodiment, the present invention relates to certain therapeutic methods which would be based upon the activity of the recognition factor(s), its (or their) subunits, or active fragments thereof, or upon agents or other drugs determined to possess the same activity. A first therapeutic method is associated with the prevention of the manifestations of conditions causally related to or following from the binding activity of the recognition factor or its subunits, and comprises administering an agent capable of modulating the production and/or activity of the recognition factor or subunits thereof, either individually or in mixture with each other in an amount effective to prevent the development of those conditions in the host. For example, drugs or other binding partners to the receptor recognition/transcription factors or proteins may be administered to inhibit or potentiate transcriptional activity, as in the potentiation of interferon in cancer therapy. Also, the blockade of the action of specific tyrosine phosphatases in the dephosphorylation of activated (phosphorylated) recognition/transcription factors or proteins presents a method for potentiating the activity of the receptor recognition factor or protein that would concomitantly potentiate therapies based on receptor recognition factor/protein activation.

More specifically, the therapeutic method generally referred to herein could include the method for the treatment of various pathologies or other cellular dysfunctions and derangements by the administration of pharmaceutical compositions that may comprise effective inhibitors or enhancers of activation of the recognition factor or its subunits, or other equally effective drugs developed for instance by a drug screening assay prepared and used in accordance with a further aspect of the present invention. For example, drugs or other binding partners to the receptor recognition/transcription factor or proteins, as represented by SEQ ID NO:2, may be administered to inhibit or potentiate transcriptional activity, as in the potentiation of interferon in cancer therapy. Also, the blockade of the action of specific tyrosine phosphatases in the dephosphorylation of activated (phosphorylated) recognition/transcription factor or protein presents a method for potentiating the activity of the receptor recognition factor or protein that would concomitantly potentiate therapies based on receptor recognition factor/protein activation. Correspondingly, the inhibition or blockade of the activation or binding of the recognition/transcription factor would affect MHC Class II expression and consequently, would promote immunosuppression. Materials exhibiting this activity, as illustrated later on herein by staurosporine, may be useful in instances such as the treatment of autoimmune diseases and graft rejection, where a degree of immunosuppression is desirable.

In particular, the proteins of ISGF-3 whose sequences are presented in SEQ ID NOS:2, 4, 6, 8, 10 or 12 herein, their antibodies, agonists, antagonists, or active fragments thereof, could be prepared in pharmaceutical formulations for administration in instances wherein interferon therapy is appropriate, such as to treat chronic viral hepatitis, hairy cell leukemia, and for use of interferon in adjuvant therapy. The specificity of the receptor proteins hereof would make it possible to better manage the aftereffects of current interferon therapy, and would thereby make it possible to apply interferon as a general antiviral agent.

Accordingly, it is a principal object of the present invention to provide a receptor recognition factor and its subunits in purified form that exhibits certain characteristics and activities associated with transcriptional promotion of cellular activity.

It is a further object of the present invention to provide antibodies to the receptor recognition factor and its subunits, and methods for their preparation, including recombinant means.

It is a further object of the present invention to provide a method for detecting the presence of the receptor recognition factor and its subunits in mammals in which invasive, spontaneous, or idiopathic pathological states are suspected to be present.

It is a further object of the present invention to provide a method and associated assay system for screening substances such as drugs, agents and the like, potentially effective in either mimicking the activity or combating the adverse effects of the recognition factor and/or its subunits in mammals.

It is a still further object of the present invention to provide a method for the treatment of mammals to control the amount or activity of the recognition factor or subunits thereof, so as to alter the adverse consequences of such presence or activity, or where beneficial, to enhance such activity.

It is a still further object of the present invention to provide a method for the treatment of mammals to control the amount or activity of the recognition factor or its subunits, so as to treat or avert the adverse consequences of invasive, spontaneous or idiopathic pathological states.

It is a still further object of the present invention to provide pharmaceutical compositions for use in therapeutic methods which comprise or are based upon the recognition factor, its subunits, their binding partner(s), or upon agents or drugs that control the production, or that mimic or antagonize the activities of the recognition factors.

Other objects and advantages will become apparent to those skilled in the art from a review of the ensuing description which proceeds with reference to the following illustrative drawings.

BRIEF DESCRIPTION OF THE DRAWINGS

FIGS. 1A–1E depicts the full receptor recognition factor nucleic acid sequence and the deduced amino acid sequence derived for the ISGF-3α gene defining the 113 kD protein. The nucleotides are numbered from 1 to 2553 (SEQ ID NO:1), and the amino acids are numbered from 1 to 851 (SEQ ID NO:2).

FIGS. 2A–2E depict the full receptor recognition factor nucleic acid sequence and the deduced amino acid sequence derived for the ISGF-3α gene defining the 91 kD protein. The nucleotides are numbered from 1 to 3943 (SEQ ID NO:3), and the amino acids are numbered from 1 to 750 (SEQ ID NO:4).

FIGS. 3A–3D depicts the full receptor recognition factor nucleic acid sequence and the deduced amino acid sequence derived for the ISGF-3α gene defining the 84 kD protein. The nucleotides are numbered from 1 to 2166 (SEQ ID NO:5), and the amino acids are numbered from 1 to 712 (SEQ ID NO:6).

FIG. 5a–5b generally presents the results of Northern Blot analysis for the 91/84 kD peptides. FIG. 5a presents restriction maps for cDNA clones E4 (top map) and E3 (bottom map) showing DNA fragments that were radiolabeled as probes (probes A–D). FIG. 5b comprises Northern blots of cytoplasmic HeLa RNA hybridized with the indicated probes. The 4.4 and 3.1 KB species as well as the 28S and 18S rRNA bands are indicated.

FIG. 6 depicts the conjoint protein sequence of the 91 kD (SEQ ID NO:4) and 84 kD (SEQ ID NO:6) proteins of ISGF-3. One letter amino acid code is shown for the open reading frame from clone E4, (encoding the 91 kD protein). The 84 kD protein, encoded by a different cDNA (E3), has the identical sequence but terminates after amino acid 712, as indicated. Tryptic peptides t19, t13a, and t13b from the 91 kD protein are indicated. The sole recovered tryptic peptide from the 84 kD protein, peptide t27, was wholly contained within peptide t19 as indicated.

FIG. 7a–7b present the results of Western blot and antibody shift analyses.
 a) Highly purified ISGF-3, fractionated on a 7.0% SDS polyacrylamide gel, was probed with antibodies a42 (amino acids 597–703); a55 (amino acids 2–59); and a57 (amino acids 705–739) in a Western blot analysis. The silver stained part of the gel (lanes a, b, and c) illustrates the location of the ISGF-3 component proteins and the purity of the material used in Western blot: Lane a) Silver stain of protein sample used in all the Western blot experiments (immune and preimmune). Lane b) Material of equal purity to that shown in FIG. 4, for clearer identification of the ISGF-3 proteins. Lane c) Size protein markers indicated.
 b) Antibody interference of the ISGF-3 shift complex; Lane a) The complete ISGF-3 and the free ISGF-3γ component shift with partially purified ISGF-3 are marked; Lane b) Competition with a 100 fold excess of cold ISRE oligonucleotide. Lane c) Shift complex after the addition of 1 ml of preimmune serum to a 12.5 μl shift reaction. Lanes d and e)—Shift complex after the addition of 1 μl of a 1:10 dilution or 1 ml of undiluted a42 antiserum to a 12.5 μl shift reaction.

Methods

Figure 4:
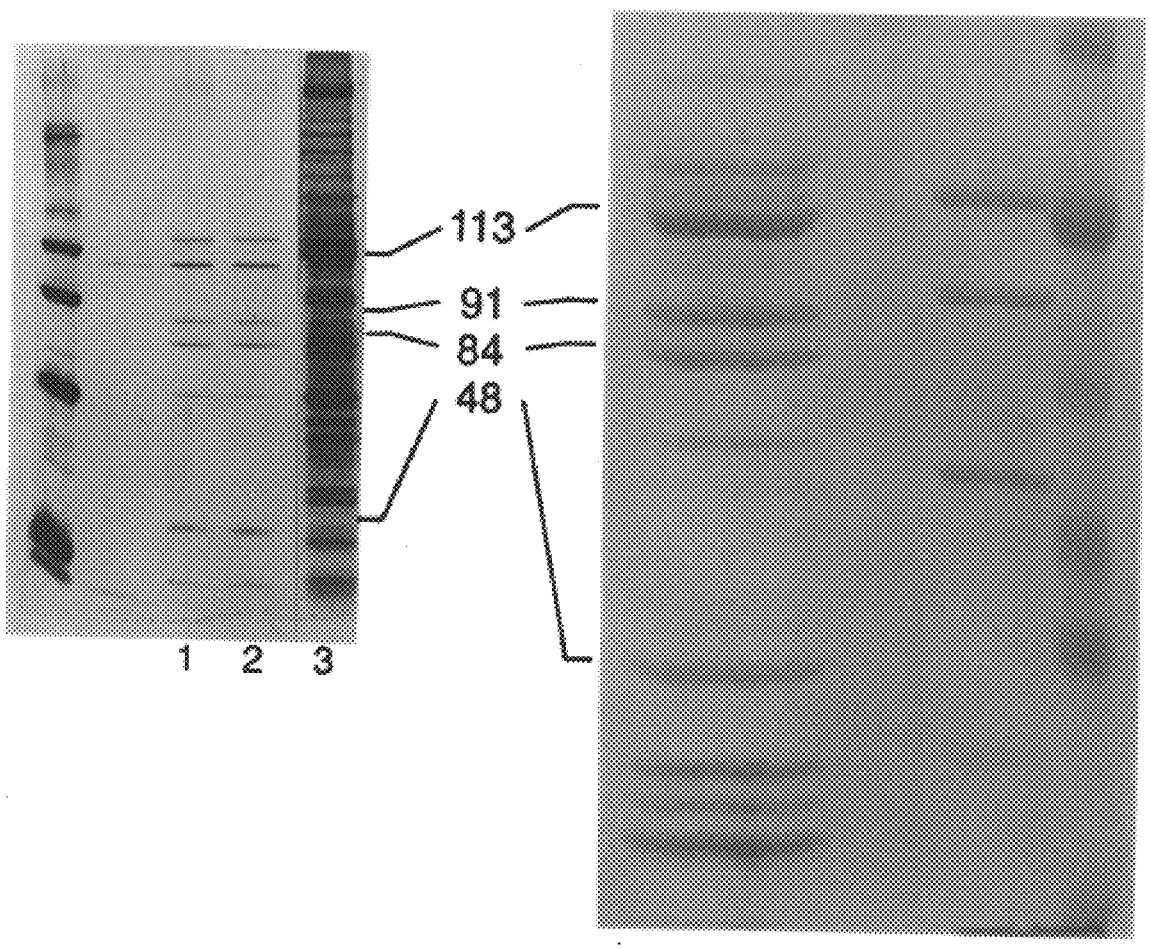
FIG. 4 shows the purification of ISGF-3. The left-hand portion of the Figure shows the purification of ISGF-3 demonstrating the polypeptides present after the first oligonucleotide affinity column (lane 3) and two different preparations after the final chromatography step (Lanes 1 and 2). The left most lane contains protein size markers (High molecular weight, Sigma). ISGF-3 component proteins are indicated as 113 kD, 91 kD, 84 kD, and 48 kD Kessler et al., *GENES & DEV.*, 4 (1990); Levy et al., *THE EMBO. J.*, 9 (1990)]. The right-hand portion of the Figure shows purified ISGF-3 from 2–3×10$^{11}$ cells was electroblotted to nitrocellulose after preparations 1 and 2 (Lanes 1 and 2) had been pooled and separated on a 7.5% SDS polyacrylamide gel. ISGF-3 component proteins are indicated. The two lanes on the right represent protein markers (High molecular weight, and prestained markers, Sigma).

Antibodies a42, a55 and a57 were prepared by injecting approximately 500 mgm of a fusion protein prepared in *E. coli* using the GE3-3X vector [Smith et al., GENE, 67 (1988)]. Rabbits were bled after the second boost and serum prepared.

For Western blots highly purified ISGF-3 was separated on a 7% SDS polyacrylamide gel and electroblotted to nitrocellulose. The filter was incubated in blocking buffer ("blotto"), cut into strips and probed with specific antiserum and preimmune antiserum diluted 1:500. The immune complexes were visualized with the aid of an ECL kit (Amersham). Shift analyses were performed as previously described [Levy et al., GENES & DEV., 2 (1988); Levy et al., GENES & DEV., 3 (1989)] in a 4.5% polyacrylamide gel.

FIG. 8 parts A and B present the full length amino acid sequence of 113 kD protein components of ISGF-3α (SEQ ID NO:2) and alignment of conserved amino acid sequences between the 113 kD and 91/84 kD proteins (SEQ ID NOS:4 AND 6).
 A. Polypeptide sequences (A–E) derived from protein micro-sequencing of purified 113 kD protein (see accompanying paper) are underlined. Based on peptide E, we designed a degenerate oligonucleotide, AAT/CACIGAA/GCCIATGGAA/GATT/CATT (SEQ ID NO:13), which was used to screen a cDNA library [Pine et la., MOL. CELL. BIOL., 10 (1990)] basically as described [Norman et al., CELL, 55 (1988)]. Briefly, the degenerate oligonucleotides were labeled by 32P-γ-ATP by polynucleotide kinase, hybridizations were carried out overnight at 40° C. in 6×SSTE (0.9M NaCl, 60 mM Tris-HCl [pH 7.9] 6 mM EDTA), 0.1% SDS, 2 mM $Na_2P_5O_7$, 6 mM $KH_2PO_4$ in the presence of 100 mg/ml salmon sperm DNA sperm and 10×Denhardt's solution [Maniatis et al., MOLECULAR CLONING; A LABORATORY MANUAL (Cold Spring Harbor Lab., 1982)]. The nitrocellulose filters then were washed 4×10 min. with the same hybridization conditions without labeled probe and salmon sperm DNA. Autoradiography was carried out at −80° C. with intensifying screen for 48 hrs. A PCR product was obtained later by the same method described for the 91/84 kD sequences, by using oligonucleotides designed according polypeptide D and E. The sequence of this PCR product was identical to a region in clone f11. The full length of 113 kD protein contains 851 amino acids. Three major helices in the N-terminal region were predicted by the methods of both Chou and Fasman [Chou et al., ANN. REV. BIOCHEM., 47 (1978)] and Garnier et al [Garnier et al., J. MOL. BIOL., 12 (1978)] and are shown in shadowed boxes. At the C-terminal end, a highly negative charged domain was found. All negative charged residues are blackened and positive charged residues shadowed. The five polypeptides that derived from protein microscreening [Aebersold et al., PROC. NATL. ACAD. SCI. USA, 87 (1987)] are underlined.
 B) Comparison of amino acid sequences of 113 kD and 91/84 kD protein shows a 42% identical amino acid residues in the overlapping 715 amino acid sequence shown. In the middle helix region four leucine and one valine heptad repeats were identified in both 113 and 91/84 kD protein (the last leucine in 91/84 kD is not exactly preserved as heptad repeats). When a heligram structure was drawn this helix is amphipathic (not shown). Another notable feature of this comparison is several tyrosine residues that are conserved in both proteins near their ends.

FIG. 9 parts A and B show the in vitro transcription and translation of 113 kD and 91 kD cDNA and a Northern blot analysis with 113 kD cDNA probe.
 a) The full length cDNA clones of 113 and 91 kD protein were transcribed in vitro and transcribed RNAs was translated in vitro with rabbit lenticulate lysate (Promega; conditions as described in the Promega protocol). The mRNA of BMV (Promega) was simultaneously translated as a protein size marker. The 113 cDNA yielded a translated product about 105 kD and the 91 cDNA yielded a 86 kD product.
 b) When total cytoplasmic mRNAs isolated from superinduced HeLa cells were utilized, a single 4.8 KB mRNA band was observed with a cDNA probe coding for C-end of 113 kD protein in a Northern blot analysis [Nielsch et al., The EMBO. J., 10 (1991)].

FIG. 10(A) presents the results of Western blot analysis confirming the identity of the 113 kD protein. An antiserum raised against a polypeptide segment [Harlow et al., ANTIBODIES; A LABORATORY MANUAL (Cold Spring Harbor Lab., 1988)] from amino acid 500 to 650 of 113 kD protein recognized specifically a 113 kD protein in a protein Western blot analysis. The antiserum recognized a band both in a highly purified ISGF-3 fraction (>10,000 fold) from DNA affinity chromatography and in the crude extracts prepared from γ and α IFN treated HeLa cells [Fu et al., PROC. NATL. ACAD. SCI. USA, 87 (1990)]. The antiserum was raised against a fusion protein [a cDNA fragment coding for part of 113 kD protein was inserted into pGEX-2T, a high expression vector in the *E. coli* [Smith et al., PROC. NATL. ACAD. SCI. USA, 83 (1986)] purified from *E. coli* [Smith et al., GENE, 67 (1988)]. The female NZW rabbits were immunized with 1 mg fusion protein in Freund's adjuvant. Two subsequent boosts two weeks apart were carried out with 500 mg fusion protein. The Western blot was carried out with conditions described previously [Pine et al., MOL. CELL. BIOL., 10 (1990)].

FIG. 10(B) presents the results of a mobility shift assay showing that the anti-113 antiserum affects the ISGF-3 shift complex. Preimmune serum or the 113 kD antiserum was added to shift reaction carried out as described [Fu et al. PROC. NATL. ACAD. SCI. USA, 87 (1990); Kessler et al. GENES & DEV., 4, (1990)] at room temperature for 20 min. then one-third of reaction material was loaded onto a 5% polyacrylamide gel. In addition unlabeled probe was included in one reaction to show specificity of the gel shift complexes.

Figure 11:
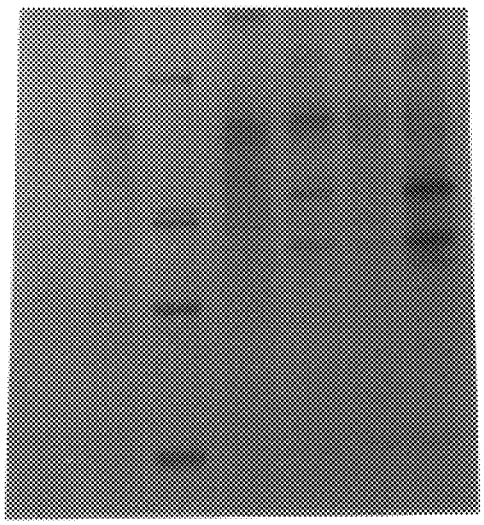

FIG. 11 shows the results of experiments investigating the IFN-α dependent phosphorylation of 113, 91 and 84 kD proteins. Protein samples from cells treated in various ways after 60 min. exposure to $^{32}PO_4^{-3}$ were precipitated with antiserum to 113 kD protein. Lane 1, no treatment of cells; Lane 2, cells treated 7 min. with IFN-α. By comparison with the marker proteins labeled 200, 97.5, 69 and 46 kD (kilo daltons), the $PO_4^{-3}$ labeled proteins in the precipitate are seen to be 113 and 91 kD. Lane 3, cells treated with IFN-γ overnight (no phosphorylated proteins) and then (Lane 4) treated with IFN-α for 7 min. show heavier phosphorylation of 113, 91 and 84 kD.

Figure 12:
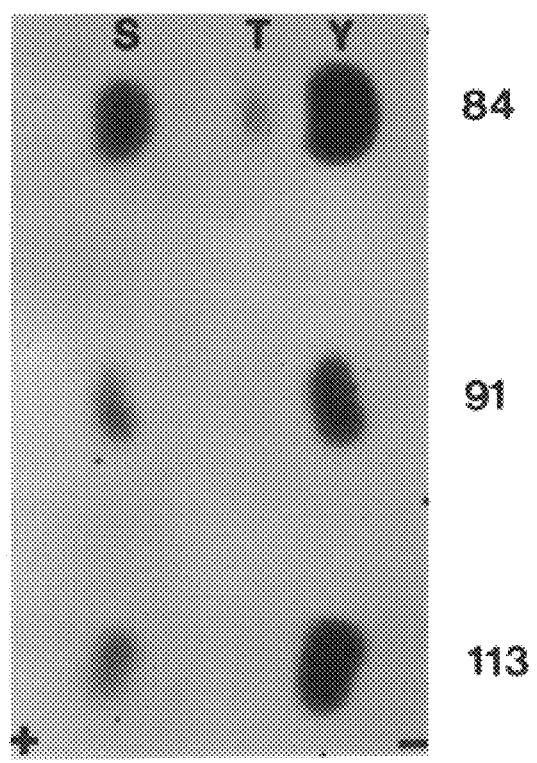

FIG. 12 is a chromatogram depicting the identification of phosphoamino acid. Phosphate labeled protein of 113, 91 or 84 kD size was hydrolyzed and chromatographed to reveal newly labeled phosphotyrosine. Cells untreated with IFN showed only phosphoserine label. (P Ser=phosphoserine; P Thr=phosphothreonine; P Tyr=phosphotyrosine.

FIG. 13 parts A–C depict (A) the deduced amino acid sequence (SEQ ID NO:8) of and (B–C) the DNA sequence (SEQ ID NO:7) encoding the murine 91 kD intracellular receptor recognition factor.

FIG. 14 parts A–D depict (A) the deduced amino acid sequence (SEQ ID NO:10) of and (B–D) the DNA sequence (SEQ ID NO:9) encoding the 13sf1 intracellular receptor recognition factor.

FIG. 15 parts A–E depict (A) the deduced amino acid sequence (SEQ ID NO:12) of and (B–E) the DNA sequence (SEQ ID NO:11) encoding the 19sf6 intracellular receptor recognition factor.

FIGS. 16A–D. Determination of molecular weights of Stat91 and phospho Stat91 by native gel analysis.

A) Western blot analysis of fractions from affinity purification. Extracts from human FS2 fibroblasts treated with IFN-γ (Ext), the unbound fraction (Flow), the fraction washed with Buffer AO.2 (AO.2), and the bound fraction eluted with buffer AO.8 (AO.8) were immunoblotted with anti-91T.

B) Native gel analysis. Phosphorylated Stat91 (the AO.8 fraction from A) and unphosphorylated Stat91 (the Flow fraction from A) were analyzed on 4.5%, 5.5%, 6.5% and 7.5% native polyacrylamide gels followed by immunoblotting with anti-91T. The top of gels (TOP) and the migration position of bromophenol blue (BPB) are indicated.

C) Ferguson plots. The relative mobilities (Rm) of the Stat91 and phospho Stat91 were obtained from FIG. 1B (see Experimental Procedures). Closed circle: Chicken egg albumin (45 kD); Cross: Bovine serum albumin, monomer (66 kD); Open square: Bovine serum albumin, dimer (132 kD); Open circle: Urease, trimer (272 kD); Open triangle: Unphosphorylated Stat91; Closed triangle: Phosphorylated Stat91.

D) Determination of molecular weights from the standard curve. The molecular weights of phosphorylated and unphosphorylated Stat91 proteins (indicated as closed and open arrows, respectively) were obtained by extrapolation of their retardation coefficients.

Figure 17A:
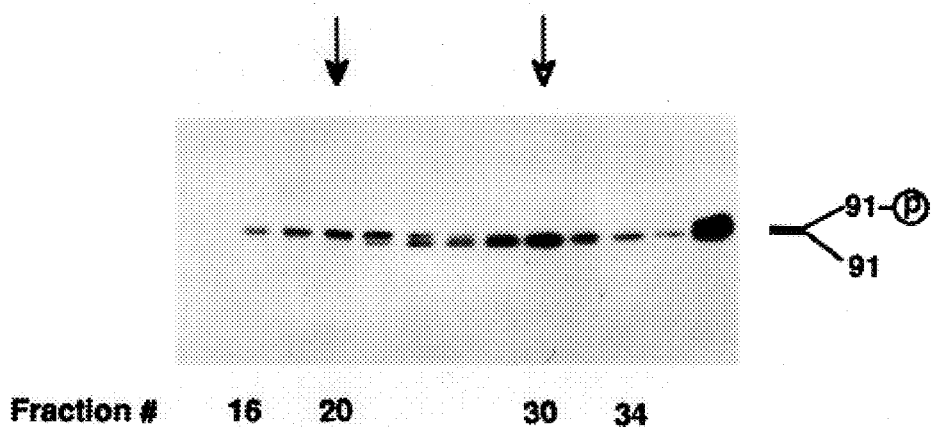
Figure 17B:
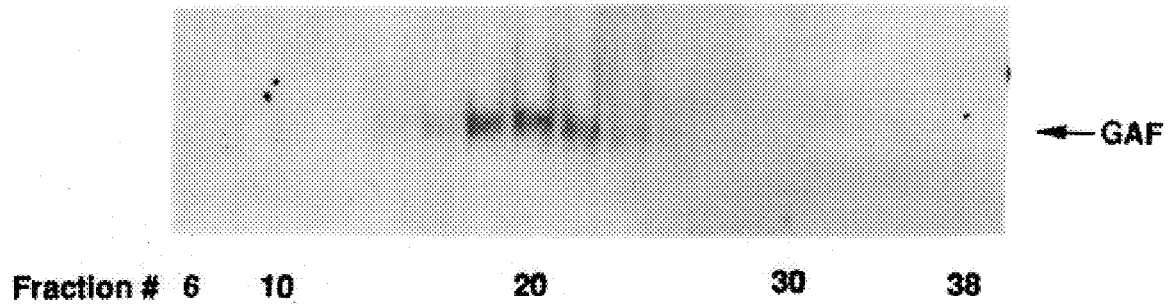
Figure 17C:
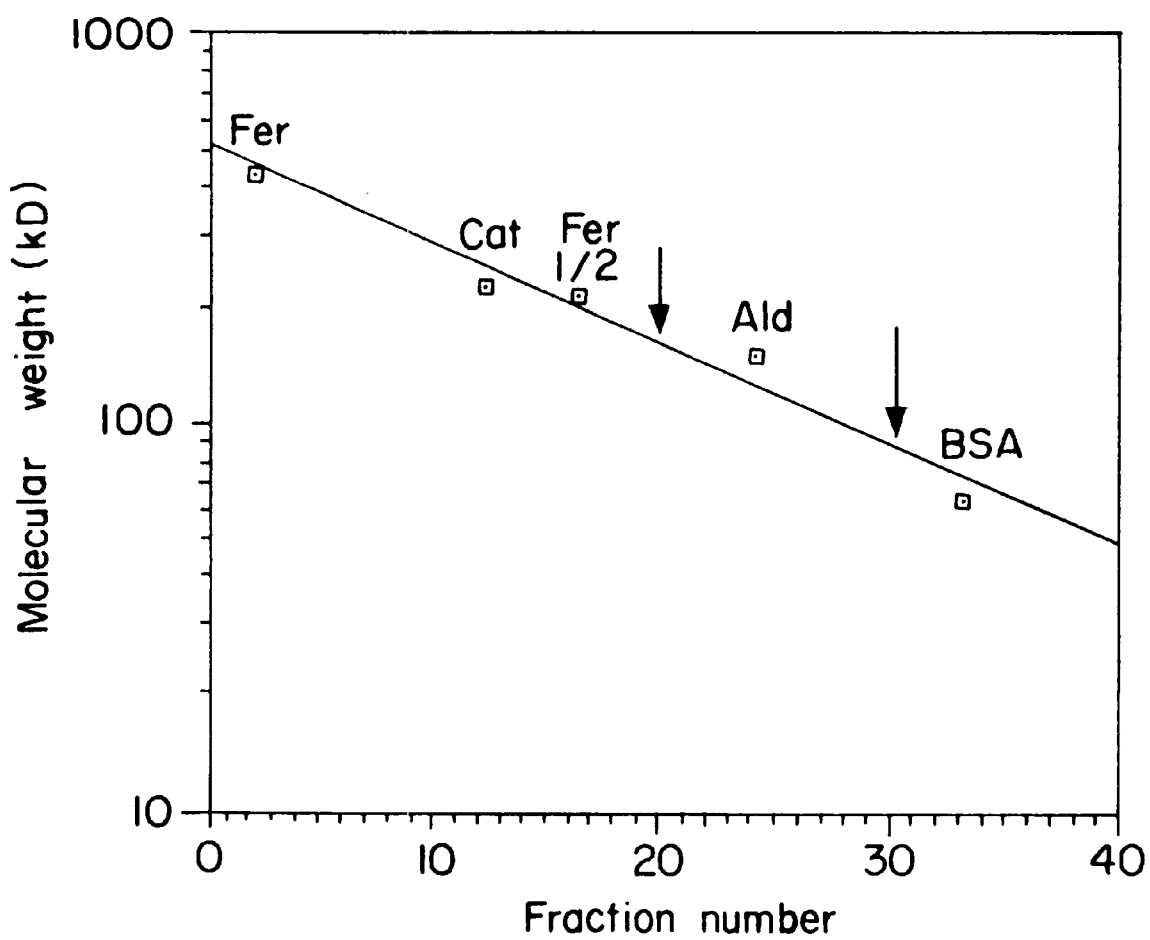

FIGS. 17A–C. Determination of molecular weights by glycerol gradients.

A) Western blot analysis. Extracts from human Bud8 fibroblasts treated with IFN-γ (the rightmost lane) and every other fraction from fraction 16 to 34 were analyzed on 7.5% SDS-PAGE followed by immunoblotting with anti-91T. The peak of phosphorylated Stat91 (fraction 20) and the peak of unphosphorylated Stat91 (fraction 30) were indicated by a closed and open arrow, respectively.

B) Mobility shift analysis. Every other fractions from the gradients were analyzed.

C) Graphic representation of the data from A and B. Peak fraction numbers of protein standards are plotted versus their molecular weight. The position of peaks (of phosphorylated and unphosphorylated Stat91 protein are indicated by the closed and open arrows, respectively. Standards are ferritin (Fer, 440 kD), catalase (Cat, 232 kD), ferritin half unit (Fer 1/2, 220 kD), aldolase (Ald, 158 kD), bovine serum albumin (BSA, 68 kD).

Figure 18A:
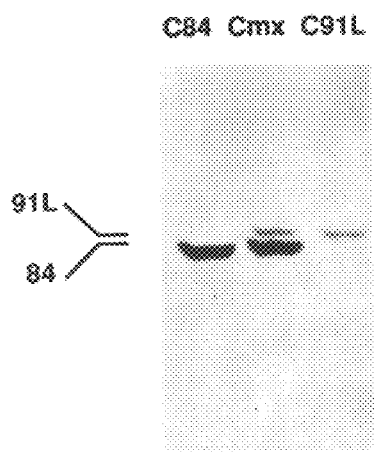
Figure 18B:
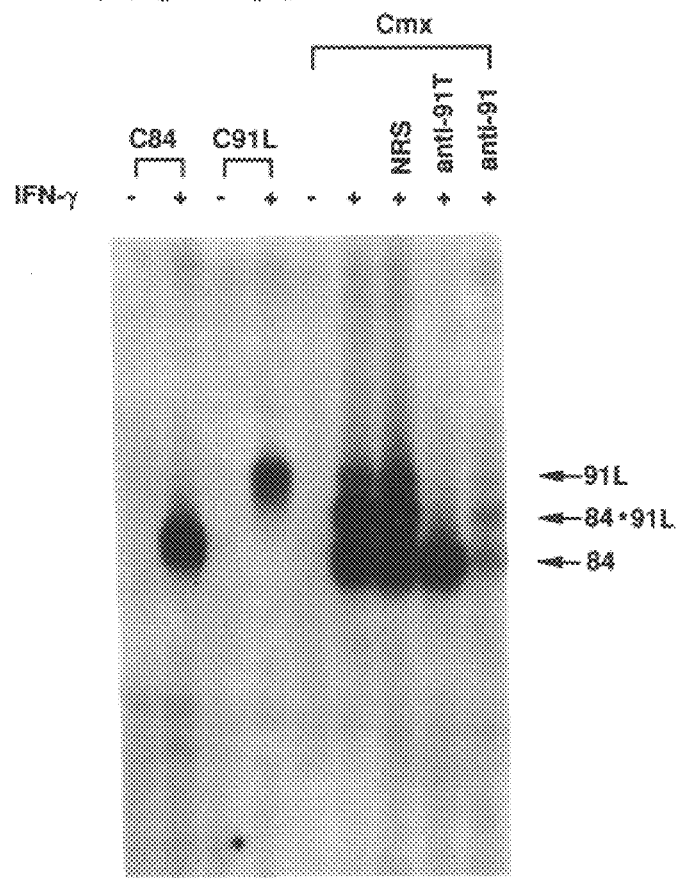

FIGS. 18A–B. Stat91 in cell extracts binds DNA as a dimer.

A) Wester blot analysis. Extracts from stable cell lines expressing either Stat84 (C84), or Stat91L (C91L) or both (Cmx) were analyzed on 7.5% SDS-PAGE followed by immunobloting with anti-91.

B) Gel mobility shift analysis. Extracts from stable cell lines (FIG. 3A) untreated (−) or treated with IFN-γ(+) were analyzed. The positions of Stat91 homodimer (91L), Stat84 homodimer (84), and the heterodimer (84*91) are indicated.

Figure 19:
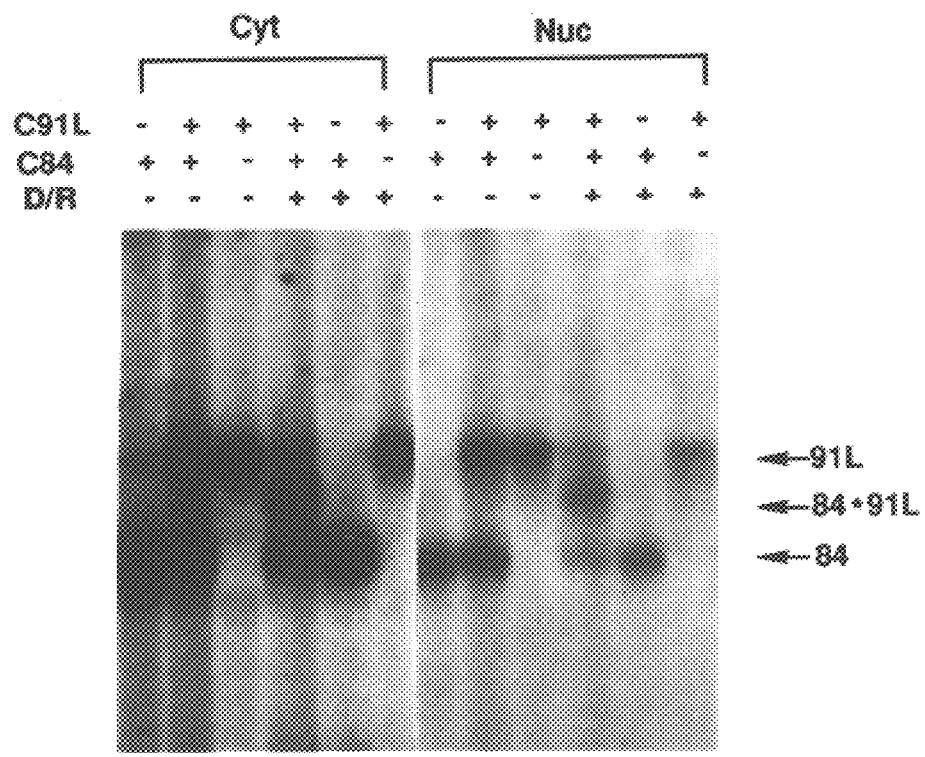

FIG. 19. Formation of herterodimer by denaturation and renaturation. Cytoplasmic (Left Panel) or nuclear extracts (Right Panel) from IFN-γ-treated cell lines expressing either Stat84 (C84) or Stat91 (C91) were analyzed by gel mobility shift assays. +: with addition; −: without addition; D/R: samples were subjected to guanidinium hydrochloride denaturation and renaturation treatment.

Figure 20:
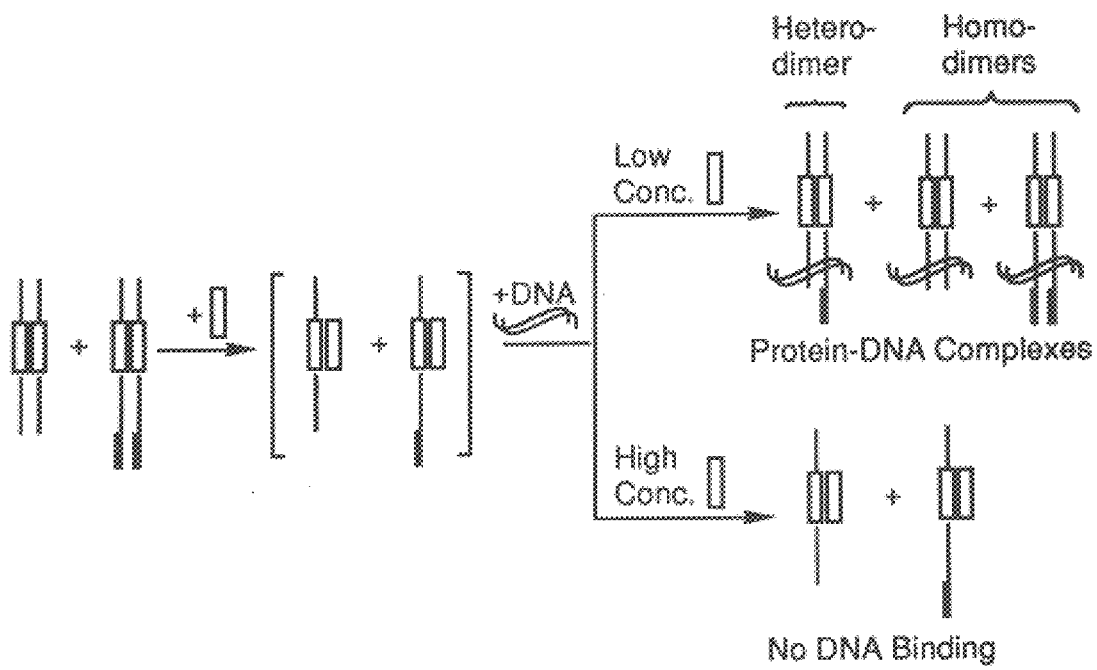

FIG. 20. Diagramatic representation of dissociation and reassociation analysis.

Figure 21:
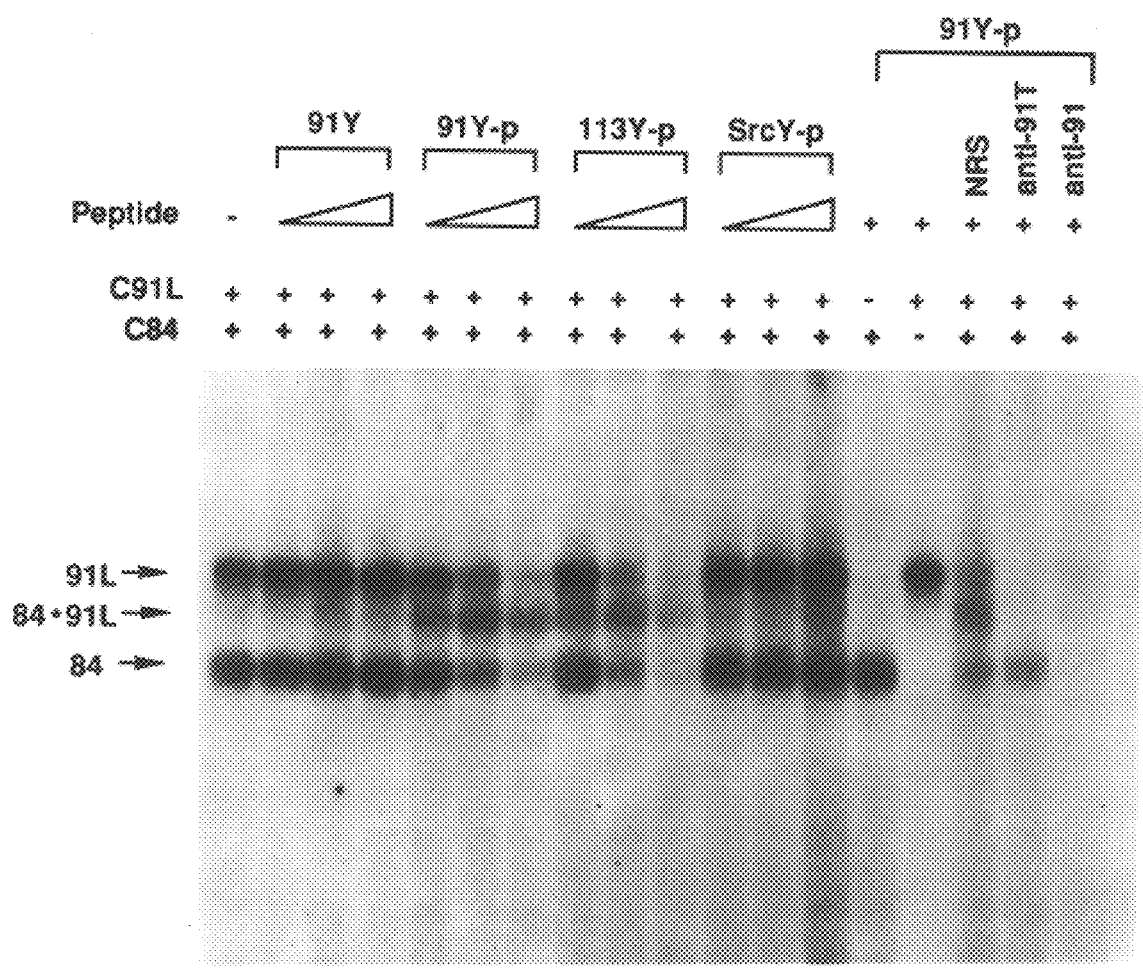

FIG. 21. Dissociation-reassociation analysis with peptides. Gel mobility shift analysis with IFN-γ treated nuclear extracts from cell lines expressing Stat91L (C91L, lane 15) or Stat84 (C84, lane 14) or mixture of both (lane 1–13, 16–18) in the presence of increasing concentrations of various peptides. 91-Y, unphosphorylated peptide from Stat91 (LDGPKGTGYIKTELI) (SEQ. ID NO.:18); 91Y-p, phosphotyrosyl peptide from Stat91 (GY*IKTE) (SEQ ID NO.:19); 113Y-p, phosphotyrosyl peptide with high binding affinity to Src SH2 domain (EPQY*EEIPIYL, Songyang et al., 1993, Cell 72: 767–778) (SEQ. ID NO.:21). Final concentrations of peptides added: 1 μM (lane 8), 4 μM (lane 2,5, 11), 10 μM (lane 9), 40 μM (lane 3, 6, 10, 12, 14–18), 160 μM (lane 4, 7, 13). +: with addition; −: without addition. Right panel: antiserum tests for identity of gel-shift bands (see FIG. 3).

Figure 22A:
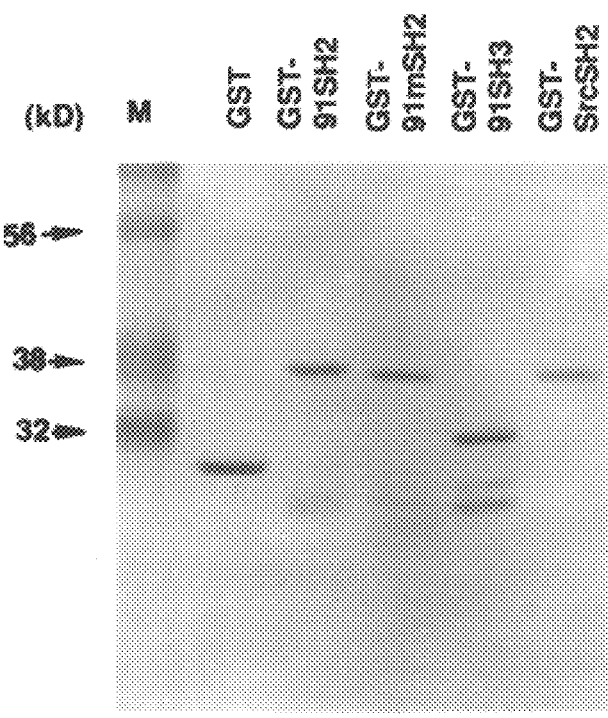

FIG. 22. parts A and B: Dissociation-reassociation analysis with GST fusion proteins. A) SDS-PAGE (12%) analysis of purified GST fusion proteins as visualized by Commasie blue. GST-91 SH3, native SH2 domain of Stat91; GST-91 mSH2, $R^{602}$ to $L^{602}$ mutant; GST-91 SH3, SH3 domain of Stat91; GST Src SH2, the SH2 domain of src protein. Same amounts (1 μg) of each fusion proteins were loaded. Protein markers were run in lane 1 as indicated.

B) Dissociation-reassociation analysis similar to FIG. 6. Dissociating agents were GST fusion proteins purified from bacterial expression as shown above. Final concentrations of fusion proteins added are 0.5 μM (lanes 2, 5, 8, 11, 14), 2.5 μM (lanes 3, 6, 9, 12, 15) and 5 μM (lanes 4, 7, 10, 13, 17, 18). +: with addition; −: without addition; FP: fusion proteins.

FIGS. 23A and 23B. Comparison of Stat91 SH2 structure with known SH2 structures. The Stat91 sequence is disclosed herein (SEQ ID NO:4). The structures used for the other SH2s are Src (Waksman et al., 1992, Nature 358: 646–653) (SEQ ID NO:22), AbI (Overduin et al., 1992, Proc. Natl. Acad. Sci. USA 89: 11673–77 and 1992, Cell 70: 697–704) (SEQ ID NO:23, Lck (Eck et al., 1993, Nature 362: 87–91) (SEQ ID NO:24), and p85αN (Booker et al., 1992, Nature 358: 684–687) (SEQ ID NO:25). The alignment of the determined structures is by direct coordinate superimposition of the backbone structures. The names of secondary structural features and significant residues is based on the scheme of Eck et al., 1993. The boundaries and extents of the structure features are indicated by [- - -]. The starting numbers for the parent sequences are shown in parentheses. Experimentally determined structurally conserved regions are from Src, p85α, and AbI (Cowburn, unpublished). The root mean square deviation of three-dimensionally aligned structures differs by less than 1 Angstrom for the backbone non-hydrogen atoms in the sections marked by the XXX.

DETAILED DESCRIPTION

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual" (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Therefore, if appearing herein, the following terms shall have the definitions set out below.

The terms "receptor recognition factor", "receptor recognition-tyrosine kinase factor", "receptor recognition factor/tyrosine kinase substrate", "receptor recognition/transcription factor", "recognition factor" and "recognition factor protein(s)" and any variants not specifically listed, may be used herein interchangeably, and as used throughout the present application and claims refer to proteinaceous material including single or multiple proteins, and extends to those proteins having the amino acid sequence data described herein and presented in FIG. 1 (SEQ ID NO:2), FIG. 2 (SEQ ID NO:4) and in FIG. 3 (SEQ ID NO:6), and the profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "receptor recognition factor", "recognition factor" and "recognition factor protein(s)" are intended to include within their scope proteins specifically recited herein as well as all substantially homologous analogs and allelic variations.

The amino acid residues described herein are preferred to be in the "L" isomeric form. However, residues in the "D" isomeric form can be substituted for any L-amino acid residue, as long as the desired fuctional property of immunoglobulin-binding is retained by the polypeptide. NH2 refers to the free amino group present at the amino terminus of a polypeptide. COOH refers to the free carboxy group present at the carboxy terminus of a polypeptide. In keeping with standard polypeptide nomenclature, *J. Biol. Chem.*, 243: 3552–59 (1969), abbreviations for amino acid residues are shown in the following Table of Correspondence:

| TABLE OF CORRESPONDENCE | | |
|---|---|---|
| SYMBOL 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino)

terminus and a translation stop codon at the 3' (carboxyl) terminus. A coding sequence can include, but is not limited to, prokaryotic sequences, cDNA from eukaryotic MRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes. The term "oligonucleotide", as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an intifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 30 percent, more preferably by at least 50 percent, most preferably by at least 90 percent, a clinically significant change in the S phase activity of a target cellular mass, or other feature of pathology such as for example, elevated blood pressure, fever or white cell count as may attend its presence and activity.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash.

In its primary aspect, the present invention concerns the identification of a receptor recognition factor, and the isolation and sequencing of a particular receptor recognition factor protein, that is believed to be present in cytoplasm and that serves as a signal transducer between a particular cellular receptor having bound thereto an equally specific polypeptide ligand, and the comparably specific transcription factor that enters the nucleus of the cell and interacts with a specific DNA binding site for the activation of the gene to promote the predetermined response to the particular polypeptide stimulus. The present disclosure confirms that specific and individual receptor recognition factors exist that correspond to known stimuli such as tumor necrosis factor, nerve growth factor, platelet-derived growth factor and the like. Specific evidence of this is set forth herein with respect to the interferons α and γ (IFNα and IFNγ).

A further property of the receptor recognition factors (also termed herein signal transducers and activators of transcription—STAT) is dimerization to form homodimers or heterodimers upon activation by phosphorylation of tyrosine. In a specific embodiment, infra, Stat91 and Stat84 form homodimers and a Stat91–Stat84 heterodimer. Accordingly, the present invention is directed to such dimers, which can form spontaneously by phophorylation of the STAT protein, or which can be prepared synthetically by chemically cross-linking two like or unlike STAT proteins.

The present receptor recognition factor is likewise noteworthy in that it appears not to be demonstrably affected by fluctuations in second messenger activity and concentration. The receptor recognition factor proteins appear to act as a substrate for tyrosine kinase domains, however do not appear to interact with G-proteins, and therefore do not appear to be second messengers.

A particular receptor recognition factor identified herein by SEQ ID NO:4, has been determined to be present in cytoplasm and serves as a signal transducer and a specifice transcription factor in response to IFN-γ stimulation that enters the nucleus of the cell and interacts directly with a specific DNA binding site for the activation of the gene to promote the predetermined response to the particular polypeptide stimulus. This particular factor also acts as a translation protein and, in particular, as a DNA binding protein in response to interferon-γ stimulation. This factor is likewise noteworthy in that it has the following characteristics:

a) It interacts with an interferon-γ-bound receptor kinase complex;

b) It is a tyrosine kinase substrate; and c) When phosphorylated, it serves as a DNA binding protein.

More particularly, the factor of SEQ ID NO:4 directly interacts with DNA after acquiring phosphate on tyrosine located at position 701 of the amino acid sequence. Also, interferon-γ-dependent activation of this factor occurs without new protein synthesis and appears within minutes of interferon-γ treatment, achieves maximum extent between 15 and 30 minutes thereafter, and then disappears after 2–3 hours.

In a particular embodiment, the present invention relates to all members of the herein disclosed family of receptor recognition factors except the 91 kD protein factors, specifically the proteins whose sequences are represented by one or more of SEQ ID NO:4, SEQ ID NO:6 or SEQ ID NO:8.

Subsequent to the filing of the initial applications directed to the present invention, the inventors have termed each member of the family of receptor recognition factors as a signal transducer and activator of transcription (STAT) protein. Each STAT protein is designated by the apparent molecular weight (e.g., Stat113, Stat91, Stat84, etc.), or by the order in which it has been identified (e.g., Stat1α [Stat91], Stat1β [Stat84], Stat2 [Stat113], Stat3 [a murine protein described in U.S. application Ser. No. 08/126,588, filed Sep. 24, 1993 as 19sf6], and Stat4 [a murine STAT protein described in U.S. application Ser. No. 08/126,588, filed Sep. 24, 1993 as 13sf1]). As will be readily appreciated by one of ordinary skill in the art, the choice of name has no effect on the intrinsic characteristics of the factors described herein, which were first disclosed in U.S. application Ser. No. 07/845,296, filed Mar. 19, 1992. The present inventors have chosen to adopt this newly derived terminology herein as a convenience to the skilled artisan who is familiar with the subsequently published papers relating to the same, and in accordance with the proposal to harmonize the terminology for the novel class of proteins, and nucleic acids encoding the proteins, disclosed by the instant inventors. The terms [molecular weight] kd receptor recognition factor, Stat[molecular weight], and Stat[number] are used herein interchangeably, and have the meanings given above. For example, the terms 91 kd protein, Stat91, and Statla refer to the same protein, and in the appropriate context refer to the nucleic acid molecule encoding such protein.

As stated above, the present invention also relates to a recombinant DNA molecule or cloned gene, or a degenerate variant thereof, which encodes a receptor recognition factor, or a fragment thereof, that possesses a molecular weight of about 113 kD and an amino acid sequence set forth in FIG. 1 (SEQ ID NO:2); preferably a nucleic acid molecule, in particular a recombinant DNA molecule or cloned gene, encoding the 113 kD receptor recognition factor has a nucleotide sequence or is complementary to a DNA sequence shown in FIG. 1 (SEQ ID NO:1). In another embodiment, the receptor recognition factor has a molecular weight of about 91 kD and the amino acid sequence set forth in FIG. 2 (SEQ ID NO:4) or FIG. 13 (SEQ ID NO:8); preferably a nucleic acid molecule, in particular a recombinant DNA molecule or cloned gene, encoding the 91 kD receptor recognition factor has a nucleotide sequence or is complementary to a DNA sequence shown in FIG. 2 (SEQ ID NO:3) or FIG. 13 (SEQ ID NO:8). In yet a further embodiment, the receptor recognition factor has a molecular weight of about 84 kD and the amino acid sequence set forth in FIG. 3 (SEQ ID NO:6); preferably a nucleic acid molecule, in particular a recombinant DNA molecule or cloned gene, encoding the 84 kD receptor recognition factor has a nucleotide sequence or is complementary to a DNA sequence shown in FIG. 3 (SEQ ID NO:5). In yet another embodiment, the receptor recognition factor has an amino acid sequence set forth in FIG. 14 (SEQ ID NO:10); preferably a nucleic acid molecule, in particular a recombinant DNA molecule or cloned gene, encoding such receptor recognition factor has a nucleotide sequence or is complementary to a DNA sequence shown in FIG. 14 (SEQ ID NO:9). In still another embodiment, the receptor recognition factor has an amino acid sequence set forth in FIG. 15 (SEQ ID NO:12); preferably a nucleic acid molecule, in particular a recombinant DNA molecule or cloned gene, encoding such receptor recognition factor has a nucleotide sequence or is complementary to a DNA sequence shown in FIG. 15 (SEQ ID NO:11).

The possibilities both diagnostic and therapeutic that are raised by the existence of the receptor recognition factor or factors, derive from the fact that the factors appear to participate in direct and causal protein-protein interaction between the receptor that is occupied by its ligand, and those factors that thereafter directly interface with the gene and effect transcription and accordingly gene activation. As suggested earlier and elaborated further on herein, the present invention contemplates pharmaceutical intervention in the cascade of reactions in which the receptor recognition factor is implicated, to modulate the activity initiated by the stimulus bound to the cellular receptor.

Thus, in instances where it is desired to reduce or inhibit the gene activity resulting from a particular stimulus or factor, an appropriate inhibitor of the receptor recognition factor could be introduced to block the interaction of the receptor recognition factor with those factors causally connected with gene activation. Correspondingly, instances where insufficient gene activation is taking place could be remedied by the introduction of additional quantities of the receptor recognition factor or its chemical or pharmaceutical cognates, analogs, fragments and the like.

As discussed earlier, the recognition factors or their binding partners or other ligands or agents exhibiting either mimicry or antagonism to the recognition factors or control over their production, may be prepared in pharmaceutical compositions, with a suitable carrier and at a strength effective for administration by various means to a patient experiencing an adverse medical condition associated specific transcriptional stimulation for the treatment thereof. A variety of administrative techniques may be utilized, among them parenteral techniques such as subcutaneous, intravenous and intraperitoneal injections, catheterizations and the like. Average quantities of the recognition factors or their subunits may vary and in particular should be based upon the recommendations and prescription of a qualified physician or veterinarian.

Also, antibodies including both polyclonal and monoclonal antibodies, and drugs that modulate the production or activity of the recognition factors and/or their subunits may possess certain diagnostic applications and may for example, be utilized for the purpose of detecting and/or measuring conditions such as viral infection or the like. For example, the recognition factor or its subunits may be used to produce both polyclonal and monoclonal antibodies to themselves in a variety of cellular media, by known techniques such as the hybridoma technique utilizing, for example, fused mouse spleen lymphocytes and myeloma cells. Likewise, small molecules that mimic or antagonize the activity(ies) of the receptor recognition factors of the invention may be discovered or synthesized, and may be used in diagnostic and/or therapeutic protocols.

The general methodology for maling monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Panels of monoclonal antibodies produced against recognition factor peptides can be screened for various properties; i.e., isotype, epitope, affinity, etc. Of particular interest are monoclonal antibodies that neutralize the activity of the recognition factor or its subunits. Such monoclonals can be readily identified in recognition factor activity assays. High affinity antibodies are also useful when immunoaffinity purification of native or recombinant recognition factor is possible.

Preferably, the anti-recognition factor antibody used in the diagnostic methods of this invention is an affinity purified polyclonal antibody. More preferably, the antibody is a monoclonal antibody (mAb). In addition, it is preferable for the anti-recognition factor antibody molecules used herein be in the form of Fab, Fab', F(ab')$_2$ or F(v) portions of whole antibody molecules.

As suggested earlier, the diagnostic method of the present invention comprises examining a cellular sample or medium by means of an assay including an effective amount of an antagonist to a receptor recognition factor/protein, such as an anti-recognition factor antibody, preferably an affinity-purified polyclonal antibody, and more preferably a mAb. In addition, it is preferable for the anti-recognition factor antibody molecules used herein be in the form of Fab, Fab', F(ab')$_2$ or F(v) portions or whole antibody molecules. As previously discussed, patients capable of benefiting from this method include those suffering from cancer, a precancerous lesion, a viral infection or other like pathological derangement. Methods for isolating the recognition factor and inducing anti-recognition factor antibodies and for determining and optimizing the ability of anti-recognition factor antibodies to assist in the examination of the target cells are all well-known in the art.

Methods for producing polyclonal anti-polypeptide antibodies are well-known in the art. See U.S. Pat. No. 4,493,795 to Nestor et al. A monoclonal antibody, typically containing Fab and/or F(ab')$_2$ portions of useful antibody molecules, can be prepared using the hybridoma technology described in *Antibodies—A Laboratory Manual*, Harlow and Lane, eds., Cold Spring Harbor Laboratory, New York (1988), which is incorporated herein by reference. Briefly, to form the hybridoma from which the monoclonal antibody composition is produced, a myeloma or other self-perpetuating cell line is fused with lymphocytes obtained from the spleen of a mammal hyperimmunized with a recognition factor-binding portion thereof, or recognition factor, or an origin-specific DNA-binding portion thereof.

Splenocytes are typically fused with myeloma cells using polyethylene glycol (PEG) 6000. Fused hybrids are selected by their sensitivity to HAT. Hybridomas producing a monoclonal antibody useful in practicing this invention are identified by their ability to immunoreact with the present recognition factor and their ability to inhibit specified transcriptional activity in target cells.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM; Dulbecco et al., *Virol* 8: 396 (1959)) supplemented with 4.5 gm/1 glucose, 20 mm glutamine, and 20% fetal calf serum. An exemplary inbred mouse strain is the Balb/c.

Methods for producing monoclonal anti-recognition factor antibodies are also well-known in the art. See Niman et al., *Proc. Natl. Acad. Sci. USA*, 80: 4949–4953 (1983). Typically, the present recognition factor or a peptide analog is used either alone or conjugated to an immunogenic carrier, as the immunogen in the before described procedure for producing anti-recognition factor monoclonal antibodies. The hybridomas are screened for the ability to produce an antibody that immunoreacts with the recognition factor peptide analog and the present recognition factor.

The present invention further contemplates therapeutic compositions useful in practicing the therapeutic methods of this invention. A subject therapeutic composition includes, in admixture, a pharmaceutically acceptable excipient (carrier) and one or more of a receptor recognition factor, polypeptide analog thereof or fragment thereof, as described herein as an active ingredient. In a preferred embodiment, the composition comprises an antigen capable of modulating the specific binding of the present recognition factor within a target cell.

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide-, analog- or active fragment-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition or neutralization of recognition factor binding capacity desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

The therapeutic compositions may further include an effective amount of the factor/factor synthesis promoter antagonist or analog thereof, and one or more of the following active ingredients: an antibiotic, a steroid. Exemplary formulations are given below:

| Formulations | |
|---|---|
| Ingredient | mg/ml |
| Intravenous Formulation I | |
| cefotaxime | 250.0 |
| receptor recognition factor | 10.0 |
| dextrose USP | 45.0 |
| sodium bisulfite USP | 3.2 |
| edetate disodium USP | 0.1 |
| water for injection q.s.a.d. | 1.0 ml |
| Intravenous Formulation II | |
| ampicillin | 250.0 |
| receptor recognition factor | 10.0 |
| sodium bisulfite USP | 3.2 |
| disodium edetate USP | 0.1 |
| water for injection q.s.a.d. | 1.0 ml |
| Intravenous Formulation III | |
| gentamicin (charged as sulfate) | 40.0 |
| receptor recognition factor | 10.0 |
| sodium bisulfite USP | 3.2 |
| disodium edetate USP | 0.1 |
| water for injection q.s.a.d. | 1.0 ml |
| Intravenous Formulation IV | |
| recognition factor | 10.0 |
| dextrose USP | 45.0 |
| sodium bisulfite USP | 3.2 |
| edetate disodium USP | 0.1 |
| water for injection q.s.a.d. | 1.0 ml |
| Intravenous Formulation V | |
| recognition factor antagonist | 5.0 |
| sodium bisulfite USP | 3.2 |
| disodium edetate USP | 0.1 |
| water for injection q.s.a.d. | 1.0 ml |

As used herein, "pg" means picogram, "ng" means nanogram, "ug" or "$\mu$g" mean microgram, "mg" means milligram, "ul" or "$\mu$" mean microliter, "ml" means milliliter, "l" means liter.

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host.

Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., $E.\ coli$ plasmids col E1, PCR1, pBR322, pMB9 and their derivatives, plasmids such as RP4; phage DNAS, e.g., the numerous derivatives of phage $\lambda$, e.g., NM989, and other phage DNA, e.g., M13 and Filamentous single stranded phage DNA; yeast plasmids such as the $2\mu$ plasmid or derivatives thereof; vectors useful in eukaryotic cells, such as vectors useful in insect or mammalian cells; vectors derived from combinations of plasmids and phage DNAS, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage $\lambda$, the control regions of fd coat protein, the promoter for 3-phosphoglycerate kinase or other glycolytic enzymes, the promoters of acid phosphatase (e.g., Pho5), the promoters of the yeast $\alpha$-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of $E.\ coli$, Pseudomonas, Bacillus, Streptomyces, fungi such as yeasts, and animal cells, such as CHO, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system.

However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the DNA sequences of this invention on fermentation or in large scale animal culture.

It is further intended that receptor recognition factor analogs may be prepared from nucleotide sequences of the protein complex/subunit derived within the scope of the present invention. Analogs, such as fragments, may be produced, for example, by pepsin digestion of receptor recognition factor material. Other analogs, such as muteins, can be produced by standard site-directed mutagenesis of receptor recognition factor coding sequences. Analogs exhibiting "receptor recognition factor activity" such as small molecules, whether functioning as promoters or inhibitors, may be identified by known in vivo and/or in vitro assays.

As mentioned above, a DNA sequence encoding receptor recognition factor can be prepared synthetically rather than cloned. The DNA sequence can be designed with the appropriate codons for the receptor recognition factor amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, Nature, 292: 756 (1981); Nambair et al., Science, 223: 1299 (1984); Jay et al., J. Biol. Chem., 259: 6311 (1984).

Synthetic DNA sequences allow convenient construction of genes which will express receptor recognition factor analogs or "umuteins". Alternatively, DNA encoding muteins can be made by site-directed mutagenesis of native receptor recognition factor genes or cDNAs, and muteins can be made directly using conventional polypeptide synthesis.

A general method for site-specific incorporation of unnatural amino acids into proteins is described in Christopher J. Noren, Spencer J. Anthony-Cahill, Michael C. Griffith, Peter G. Schultz, *Science,* 244: 182–188 (April 1989). This method may be used to create analogs with unnatural amino acids.

The present invention extends to the preparation of antisense nucleotides and ribozymes that may be used to interfere with the expression of the receptor recognition proteins at the translational level. This approach utilizes antisense nucleic acid and ribozymes to block translation of a specific mRNA, either by masking that MRNA with an antisense nucleic acid or cleaving it with a ribozyme.

Antisense nucleic acids are DNA or RNA molecules that are complementary to at least a portion of a specific mRNA molecule. (See Weintraub, 1990; Marcus-Sekura, 1988.) In the cell, they hybridize to that mRNA, forming a double stranded molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into receptor recognition factor-producing cells. Antisense methods have been used to inhibit the expression of many genes in vitro (Marcus-Sekura, 1988; Hambor et al., 1988).

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it (Cech, 1988.). Because they are sequence-specific, only mRNAs with particular sequences are inactivated.

Investigators have identified two types of ribozymes, Tetrahymena-type and "hammerhead"-type. (Hasselhoff and Gerlach, 1988) Tetrahymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific MRNA species, and eighteen base recognition sequences are preferable to shorter recognition sequences.

The DNA sequences described herein may thus be used to prepare antisense molecules against, and ribozymes that cleave mRNAs for receptor recognition factor proteins and their ligands.

The present invention also relates to a variety of diagnostic applications, including methods for detecting the presence of stimuli such as the earlier referenced polypeptide ligands, by reference to their ability to elicit the activities which are mediated by the present receptor recognition factor. As mentioned earlier, the receptor recognition factor can be used to produce antibodies to itself by a variety of known techniques, and such antibodies could then be isolated and utilized as in tests for the presence of particular transcriptional activity in suspect target cells.

As described in detail above, antibody(ies) to the receptor recognition factor can be produced and isolated by standard methods including the well known hybridoma techniques. For convenience, the antibody(ies) to the receptor recognition factor will be referred to herein as $Ab_1$ and antibody(ies) raised in another species as $Ab_2$.

The presence of receptor recognition factor in cells can be ascertained by the usual immunological procedures applicable to such determinations. A number of useful procedures are known. Three such procedures which are especially useful utilize either the receptor recognition factor labeled with a detectable label, antibody $Ab_1$ labeled with a detectable label, or antibody $Ab_2$ labeled with a detectable label. The procedures may be summarized by the following equations wherein the asterisk indicates that the particle is labeled, and "RRF" stands for the receptor recognition factor:

A. $RRF^*+Ab_1=RRF^*Ab_1$

B. $RRF+Ab^*=RRFAb_1^*$

C. $RRF+Ab_1+Ab_2^*=RRFAb_1Ab_2^*$

The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" procedure, is described in U.S. Pat. Nos. RE 31,006 and 4,016,043. Still other procedures are known such as the "double antibody", or "DASP" procedure.

In each instance, the receptor recognition factor forms complexes with one or more antibody(ies) or binding partners and one member of the complex is labeled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This is because $Ab_1$ raised in one mammalian species has been used in another species as an antigen to raise the antibody $Ab_2$. For example, $Ab_2$ may be raised in goats using rabbit antibodies as antigens. $Ab_2$ therefore would be anti-rabbit antibody raised in goats. For purposes of this description and claims, $Ab_1$ will be referred to as a primary or anti-receptor recognition factor antibody, and $Ab_2$ will be referred to as a secondary or anti-$Ab_1$ antibody.

The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine and auramine. A particular detecting material is anti-rabbit antibody prepared in goats and conjugated with fluorescein through an isothiocyanate.

The receptor recognition factor or its binding partner(s) can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are Inown and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

A particular assay system developed and utilized in accordance with the present invention, is known as a receptor assay. In a receptor assay, the material to be assayed is appropriately labeled and then certain cellular test colonies are inoculated with a quantity of both the labeled and unlabeled material after which binding studies are conducted to determine the extent to which the labeled material binds to the cell receptors. In this way, differences in affinity between materials can be ascertained.

Accordingly, a purified quantity of the receptor recognition factor may be radiolabeled and combined, for example, with antibodies or other inhibitors thereto, after which binding studies would be carried out. Solutions would then be prepared that contain various quantities of labeled and unlabeled uncombined receptor recognition factor, and cell samples would then be inoculated and thereafter incubated. The resulting cell monolayers are then washed, solubilized and then counted in a gamma counter for a length of time sufficient to yield a standard error of <5%. These data are then subjected to Scatchard analysis after which observations and conclusions regarding material activity can be drawn. While the foregoing is exemplary, it illustrates the manner in which a receptor assay may be performed and utilized, in the instance where the cellular binding ability of the assayed material may serve as a distinguishing characteristic.

An assay useful and contemplated in accordance with the present invention is known as a "cis/trans" assay. Briefly, this assay employs two genetic constructs, one of which is typically a plasmid that continually expresses a particular receptor of interest when transfected into an appropriate cell line, and the second of which is a plasmid that expresses a reporter such as luciferase, under the control of a receptor/ligand complex. Thus, for example, if it is desired to evaluate a compound as a ligand for a particular receptor, one of the plasmids would be a construct that results in expression of the receptor in the chosen cell line, while the second plasmid would possess a promoter linked to the luciferase gene in which the response element to the particular receptor is inserted. If the compound under test is an agonist for the receptor, the ligand will complex with the receptor, and the resulting complex will bind the response element and initiate transcription of the luciferase gene. The resulting chemiluminescence is then measured photometrically, and dose response curves are obtained and compared to those of known ligands. The foregoing protocol is described in detail in U.S. Pat. No. 4,981,784 and PCT International Publication No. WO 88/03168, for which purpose the artisan is referred.

In a further embodiment of this invention, commercial test kits suitable for use by a medical specialist may be prepared to determine the presence or absence of predetermined transcriptional activity or predetermined transcriptional activity capability in suspected target cells. In accordance with the testing techniques discussed above, one class of such kits will contain at least the labeled receptor recognition factor or its binding partner, for instance an antibody specific thereto, and directions, of course, depending upon the method selected, e.g., "competitive", "sandwich", "DASP" and the like. The kits may also contain peripheral reagents such as buffers, stabilizers, etc.

Accordingly, a test kit may be prepared for the demonstration of the presence or capability of cells for predetermined transcriptional activity, comprising:

(a) a predetermined amount of at least one labeled immunochemically reactive component obtained by the direct or indirect attachment of the present receptor recognition factor or a specific binding partner thereto, to a detectable label;

(b) other reagents; and (c) directions for use of said kit.

More specifically, the diagnostic test kit may comprise:

(a) a known amount of the receptor recognition factor as described above (or a binding partner) generally bound to a solid phase to form an immunosorbent, or in the alternative, bound to a suitable tag, or plural such end products, etc. (or their binding partners) one of each;

(b) if necessary, other reagents; and (c) directions for use of said test kit.

In a further variation, the test kit may be prepared and used for the purposes stated above, which operates according to a predetermined protocol (e.g. "competitive", "sandwich", "double antibody", etc.), and comprises:

(a) a labeled component which has been obtained by coupling the receptor recognition factor to a detectable label;

(b) one or more additional immunochemical reagents of which at least one reagent is a ligand or an immobilized ligand, which ligand is selected from the group consisting of:

(i) a ligand capable of binding with the labeled component (a);

(ii) a ligand capable of binding with a binding partner of the labeled component (a);

(iii) a ligand capable of binding with at least one of the component(s) to be determined; and (iv) a ligand capable of binding with at least one of the binding partners of at least one of the component(s) to be determined; and (c) directions for the performance of a protocol for the detection and/or determination of one or more components of an immunochemical reaction between the receptor recognition factor and a specific binding partner thereto.

In accordance with the above, an assay system for screening potential drugs effective to modulate the activity of the receptor recognition factor may be prepared. The receptor recognition factor may be introduced into a test system, and the prospective drug may also be introduced into the resulting cell culture, and the culture thereafter examined to observe any changes in the transcriptional activity of the cells, due either to the addition of the prospective drug alone, or due to the effect of added quantities of the known receptor recognition factor.

Preliminary Considerations

As mentioned earlier, the observation and conclusion underlying the present invention were crystallized from a consideration of the results of certain investigations with particular stimuli. Particularly, the present disclosure is illustrated by the results of work on protein factors that govern transcriptional control of IFNα-stimulated genes, as well as more recent data on the regulation of transcription of genes stimulated by IFNγ. The following is a brief discussion of the role that IFN is believed to play in the stimulation of transcription taken from Darnell et al. *THE NEW BIOLOGIST*, 2 (10), (1990).

Activation of genes by IFNα occurs within minutes of exposure of cells to this factor (Larner et al., 1984, 1986) and is strictly dependent on the IFNα binding to its receptor, a 49-kD plasma membrane polypeptide (Uze et al., 1990). However, changes in intracellular second messenger concentrations secondary to the use of phorbol esters, calcium ionophores, or cyclic nucleotide analogs neither triggers nor blocks IFNα-dependent gene activation (arner et al., 1984; Lew et al., 1989). No other polypeptide, even IFNγ, induces the set of interferon-stimulated genes (ISGs) specifically induced by IFNα. In addition, it has been found that IFNγ-dependent transcriptional stimulation of at least one gene in HeLa cells and in fibroblasts is also strictly dependent on receptor-ligand interaction and is not activated by induced changes in second messengers (Decker et al., 1989; Lew et al., 1989). These highly specific receptor-ligand interactions, as well as the precise transcriptional response, require the intracellular recognition of receptor occupation and the communication to the nucleus to be equally specific.

The activation of ISGs by IFNα is carried out by transcriptional factor ISGF-3, or interferon stimulated gene factor 3. This factor is activated promptly after IFNαtreatment without protein synthesis, as is transcription itself (Larner et al., 1986; Levy et al., 1988; Levy et al., 1989). ISGF-3 binds to the ISRE, the interferon-stimulated response element, in DNA of the response genes (Reich et al., 1987; Levy et al., 1988), and this binding is affected by all of an extensive set of mutations that also affects the transcriptional function of the ISRE (Kessler et al., 1988a). Partially purified ISGF-3 containing no other DNA-binding components can stimulate ISRE-dependent in vitro transcription (Fu et al., 1990). IFN-dependent stimulation of ISGs occurs in a cycle, reaching a peak of 2 hours and declining promptly thereafter (Larner et al., 1986). ISGF-3 follows the same cycle (Levy et al., 1988, 1989). Finally, the presence or absence or ISGF3 in a variety of IFN-sensitive and IFN-resistant cells correlates with the transcription of ISGs in these cells (Kessler et al., 1988b).

ISGF-3 is composed of two subfractions, ISGF-3α and ISGF-3γ, that are found in the cytoplasm before IFN binds to its receptor (Levy et al., 1989). When cells are treated with IFNα, ISGF-3 can be detected in the cytoplasm within a minute, that is, some 3 to 4 minutes before any ISGF-3 is found in the nucleus (Levy et al., 1989). The cytoplasmic component ISGF-3γ can be increased in HeLa cells by pretreatment with IFNγ, but IFNγ does not by itself activate transcription of ISGs nor raise the concentration of the complete factor, ISGF-3 (Levy et al., 1990). The cytoplasmic localization of the proteins that interact to constitute ISGF-3 was proved by two kinds of experiments. When cytoplasm of IFNγ-treated cells that lack ISGF-3 was mixed with cytoplasm of IFNα-treated cells, large amounts of ISGF-3 were formed (Levy et al., 1989). (It was this experiment that indicated the existence of an ISGF-3γ component and an ISGF-3α component of ISGF-3).

In addition, Dale et al. (1989) showed that enucleated cells could respond to IFNα by forming a DNA-binding protein that is probably the same as ISGF-3.

The ISGF-3γ component is a 48-kD protein that specifically recognizes the ISRE (Kessler et al., 1990; Fu et al., 1990). Three other proteins, presumably constituting the ISGF-3a component, were found in an ISGF-3 DNA complex (Fu et al., 1990). The entirety of roles of, or the relationships among these three proteins are not yet known, but it is clear that ISGF-3 is a multimeric protein complex. Since the binding of IFNα to the cell surface converts ISGF-3α from an inactive to an active status within a minute, at least one of the proteins constituting ISGF-3α must be affected promptly, perhaps by a direct interaction with the IFNα receptor.

The details of how the ISGF-3γ component and the three other proteins are activated by cytoplasmic events and then enter the nucleus to bind the ISRE and increase transcription are not entirely known. Further studies of the individual proteins, for example, with antibodies, are presented herein. For example, it is clear that, within 10 minutes of IFNα treatment, there is more ISGF-3 in the nucleus than in the cytoplasm and that the complete factor has a much higher affinity for the ISRE than the 48-kD ISGF-3γ component by itself (Kessler et al., 1990).

In summary, the attachment of interferon-α (IFN-α) to its specific cell surface receptor activates the transcription of a limited set of genes, termed ISGs for "interferon stimulated genes" [Larner et al., *PROC NATL. ACAD. SCI. USA*, 81 (1984); Larner et al., *J. BIOL. CHEM.*, 261 (1986); Friedman et al., *CELL*, 38 (1984)]). The observation that agents that affect second messenger levels do not activate transcription of these genes, led to the proposal that protein:protein interactions in the cytoplasm beginning at the IFN receptor might act directly in transmitting to the nucleus the signal generated by receptor occupation [Levy et al., *NEW BIOLOGIST*, 2 (1991)].

To test this hypothesis, the present applicants began experiments in the nucleus at the activated genes. Initially, the ISRE and ISGF-3 were discovered [Levy et al., *GENES & DEV.*, 2 (1988)].

Partial purification of ISGF-3 followed by recovery of the purified proteins from a specific DNA-protein complex revealed that the complete complex was made up of four proteins [Fu et al., *PROC. NATL. ACAD. SCI. USA*, 87 (1990); Kessler et al., *GENES & DEV.*, 4 (1990)]. A 48 kD protein termed ISGF-3γ, because pre-treatment of HeLa cells with IFN-γ increased its presence, binds DNA weakly on its own [Ibid.; and Levy et al., *THE EMBO. J.*, 9 (1990)]. In combination with the IFN-α activated proteins, termed collectively the ISGF-3α proteins, the ISGF-3γ forms a complex that binds the ISRE with a 50-fold higher affinity [Kessler et al., *GENES & DEV.*, 4 (1990)]. The ISGF-3α proteins comprise a set of polypeptides of 113, 91 and 84 kD. All of the ISGF-3 components initially reside in the cell cytoplasm [Levy et al., *GENES & DEV.*, 3 (1989); Dale et al., *PROC. NATL. ACAD. SCI. USA*, 86 (1989)]. However after only about five minutes of IFN-α treatment the active complex is found in the cell nucleus, thus confirming these proteins as a possible specific link from an occupied receptor to a limited set of genes [Levy et al., *GENES & DEV.*, 3 (1989)].

In accordance with the present invention, specific proteins comprising receptor recognition factors have been isolated and sequenced. These proteins, their fragments, antibodies and other constructs and uses thereof, are contemplated and presented herein. To understand the mechanism of cytoplasmic activation of the ISGF-3α proteins as well as their transport to the nucleus and interaction with ISGF-3γ, this factor has been purified in sufficient quantity to obtain peptide sequence from each protein. Degenerate deoxyoligonucleotides that would encode the peptides were constructed and used in a combination of cDNA library screening and PCR amplification of cDNA products copied from mRNA to identify cDNA clones encoding each of the four proteins. What follows in the examples presented herein a description of the final protein preparations that allowed the cloning of cDNAs encoding all the proteins, and the primary sequence of the 113 kD protein arising from a first gene, and the primary sequences of the 91 and 84 kD proteins which appear to arise from two differently processed RNA products from another gene. Antisera against portions of the 84 and 91 kD proteins have also been prepared and bind specifically to the ISGF-3 DNA binding factor (detected by the electrophoretic mobility shift assay with cell extracts) indicating that these cloned proteins are indeed part of ISGF-3. The availability of the cDNA and the proteins they encode provides the necessary material to understand how the liganded IFN-α receptor causes immediate cytoplasmic activation of the ISGF-3 protein complex, as well as to understand the mechanisms of action of the receptor recognition factors contemplated herein. The cloning of each of ISGF3-α proteins, and the evaluation and confirmation of the particular role played by the 91 kD protein as a messenger and DNA binding protein in response to IFN-γ activation, including the development and testing of antibodies to the receptor recognition factors of the present invention, are all presented in the examples that follow below.

EXAMPLE 1

To purify relatively large amounts of ISGF-3, HeLa cell nuclear extracts were prepared from cells treated overnight (16–18 h) with 0.5 ng/ml of IFN-γ and 45 min. with IFN-α (500 u/ml). The steps used in the large scale purification were modified slightly from those described earlier in the identification of the four ISGF-3 proteins.

Accordingly, nuclear extracts were made from superinduced HeLa cells [Levy et al., THE EMBO. J., 9 (1990)] and chromatographed as previously described [Fu et al., PROC. NATL. ACAD. SCI. USA, 87 (1990)] on: phosphocellulose P-11, heparin agarose (Sigma); DNA cellulose (Boehringer Mannheim; flow through was collected after the material was adjusted to 0.28M KCl and 0.5% NP-40); two successive rounds of ISRE oligo affinity column (1.8 ml column, eluted with a linear gradient of 0.05 to 1.0M KCl); a point mutant ISRE oligonucleotide affinity column (flow through was collected after the material was adjusted to 0.28M KCl); and a final round on the ISRE oligonucleotide column (material was eluted in a linear 0.05 to 1.0M NaCl gradient adjusted to 0.05% NP-40). Column fractions containing ISGF-3 were subsequently examined for purity by SDS PAGE/silver staing and pooled appropriately. The pooled fractions were concentrated by a centricon-10 (Amicon). The pools of fractions from preparations 1 and 2 were combined and run on a 10 cm wide, 1.5 mm thick 7.5% SDS polyacrylamide gel. The proteins were electroblotted to nitrocellulose for 12 hrs at 20 volts in 12.5% MEOH, 25 mM Tris, 190 mM glycine. The membrane was stained with 0.1% Ponceau Red (in 1% acetic acid) and the bands of 113 kD, 91 kD, 84 kD, and 48 kD excised and subjected to peptide analysis after tryptic digestion [Wedrychowski et al., J. BIOL. CHEM., 265 (1990); Aebersold et al., PROC. NATL. ACAD. SCI. USA, 84 (1987)]. The resulting peptide sequences for the 91 kD and 84 kD proteins are indicated in FIG. 6. Degenerate oligonucleotides were designed based on the peptide sequences t19, t13b and t27: (Forward and Reverse complements are denoted by F and R:

```
19F  AACGTIGACCAATTNAACATG      (SEQ ID NO:14)
         T       T  GC    T

T
13bR GTCGATGTTNGGGTANAG         (SEQ ID NO:15)
         A  A  A    A    A

27R  GTACAAITCAACCAGNGCAA       (SEQ ID NO:16)
         T      TG T    T
```

The final ISRE oligonucleotide affinity selection yielded material with the SDS polyacrylamide gel electrophoretic pattern shown in FIG. 4 (left). This gel represented about 1.5% of the available material purified from over 200 L of appropriately treated HeLa cells. While 113, 91, 84 and 48 kD bands were clearly prominent in the final purified preparation (see FIG. 4, right panel), there were also two prominent contaminants of about 118 and 70 kD and a few of other contaminants in lower amounts. [Amino acid sequence data have shown that the contaminants of 86 kD and 70 kD are the KU antigen, a widely-distributed protein that binds DNA termini. However in the specific ISGF-3: ISRE complex there is no KU antigen and therefore it has been assigned no role in IFN-dependent transcriptional stimulation, [Wedrychowski et al., J. BIOL. CHEM., 265 (1990).

Since the mobility of the 113, 91, 84, and 48 kD proteins could be accurately marked by comparison with the partially purified proteins characterized in previous experiments [Fu et al., PROC. NATL. ACAD. SCI. USA, 87 (1990)], further purification was not attempted at this stage. The total purified sample from 200 L of HeLa cells was loaded onto one gel, subjected to electrophoresis, transferred to nitrocellulose and stained with Ponceau red. The 113, 84, 91, and 48 kD protein bands were separately excised and subjected to peptide analysis as described [Aebersold et al., PROC. NATL. ACAD. SCI. USA, 84 (1987)]. Released peptides were collected, separated by HPLC and analyzed for sequence content by automated Edman degradation analysis.

Figure 7B:
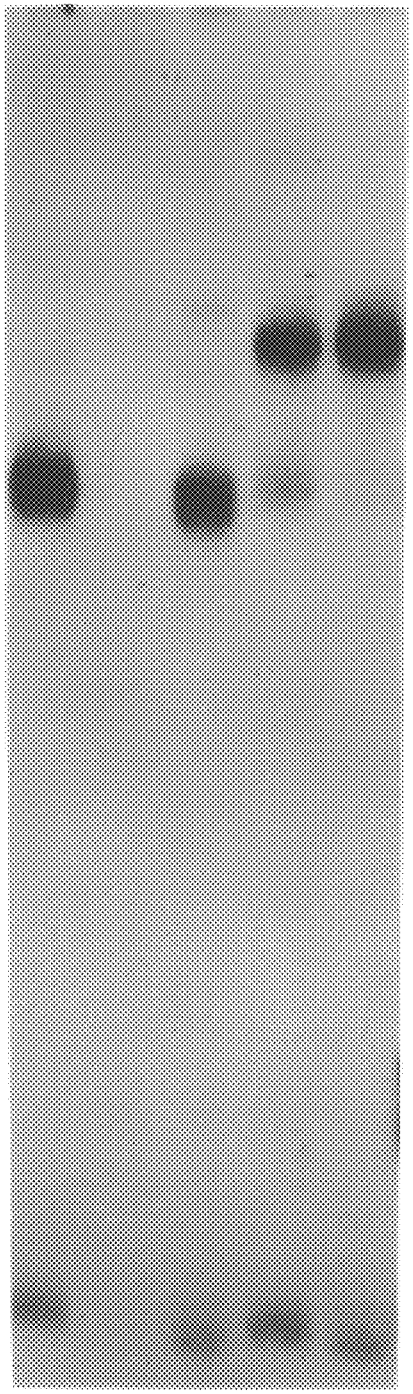

Accordingly, the use of the peptide sequence data for three of four peptides from the 91 kD protein and a single peptide derived from the 84 kD protein is described herein. The peptide sequence and the oligonucleotides constructed from them are given in the legend to FIG. 4 or 6. When oligonucleotides 19F and 13bR were used to prime synthesis from a HeLa cell cDNA library, a PCR product of 475 bp was generated. When this product was cloned and sequenced it encoded the 13a peptide internally. Oligonucleotide 27R derived from the only available 84 kD peptide sequence was used in an anchored PCR procedure amplifying a 405 bp segment of DNA. This 405 bp amplified sequence was identical to an already sequenced region of the 91 kD protein. It was then realized that the peptide t27 sequence was contained within peptide t19 and that the 91 and 84 kD proteins must be related (see FIG. 5 & 7). Oligonucleotides 19F and 13a were also used to select candidate cDNA clones from a cDNA library made from mRNA prepared after 16 hr. of IFN-γ and 45 min. of IFN-α treatment.

Of the numerous cDNA clones that hybridized these oligonucleotides and also the cloned PCR products, one cDNA clone, E4, contained the largest open reading frame flanked by inframe stop codons. Sequence of peptides t19, t13a, and t13b were contained in this 2217 bp ORF (see FIG. 6) which was sufficient to encode a protein of 739 amino acids (calculated molecular weight of 86 kD). The codon for the indicated initial methionine was preceded by three in frame stop codons. This coding capacity has been confirmed by translating in vitro an RNA copy of the E4 clone yielding product of nominal size of 86 kD, somewhat shorter than the in vitro purified 91 kD protein discussed earlier (data not shown). Perhaps this result indicates post-translational modification of the protein in the cell.

A second class of clones was also identified (see FIG. 5). E3, the prototype of this class was identical to E4 from the 5' end to bp 2286 (aa 701) at which point the sequences diverged completely. Both cDNAs terminated with a poly (A) tail. Primer extension analysis suggested another ~150 bp were missing from the 5' end of both mRNAs. DNA probes were made from the clones representing both common and unique sequences for use in Northern blot analyses. The preparation of the probes is as follows: 20 mg of cytoplasmic RNA (0.5% NP-40 lysate) of IFN-α treated (6 h) HeLa RNA was fractionated in a 1% agarose, 6% formaldehyde gel (in 20 mM MOPS, 5 mM NaAc, 1 mM EDTA, pH 7.0) for 4.5 h at 125 volts. The RNA was transferred in 20×SSC to Hybond-N (Amersham), UV crosslinked and hybridized with 1×106 cpm/ml of the indicated probes ($1.5 \times 10^8$ cpm/mg).

Probes from regions common to E3 and E4 hybridized to two RNA species of approximately 3.1 KB and 4.4 KB. Several probes derived from the 3' non-coding end of E4, which were unique to E4, hybridized only the larger RNA species. A labeled DNA probe from the unique 3' noncoding end of E3 hybridized only the smaller RNA species.

Review of the sequence at the site of 3' discontinuity between E3 and E4 suggested that the shorter mRNA results from choice of a different poly(A) site and 3' exon that begins at bp 2286 (the calculated molecular weight from the E3. The last two nucleotides before the change are GT followed by GT in E3 in line with the consensus nucleotides at an exon-intron junction. Since the ORF of E4 extends to bp 2401 it encodes a protein that is 38 amino acids longer than the one encoded by E3, but is otherwise identical (ORF is 82 kD).

Since there is no direct assay for the activity of the 91 or 84 kD protein, an independent method was needed to determine whether the cDNA clones we had isolated did indeed encode proteins that are part of ISGF-3. For this purpose antibodies were initially raised against the sequence from amino acid 597 to amino acid 703 (see FIG. 6) by expressing this peptide in the pGEX-3X vector (15) as a bacterial fusion protein. This antiserum (a42) specifically recognized the 91 kD and 84 kD proteins in both crude extracts and purified ISGF-3 (see FIG. 7a). More importantly this antiserum specifically affected the ISGF-3 band in a mobility shift assay using the labeled ISRE oligonucleotide (see FIG. 7b) confirming that the isolated 91 kD and 84 kD cDNA clones (E4 and E3) represent a component of ISGF-3. Additional antisera were raised against the amino terminus and carboxy terminus of the protein encoded by E4. The amino terminal 59 amino acids that are common to both proteins and the unique carboxy terminal 34 amino acids encoded only by the larger mRNA were expressed as fusion proteins in pGEX-3X for immunization of rabbits. Western blot analysis with highly purified ISGF-3 demonstrated that the amino terminal antibody (a55) recognized both the 91 kD and 84 kD proteins as expected. However, the other antibody (a57) recognized only the 91 kD protein confirming our assumption that the larger mRNA (4.4 KB) and larger cDNA encodes the 91 kD protein while the shorter mRNA (3.1 KB) and cDNA encodes the 84 kD protein (see FIG. 7a).

EXAMPLE 2

In this example, the cloning of the 113 kD protein that comprises one of the three ISGF-3α components is disclosed.

From SDS gels of highly purified ISGF-3, the 113 kD band was identified, excised and subjected to cleavage and peptide sequence analysis [Aebersold et al., *PROC NATL. ACAD. SCI. USA*, 87 (1987)]. Five peptide sequences (A–E) were obtained (FIG. 8A). Degenerate oligonucleotide probes were designed according to these peptides which then were radiolabeled to search a human cDNA library for clones that might encode the 113 kD protein. Eighteen positive cDNA clones were recovered from $2.5 \times 10^5$ phage plaques with the probe derived from peptide E (FIG. 8A, and the legend). Two of them were completely sequenced. Clone f11 contained a 3.2 KB cDNA, and clone ka31 a 2.6 KB cDNA that overlapped about 2 KB but which had a further extended 5' end in which a candidate AUG initiation codon was found associated with a well-conserved Kozak sequence [Kozak, *NUCLEIC ACIDS RES.*, 12 (1984)].

Figure 9A:
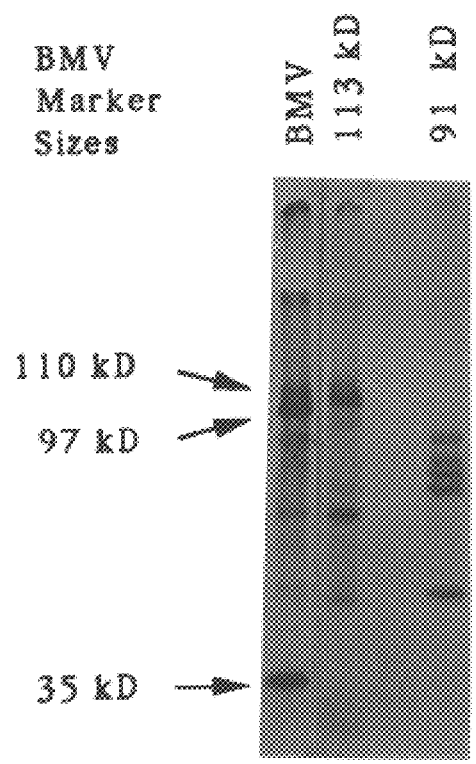
Figure 9B:
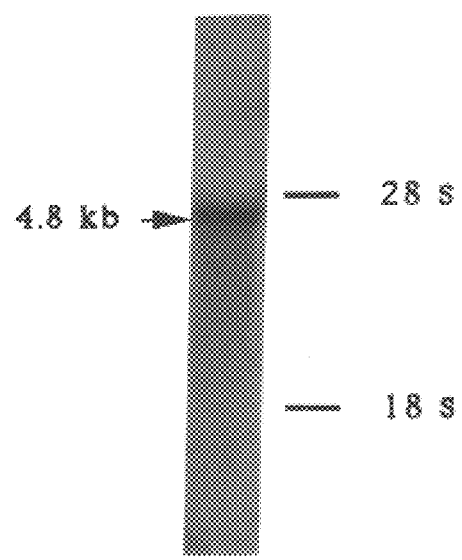

In addition to the phage cDNA clones, a PCR product made between oligonucleotides that encoded peptide D and E also yielded a 474 NT fragment that when sequenced was identical with the cDNA clone in this region. A combination of these clones f11 and ka31 revealed an open reading frame capable of encoding a polypeptide of 851 amino acids (FIG. 8A). These two clones were joined within their overlapping region and RNA transcribed from this recombinant clone was translated in vitro yielding a polypeptide that migrated in an SDS gel with a nominal molecular weight of 105 kD (FIG. 9A). An appropriate clone encoding the 91 kD protein was also transcribed and the RNA translated in the same experiment. Since both the apparently complete cDNA clones for the 113 kD protein and the 91 kD protein produce RNAs that when translated into proteins migrate somewhat faster than the proteins purified as ISGF-3 components, it is possible that the proteins undergo post-translational modification in the cell causing them to be slightly retarded during electrophoresis. When a 660 bp cDNA encoding the most 3' end of the 113 kD protein was used in a Northern analysis, a single 4.8 KB mRNA species was observed (FIG. 9B).

No independent assay is known for the activity of the 113 kD (or indeed any of the ISGF-3α proteins,) but it is known that the protein is part of a DNA binding complex that can be detected by an electrophoretic mobility shift assay [Fu et al., *PROC. NATL. ACAD. SCI. USA*, 87 (1990)]. Antibodies to DNA binding proteins are known to affect the formation or migration of such complexes. Therefore antiserum to a polypeptide segment (amino acid residues 323 to 527) fused with bacterial glutathione synthetase [Smith et al., *PROC. NATL. ACAD. SCI. USA*, 83 (1986)] was raised in rabbits to determine the reactivity of the ISGF-3 proteins with the antibody. A Western blot analysis showed that the antiserum reacted predominantly with a 113 kD protein both in the ISGF3 fraction purified by specific DNA affinity chromatography (Lane 1) and in crude cell extract (Lane 2, FIG. 10A). The weak reactivity to lower protein bands was possibly due to 113 kD protein degradation. Most importantly, the antiserum specifically removed almost all of the gel-shift complex leaving some of the oligonucleotide probe in "shifted-shift" complexes which were specifically competed away with a 50 fold molar excess of the oligonucleotide binding site (the ISRE, ref. 2) for ISGF3 (Fig. 10B). Notably, this antiserum had no effect on the faster migrating shift band produced by ISGF3-γ component alone (FIG. 10B). Thus it appeared that the antiserum to the 113 kD fusion product does indeed react with another protein that is part of the complete ISGF-3 complex.

A detailed sequence comparison between the 113 and 91 sequences followed (FIG. 8B): while the nucleotide sequence showed only a distant relationship between the two proteins, there were long stretches of amino acid identity. These conserved regions were scattered throughout almost the entire 715 amino acid length encoded by the 91/84 clone. It was particularly striking that the regions corresponding to amino acids 1 to 48 and 317 to 353 and 654 to 678 in the 113 sequence were 60% to 70% identical to corresponding regions of the 91 kD sequence. Thus the genes encoding the 113 and 84/91 proteins are closely related but not identical.

Through examination for possible consensus sequences that might reveal sub-domain structures in the 113 kD or 84/91 kD sequence, it was found that both proteins contained regions whose sequence might form a coil structure with heptad leucine repeats. This occurred between amino acid 210 and 245 in the 113 kD protein and between 209 and 237 in the 84/91 protein. In both the 113 kD and the 91/84 kD sequences, 4 out of 5 possible heptad repeats were leucine and one was valine. Domains of this type might provide a protein surface that encourages homo-or heterotypic protein interactions which have been observed in several other transcription factors [Vinson et al., *SCIENCE*, 246 (1989)]. An extended acidic domain was located at the carboxyl terminal of the 113 kD protein but not in 91 kD protein (FIG. 8A), possibly implicating the 113 kD protein in gene activation [Hope et al., Ma et al., *CELL*, 48 (1987)].

Discussion

When compared at moderate or high stringency to the Genbank and EMBL data bases, there were no sequences like 113 or the 84/91 sequence. Preliminary PCR experiments however indicate that there are other family members with different sequences recoverable from a human cell cDNA library (Qureshi and Darnell unpublished). Thus, it appears that the 113 and 84/91 sequences may represent the first two members to be cloned of a larger family. of proteins. We would hypothesize that the 113 kD and 84/91 kD proteins may act as signal transducers, somehow interacting with the internal domain of a liganded IFNα receptor or its associated protein and further that a family of waiting cytoplasmic proteins exist whose purpose is to be specific signal transducers when different receptors are occupied. Many experiments lie ahead before this general hypothesis can be crucially tested. Recent experiments have indicated that inhibitors of protein kinases can prevent ISGF-3 complex formulation [Reich et al., *PROC. NATL. ACAD. SCI. USA*, 87 (1990); Kessler et al., *J. BIOL. CHEM.*, 266 (1991)]. However, neither the IFNα or IFNγ receptors that have so far been cloned have intrinsic kinase activity [Uze et al., *CELL*, 60 (1990); Aguet et al., *CELL*, 55 (1988)]. We would speculate that either a second receptor chain with kinase activity or a separate kinase bound to a liganded receptor could be a part of a complex that would convey signals to the ISGF-3α proteins at the inner surface of the plasma membrane.

From the above, it has been concluded that accurate peptide sequence from ISGF-3 protein components have been determined, leading to correct identification of cDNA clones encoding the 113 , 91 and 84 kD components of ISGF-3. Since staurosporine, a broadly effective kinase inhibitor blocks IFN-α induction of transcription and of ISGF-3 formation [Reich et al., *PROC. NATL. ACAD. SCI. USA*, 87 (1990); Kessler et al.,*J. BIOL. CHEM.*, 266 (1991)] it seems possible that the ISGF-3α proteins are direct cytoplasmic substrates of a liganded receptor-associated kinase. The antiserum against these proteins should prove invaluable in identifying the state of the ISGF-3α proteins before and after IFN treatment and will allow the direct exploration of the biochemistry of signal transduction from the IFN receptor.

EXAMPLE 3

As mentioned earlier, the observation and conclusion underlying the present invention were crystallized from a consideration of the results of certain investigations with particular stimuli. Particularly, the present disclosure is illustrated by the results of work on protein factors that govern transcriptional control of IFNα-stimulated genes, as well as more recent data on the regulation of transcription of genes stimulated by IFNγ.

For example, there is evidence that the 91 kD protein is the tyrosine kinase target when IFNγ is the ligand. Thus two different ligands acting through two different receptors both use these family members. With only a modest number of family members and combinatorial use in response to different ligands, this family of proteins becomes an even more likely possibility to represent a general link between ligand-occupied receptors and transcriptional control of specific genes in the nucleus.

Further study of the 113, 91 and 84 kD proteins of the present invention has revealed that they are phosphorylated in response to treatment of cells with IFNα (FIG. 11). Moreover, when the phosphoamino acid is determined in the newly phosphorylated protein the amino acid has been found to be tyrosine (FIG. 12). This phosphorylation has been observed to disappear after several hours, indicating action of a phosphatase of the 113, 91 and 84 kD proteins to stop transcription. These results show that IFN dependent transcription very likely demands this particular phosphorylation and a cycle of interferon-dependent phosphorylation-dehosphorylation is responsible for controlling transcription.

It is proposed that other members of the 113–91 protein family will be identified as phosphorylation targets in response to other ligands. If as is believed, the tyrosine phosphorylation site on proteins in this family is conserved, one can then easily determine which family members are activated (phosphorylated), and likewise the particular extracellular polypeptide ligand to which that family member is responding. The modifications of these proteins (phosphorylation and dephosphorylation) enables the preparation and use of assays for determining the effectiveness of pharmaceuticals in potentiating or preventing intracellular responses to various polypeptides, and such assays are accordingly contemplated within the scope of the present invention.

EXAMPLE 4

Identification of Murine 91 kD Protein

A fragment of the gene encoding the human 91 kD protein was used to screen a murine thymus and spleen cDNA library for homologous proteins. The screening assay yielded a highly homologous gene encoding a murine polypeptide that is greater than 95% homologous to the human 91 kD protein. The nucleic acid and deduced amino acid sequence of the murine 91 kD protein are shown in FIG. 13A–13C, and SEQ ID NO:7 (nucleotide sequence) and SEQ ID NO:8 (amino acid sequence).

EXAMPLE 5

Additional Members of The 113–91 Protein Family

Using a 300 nuclide fragment amplified by PCR from the SH2 region of the murine 91 kD protein gene, murine genes encoding two additional members of the 113–91 family of receptor recognition factor proteins were isolated from a murine splenic/thymic cDNA library according to the method of Sambrook et al. (1989, *Molecular Cloning, A Laboratory Manual,* 2nd. ed., Cold Spring Harbor Press: Cold Spring Harbor, N.Y.) constructed in the ZAP vector. Hybridization was carried out at 42° C. and washed at 42° C. before the first exposure (Church and Gilbert, 1984, Proc. Natl. Acad. Sci. USA 81: 1991–95). Then the filters were washed in 2×SSC, 0.1% SDS at 65° C. for a second exposure. Stat1 clones survived the 65° C. washing, whereas Stat3 and Stat4 clones were identified as plaques that lost signals at 65° C. The plaques were purified and subcloned according to Stratagene commercial protocols.

This probe was chosen to screen for other STAT family members because, while Stat1 and Stat2 SH2 domains are quite similar over the entire 100 to 120 amino acid region, only the amino terminal half of the STAT SH2 domains strongly resemble the SH2 regions found in other proteins.

The two genes have been cloned into plasmids 13sf1 and 19sf6. The nucleotide sequence, and deduced amino acid sequence, for the 13sf1 and 19sf6 genes are shown in FIGS. 14 and 15, respectively. These proteins are alternatively termed Stat4 and Stat3, respectively. Comparison with the sequence of Stat91 (Stat1) and Stat113 (Stat2) shows several highly conserved regions, including the putative SH3 and SH2 domains. The conserved amino acid stretches likely point to conserved domains that enable these proteins to carry out transcription activation functions. Stat3, like Stat1 (Stat91), is widely expressed, while Stat4 expression is limited to the testes, thymus, and spleen. Stat3 has been found to be activated as a DNA binding protein through phosphorylation on tyrosine in cells treated with EGF or IL-6, but not after IFN-γ, treatment.

Both the 13sf1 and 19sf6 genes share a significant homology with the genes encoding the human and murine 91 kD protein. There is corresponding homology between the deduced amino acid sequences of the 13sf1 and 19sf6 proteins and the amino acid sequences of the human and murine 91 kD proteins, although not the greater than 95% amino acid homology that is found between the murine and human 91 kD proteins. Thus, though clearly of the same family as the 91 kD protein, the 13sf1 and 19sf6 genes encode distinct proteins.

The chromosomal locations of the murine STAT proteins (1–4) have been determined: Stat1 and Stat4 are located in the centromeric region of mouse chromosome 1 (corresponding to human 2q 32–34q); the two other genes are on other chromosomes.

Southern analysis using probes derived from 13sf1 and 19sf6 on human genomic libraries have established that genes corresponding to the murine 13sf1 and 19sf6 genes are found in humans.

Tissue distribution of mRNA expression of these genes was evaluated by Northern hybridization analysis. The results of this distribution analysis are shown in the following Table.

TABLE

DISTRIBUTION OF mRNA EXPRESSION OF 13sf1, 19sf6, 91 kD PROTEINS

| ORGAN | 13sf1 | 19sf6 | 91 KD |
| --- | --- | --- | --- |
| BRAIN | – | + | – |
| HEART | – | +++ | – |
| KIDNEY | – | – | – |
| LIVER | – | + | + |
| LUNG | – | – | – |
| SPLEEN | + | + | ++++ |
| TESTIS | ++++ | ++ | N.A. |
| THYMUS | ++ | ++ | +++ |
| EMBRYO (16d) | not found | found | found |

Northern analysis demonstrates that there is variation in the tissue distribution of expression of the mRNAs encoded by these genes. The variation and tissue distribution indicates that the specific genes encode proteins that are responsive to different factors, as would be expected in accordance with the present invention. The actual ligand, the binding of which induces phosphorylation of the newly discovered factors, will be readily determinable based on the tissue distribution evidence described above.

To determine whether the Stat3 and Stat4 proteins were present in cells, protein blots were carried out with antisera against each protein. The antisera were obtained by subcloning amino acids 688 to 727 of Stat3 and 678 to 743 of Stat4 to pGEX1λt (Pharmacia) by PCR with oligonucleotides based on the boundary sequence plus restriction sites (BamHI at the 5' end and EcoRI at the 3' end), allowing for in-frame fusion with GST. One milligram of each antigen was used for the immunization and three booster injections were given 4 weeks apart. Anti-Stat3 and anti-Stat4 sera were used 1:1000 in Western blots using standard protocols. To avoid cross reactivity of the antisera, antibodies were raised against the C-terminal of Stat3 and Stat4, the less homologous region of the protein.

These proteins were unambiguously found in several tissues where the mRNA wan known to be present. Protein expression was checked in several cell lines as well. A protein of 89 kD reactive with Stat4 antiserum was expressed in 70Z cells, a preB cell line, but not in many other cell lines. Stat3 was highly expressed, predominantly as a 97 kD protein, in 70Z, HT2 (a mouse helper T cell clone), and U937 (a macrophage-derived cell).

To prove that the full length functional cDNA clones of Stat3 and Stat4 were obtained, the open reading frames of each cDNA was independently (i.e., separately) cloned into the Rc/CMV expression vector (Invitrogen) downstream of a CMV promoter. The resulting plasmids were transfected into COS1 cells and proteins were extracted 60 hrs post-transfection and examined by Western blot after electrophoresis. Untransfected COS1 cells expressed a low level of 97 kD Stat3 protein but did not express a detectable level of Stat4. Upon transfection of the Stat3-expressing plasmid, the 97 kD Stat3 was increased at least 10-fold. And 89 kD protein antigenically related to Stat3, found as a minor band in most cell line extracts, was also increased post-transfection. This protein therefore appears to represent another form of Stat3 protein, or an antigenically similar protein whose synthesis is stimulated by Stat3. Transfection with Stat4 led to the expression of a 89 kD reactive band indistinguishable in size form the p89 Stat4 found in 70Z cell extracts.

Discussion

As mentioned earlier, the observation and conclusion underlying the present invention were crystallized from a consideration of the results of certain investigations with particular stimuli. Particularly, the present disclosure is illustrated by the results of work on protein factors that govern transcriptional control of IFNα-stimulated genes, as well as more recent data on the regulation of transcription of genes stimulated by IFNγ. The present disclosure is further illustrated by the identification of related genes encoding protein factors responsive to as yet unknown factors. It is expected that the murine 91 kD protein is responsive to IFN-γ.

For example, the above represents evidence that the 91 kD protein is the tyrosine kinase target when IFNγ is the ligand. Thus two different ligands acting through two different receptors both use these family members. With only a modest number of family members and combinatorial use in response to different ligands, this family of proteins becomes an even more likely possibility to represent a general link between ligand-occupied receptors and transcriptional control of specific genes in the nucleus.

It is proposed and shown by the foregoing that other members of the 113–91 protein family will be and have been identified as phosphorylation targets in response to other ligands. If as is believed, the tyrosine phosphorylation site on proteins in this family is conserved, one can then easily determine which family members are activated (phosphorylated), and likewise the particular extracellular polypeptide ligand to which that family member is responding. The modifications of these proteins (phosphorylation and dephosphorylation) enables the preparation and use of assays for determining the effectiveness of pharmaceuticals in potentiating or preventing intracellular responses to various polypeptides, and such assays are accordingly contemplated within the scope of the present invention.

Earlier work has concluded that DNA binding protein was activated in the cell cytoplasm in response to IFN-γ treatment and that this protein stimulated transcription of the GBP gene (10,14). In the present work, with the aid of antisera to proteins originally studied in connection with IFN-α gene stimulation (7,12,15), the 91 kD ISGF-3 protein has been assigned a prominent role in IFN-γ gene stimulation as well. The evidence for this conclusion included: 1) antisera specific to the 91 kD protein affected the IFN-γ dependent gel-shift complex, and 2) A 91 kD protein could be cross-linked to the GAS IFN-γ activated site. 3) A $^{35}$S-labeled 91 kD protein and a 91 kD immunoreactive protein specifically purified with the gel-shift complex. 4) The 91 kD protein is an IFN-γ dependent tyrosine kinase substrate as indeed it had earlier proved to be in response to IFN-α (15). 5) The 91 kD protein but not the 113 kD protein moved to the nucleus in response to IFN-γ treatment. None of these experiments prove but do strongly suggest that 10 the same 91 kD protein acts differently in different DNA binding complexes that are triggered by either IFN-α or IFN-γ.

These results strongly support the hypothesis originated from studies on IFN-α that polypeptide cell surface receptors report their occupation by extracellular ligand to latent cytoplasmic proteins that after activation move to the nucleus to trigger transcription (4,15,21). Furthermore, because cytoplasmic phosphorylation and factor activation is so rapid it appears likely that the functional receptor complexes contain tyrosine kinase activity. Since the IFN-γ receptor chain that has been cloned thus far (22) has no hint of possessing intrinsic kinase activity, perhaps some other molecule with tyrosine kinase activity couples with the IFN-γ receptor. Two recent results with other receptors suggest possible parallels to the situation with the IFN receptors. The trk protein which has an intracellular tyrosine kinase domain, associates with the NGF receptor when that receptor is occupied (23). In addition, the Ick protein, a member of the src family of tyrosine kinases, is co-precipitated with the T cell receptor (24). It is possible to predict that signal transduction to the nucleus through these two receptors could involve latent cytoplasmic substrates that form part of activated transcription factors. In any event, it seems possible that there are kinases like trk or Ick associated with the IFN-γ receptor or with IFN-α receptor.

With regard to the effect of phosphorylation on the 91 kD protein, it was something of a surprise that after IFN-γ treatment the 91 kD protein becomes a DNA binding protein. Its role must be different in response to IFN-α treatment. Tyrosine is also phosphorylated on tyrosine and joins a complex with the 113 and 84 kD proteins but as judged by UV cross-linking studies (7), the 91 kD protein does not contact DNA.

In addition to becoming a DNA binding protein it is clear that the 91 kD protein is specifically translocated the nucleus in the wake of IFN-γ stimulation.

EXAMPLE 6

Dimerization of Phosphorylated Stat91

Stat91 (a 91 kD protein that acts as a ignal transducer and activator of transcription) is inactive in the cytoplasm of untreated cells but is activated by phosphorylation on tyrosine in response to a number of polypeptide ligands including IFN-α and IFN-γ. This example reports that inactive Stat91 in the cytoplasm of untreated cells is a monomer and upon IFN-γ induced phosphorylation it forms a stable homodimer. The dimer is capable of binding to a specific DNA sequence directing transcription. Dissociation and reassociation assays show that dimerization of Stat91 is mediated through SH2-phosphotyrosyl peptide interactions. Dimerization involving SH2 recognition of specific phosphotyrosyl peptides may well provide a prototype for interactions among family members of STAT proteins to form different transcription complexes and Jak2 for the IFN-γ pathway (42, 43, 44). These kinases themselves become tyrosine phosphorylated to carry out specific signaling events.

Materials and Methods

Cell Culture. Human 2ftGH, U3A cells were maintained in DMEM medium supplied with 10% bovine calf serum. U3A cell lines supplemented with various Stat91 protein constructs were maintained in 0.1 mg/ml G418 (Gibco, BRL). Stable cell lines were selected as described (45). IFN-γ (5 ng/ml, gift from Amgen) treatment of cells was for 15 min. unless otherwise noted.

Plasmid Constructions. Expression construct MNC-84 was made by insertion of the cDNA into the Not I-Barn HI cloning site of an expression vector PMNC (45, 35). MNC-91L was made by insertion of the Stat91 cDNA into the Not I-Bam HI cloning sites of pMNC without the stop codon at the end, resulting the production of a long form of Stat91 with a C-terminal tag of 34 amino acids encoded by PMNC vector.

GST fusion protein expression plasmids were constructed by the using the PGEX-2T vector (Pharmacia). GST-91SH2 encodes amino acids 573 to 672 of Stat91; GST-91mSH2 encodes amino acids 573 to 672 of Stat91 with an Arg-602->Leu-602 mutation; and GST-91SH3 encodes amino acids 506 to 564 of Stat91.

DNA Transfection. DNA transfection was carried by the calcium phosphate method, and stable cell lines were selected in Dulbecco's modified Eagle's medium containing G418 (0.5 mg/ml, Gibco), as described (45).

Preparation of Cell Extracts. Crude whole cell extracts were prepared as described (31). Cytoplasmic and nuclear extracts were prepared essentially as described (46).

Affinity Purification. Affinity purification with a biotinylated oligonucleotide was described (31). The sequence of the biotinylated GAS oligonucleotide was from the Ly6E gene promoter (34).

Nondenaturing Polyacrylanide Gel Anatysis. A nondenatured protein molecular weight marker kit with a range of molecular weights from 14 to 545 kD) was obtained from Sigma. Determining molecular weights using nondenaturing polyacrylamide gel was carried out following the manufacturer's procedure, which is a modification of the methods of Bryan and Davis (47, 48). Phosphorylated and unphosphorylated Stat91 samples obtained from affinity purification using a biotinylated GAS oligonucleotide (31) were resuspended in a buffer containing 10 mM Tris (pH 6.7), 16% glycerol, 0.04% bromphenol blue (BPB). The mixtures were analyzed on 4.5%, 5.5%, 6.5%, and 7.5.% native gels side by side with standard markers using a Bio-Rad mini-Protean II Cell electrophoresis system. Electrophoresis was stopped when the dye (BPB) reached the bottom of the gels. The molecular size markers were revealed by Coomassie blue staining. Phosphorylated and unphosphorylated Stat91 samples were detected by immunoblotting with anti-91T.

Glycerol Gradient Analysis. Cells extracts (Bud 8) were mixed with protein standards (Pharmacia) and subjected to centrifugation through preformed 10%–40% glycerol gradients for 40 hours at 40,000 rpm in an SW41 rotor as described (6).

Gel Mobility Shift Assays. Gel mobility shift assays were carried out as described (34). An oligonucleotide corresponding to the GAS element from the human FcγRI receptor gene (Pearse et al. 1993) was synthesized and used for gel mobility shift assays. The oligonucleotide has the following sequence: 5'GATCGAGATGTATTTCCCA-GAAAAG3' (SEQ. ID NO:17).

Synthesis of Peptides. Solid phase peptide synthesis was used with either a DuPont RAMPS multiple synthesizer or by manual synthesis. C-terminal amino attached to Wang resin were obtained from DuPont/NEN. All amino acids were coupled as the N-Fmoc pentafluorophenyl esters (Advanced Chemtech), except for N-Fmoc, PO-dimethyl-L-phosphotyrosine (Bachem). Double couplings were used. Cleavage from resin and deprotection used thioanisol/m-cresol/TFA/TMSBr at 4° C. for 16 hr. Purification used C-18 column HPLC with 0.1% TFA/acetonitrile gradients. Peptides were characterized by $^1$H and $^{31}$P NMR, and by Mass Spec, and were greater than 95% pure.

Guanidium Hydrochloride Treatment. Extracts were incubated with guanidium hydrochloride (final concentration was 0.4 to 0.6M) for two min. at room temperature and then diluted with gel shift buffer (final concentration of guanidium hydrochloride was 100 mM) and incubated at room temperature for 15 min. $^{32}$P-labeled GAS oligonucleotide probe was then added directly to the mixture followed by gel mobility shift assay.

Dissociation-reassociation Analysis. Extracts were incubated with various concentrations of peptides or fusion proteins, and $^{32}$P-labeled GAS oligonucleotide probe in gel shift buffer was then added to promote the formation of protein-DNA complex followed by mobility shift analysis. This assay did not involve guanidium hydrochloride treatment.

Preparation of Fusion Proteins. Bacterially expressed GST fusion proteins were purified using standard techniques, as described in Birge et al., 1992. Fusion proteins were quantified by O.D. absorbance at 280 nm. Aliquotes were frozen at −70° C.

Results

Detection of Ligand Induced Dimer Formation of Stat91 in Solution. In untreated cells, Stat91 is not phosphorylated on tyrosine. Treatment with IFN-γ leads within minutes to tyrosine phosphorylation and activation of DNA binding capacity. The phosphorylated form migrates more slowly during electrophoresis under denaturing conditions affording a simple assay for the phosphoprotein (31).

Figure 16A:
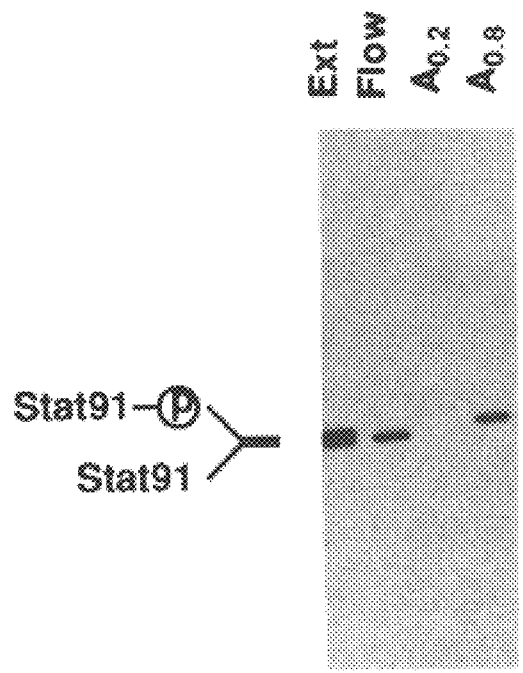
Figure 16B:
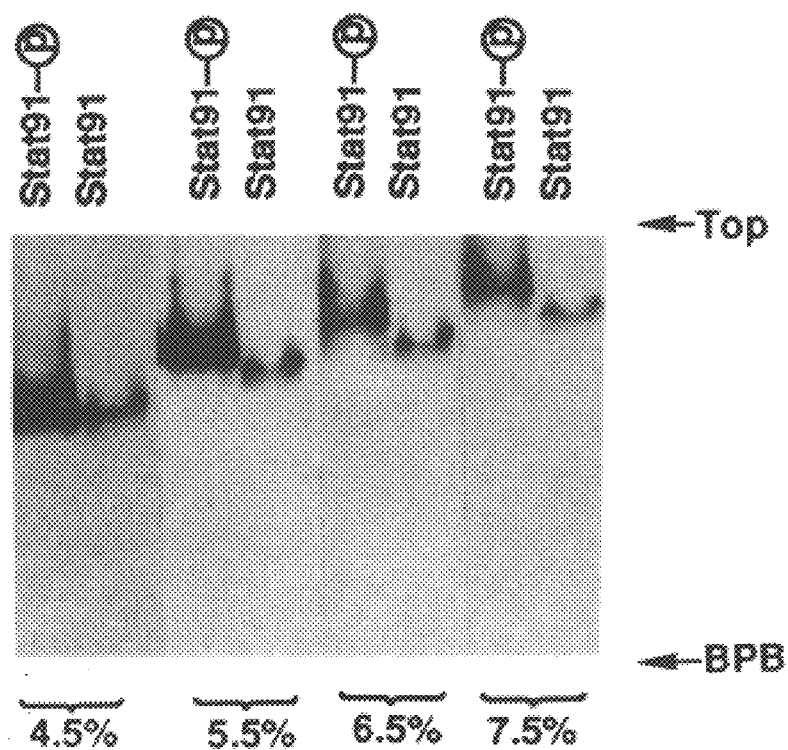

To determine the native molecular weights of the phosphorylated and unphosphorylated forms of Stat91, we separated them by affinity purification using a biotinylated deoxyoligonucleotide containing a GAS sequence (interferon gamma activation site) (FIG. 16A). The separation of phosphorylated Stat91 from the unphosphorylated form was efficient as almost all detectable phosphorylated form could bind to the GAS site while unphosphorylated Stat91 remained unbound. To determine the molecular weights of the purified phosphorylated Stat91 and unphosphorylated Stat91, samples of each were then subjected to electrophoresis through a set of nondenaturing gels containing various concentrations of acrylamide followed by Western blot analysis (FIG. 16B). Native protein size markers (Sigma) were included in the analysis.

This technique was originally described by Bryan (48) and was recently used for dimer analysis (49). The logic of the technique is that increasing gel concentrations affect the migration of larger proteins more than smaller proteins, and the analysis is not affected by modifications such as protein phosphorylation (49).

Figure 16C:
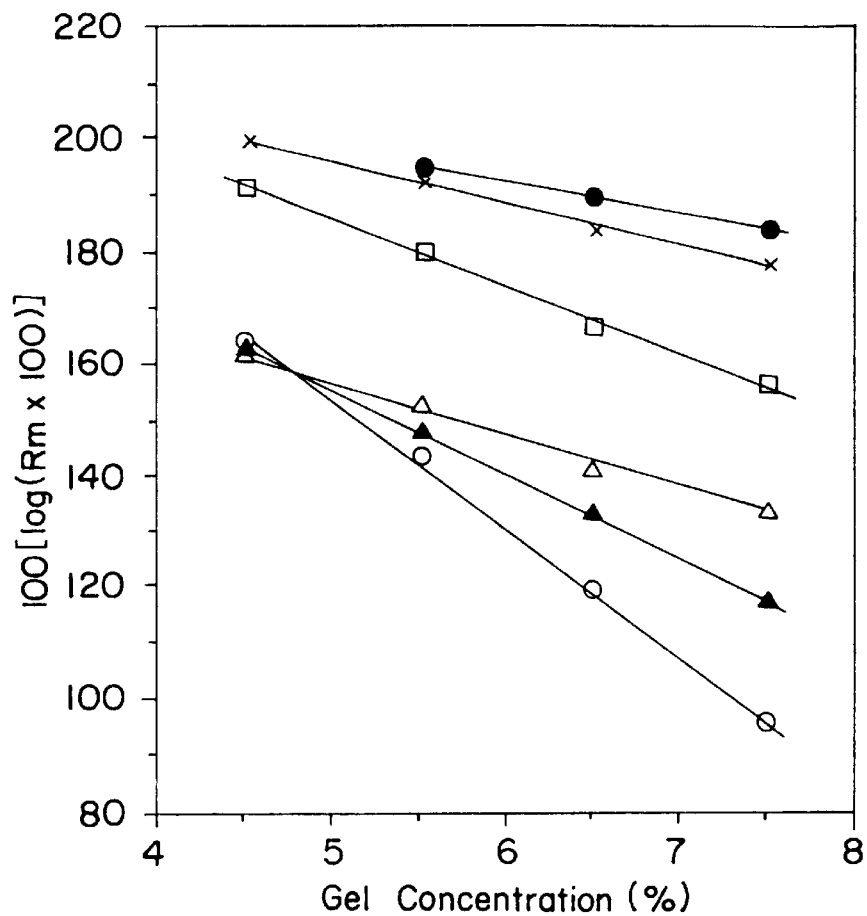
Figure 16D:
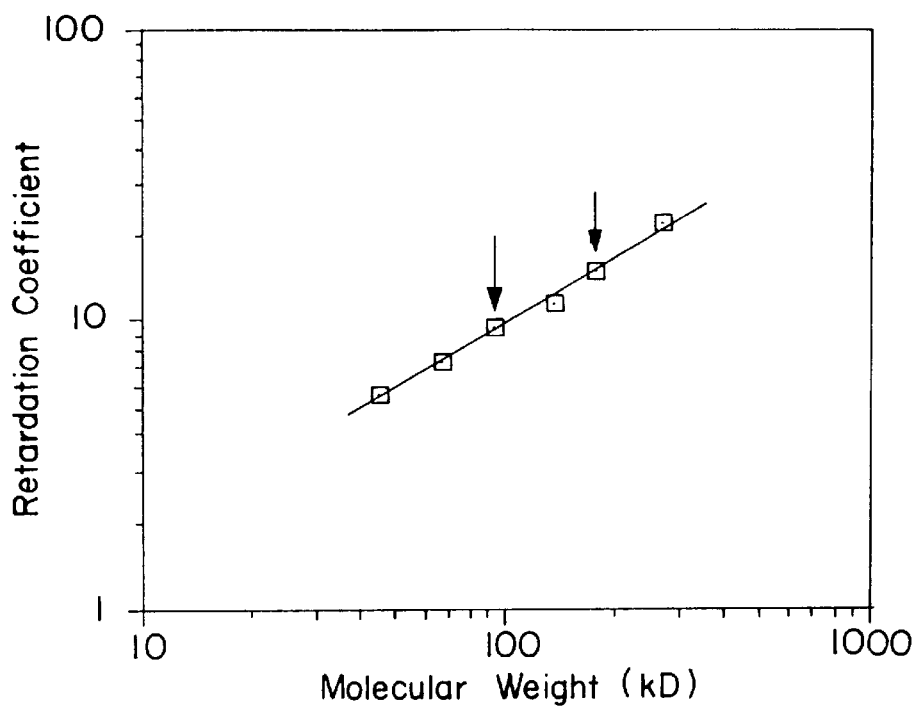

A function of the relative mobilities (Rm) was plotted versus the concentration of acrylamide for each sample to construct Ferguson plots (FIG. 16C). The logarithm of the retardation coefficient (calculated from FIG. 16C) of each sample was then plotted against the logarithm of the relevant molecular weight range (FIG. 16D). By extrapolation of its retardation coefficient (FIG. 16D), the native molecular weight of Stat91 from untreated cells was estimated to be approximately 95 kD, while tyrosine phosphorylated Stat91 was estimated to be about twice as large, or approximately 180 kD. Because the calculated molecular weight from amino acid sequence of Stat91 is 87 kD, and Stat91 migrates on denaturing SDA gels with an apparent molecular weight of 91 kD (see supra, and refs. 12 and 45), we concluded that in solution, unphosphorylated Stat91 existed as a monomer while tyrosine phosphorylated Stat91 is a dimer.

We also employed glycerol gradient analysis to estimate the native molecular weights of both phosphorylated and unphosphorylated Stat91 (FIG. 17). Whole cell extract of fibroblast cells (Bud8) treated with IFN-γ were prepared and subjected to sedimentation through a 10–40% glycerol gradient. Fractions from the gradient were collected and analyzed by both immunoblotting and gel mobility shift analysis (FIG. 17A and 17B). As expected, two electrophoretic forms of Stat91 could be detected by immunoblotting (FIG. 17A): the slow-migrating form (tyrosine phosphorylated) and the fast-migrating form (unphosphorylated; FIG. 17A). The phosphorylated Stat91 sedimented more rapidly than the unphosphorylated form. Again, using molecular weight markers, the native molecular weight of the unphosphorylated form of Stat91 appeared to be about 90 kD while the tyrosine phosphorylated form of Stat91 was about 180 kD (FIG. 17C), supporting the conclusion that unphosphorylated Stat91 existed as a monomer in solution while the tyrosine phosphorylated form exists as a dimer. When fractions from the glycerol gradients were analyzed by electrophoretic mobility shift analysis (FIG. 17B), the peak of the phosphorylated form of Stat91 correlated well with the DNA-binding activity of Stat91. Thus only the phosphorylated dimeric Stat91 has the sequence-specific DNA recognition capacity.

Stat91 Binds DNA as a Dimer. Long or short versions of DNA binding protein can produce, respectively, a slower or a faster migrating band during gel retardation assays. Finding intermediate gel shift bands produced by mixing two different sized species provides evidence of dimerization of the DNA binding proteins. Since Stat91 requires specific tyrosine phosphorylation in ligand-treated cells for its DNA binding, we sought evidence of formation of such heterodimers, first in transfected cells. An expression vector (MNC911) encoding Stat91L, a recombinant form of Stat91 containing an additional 34 amino acid carboxyl terminal tag was generated. [The extra amino acids were encoded by a segment of DNA sequence from plasmid pMNC (see Materials and Methods).] A Stat84 expression vector (MNC84) was also available (45). From somatic cell genetic experiments, mutant human cell lines (U3) are known that lack the Stat91/84 mRNA and proteins (29,30). The U3 cells were therefore separately transfected with vectors encoding Stat84 (MNC84) or Stat91L (MNC91L) or a mixture of both vectors. Permanent transfectants expressing Stat84 (C84), Stat91L (C91L) or both proteins (Cmx) were isolated (FIG. 18A).

Mobility shift analysis was performed with extracts from these stable cell lines (FIG. 18B). Extracts of IFN-γ-treated C84 cells produced a faster migrating gel shift band than extracts of treated C91L cells. Most importantly, extracts from IFN-γ-treated Cmx cells expressing both Stat84 and Stat91L proteins formed an additional intermediate gel shift band. Anti-91, an antiserum against the C-terminal 38 amino acids of Stat91 (12) that are absent in Stat84, specifically removed the top two shift bands seen with the Cmx extracts. Anti-91, an antiserum against amino acids 609 to 716 (15) that recognizes both Stat91L and Stat84, proteins inhibited the binding of all three shift bands. Thus, the middle band formed by extracts of the Cmx cells is clearly identified as a heterodimer of Stat84 and Stat91. We concluded that both Stat91 and Stat84 bind DNA as homodimers and, if present in the same cell, will form heterodimers.

We next wanted to detect the formation of dimers in vitro. When cytoplasmic or nuclear extracts of IFN-γ-treated C84 or C91L cells were mixed and analyzed (FIG. 19), only the fast or slow migrating gel shift bands were observed. Thus it appeared that once formed in vivo, the dimers were stable. To promote the formation of protein interchange between the subunits of the dimer, a mixture of either cytoplasmic or nuclear extracts of IFN-γ-treated C84 or C91L cells were subjected mild denaturation-renaturation treatment: extracts were made 0.5M with respect to guanidium hydrochloride for two minutes and then diluted for renaturation and subsequently used for gel retardation analysis. The formation of heterodimer was clearly detected after this treatment. When extracts from either C84 cells alone or C91L cells alone were subjected to the same treatment, the intermediate band did not form. The intermediate band was again proven by antiserum treatment to consist of Stat84/Stat91L dimer (data not shown).

This experiment defined conditions under which the dimer was stable, but also showed that dissociation and reassociation of the dimer in vitro was possible. Since guanidium hydrochloride is known to disrupt only non-covalent chemical bonds, it seemed that Stat91 (or Stat84) homodimerization was mediated through non-covalent interactions.

Dimerization of Stat91 Involves Phosphotyrosyl Peptide and SH2 Interactions. Based on the results described above, we devised a dissociation-reassociation assay in the absence of guanidium hydrochloride to explore the possible nature of interactions involved in dimer formation (FIG. 20). When the short and long forms of a homodimer are mixed with a dissociating agent (e.g., a peptide containing the putative dimerization domain), the subunits of the dimer should dissociate (in a concentration dependent fashion) due to the interaction of the agent with the dimerization domain(s) of the protein. When a specific DNA probe is subsequently added to the mixture to drive the formation of a stable protein-DNA complex, the detection of any reassociated or remaining dimers can be assayed. In the presence of low concentration of the dissociating agent, addition of DNA to form the stable protein-DNA complex should lead to the detection of homodimers as well as heterodimers. At high concentration of the dissociating agent, subunits of the dimer may not be able to re-form and no DNA-protein complexes would be detected (FIG. 20).

The Stat91 sequence contains an SH2 domain (amino acids 569 to 700, see discussion below), and we knew that Tyr-701 was the single phosphorylated tyrosine residue required for DNA binding activity (supra, 45). Furthermore, we have observed that phosphotyrosine at 10 mM, but not phosphoserine or phosphothreonine, could prevent the formation of Stat91-DNA complex. We therefore sought evidence that the dimerization of Stat91 involved specific SH2-phosphotyrosine interaction using the dissociation and reassociation assay.

In order to evaluate the role of the SH2-phosphotyrosine interation, two peptides fragments of Stat91 corresponding to segments of the SH2 and phosphotyrosing domains of Stat91 were prepared: a non-phosphorylated peptide (91Y), LDGPKGTGYIKTELI (SEQ. ID NO:18) (corresponding to amino acids 693–707), and a phosphotyrosyl peptide (91Y-p), GY*IKTE (SEQ. ID NO:19) (representing residues 700–705).

Activated Stat84 or Sta91L was obtained from IFN-treated C84 or C91L cells and mixed in the presence of various concentrations of the peptides followed by gel mobility shift analysis. The non-phosphorylated peptide had no effect on the presence of the two gel shift bands characteristic of Stat84 or Stat91L homodimers (FIG. 21, lane 24). In contrast, the phosphorylated peptide (91Y-p) at the concentration of 4 μM clearly promoted the exchange between the subunits of Stat84 dimers and Stat91L dimers to form heterodimers (FIG. 21, lane 5). At a higher concentration (160 μM), peptide 91Y-p but not the unphosphorylated peptide dissociated the dimers and blocked the formation of DNA protein complexes (FIG. 21, lane 7).

When cells are treated with IFN-α both Stat91 (or 84) and Stat113 become phosphorylated (15). Antiserum to Stat113 can precipitate both Stat113 and Stat91 after IFN-α-treatment but not before, suggesting IFN-α dependent interaction of these two proteins, perhaps as a heterodimer (15).

In Stat113, tyr-690 in the homologous position to Tyr-701 in Stat91 is the single target residue for phosphorylation. Amino acids downstream of the affected tyrosine residue show some homology between the two proteins. We therefore prepared a phosphotyrosyl peptide of Stat113 (113Y-p), KVNLQERRKY*LKHR (SEQ. ID NO:20) [amino acids 681 to 694; (38)]. At concentrations similar to 91Y-p, 113Y-p also promoted the exchange of subunits between the Stat84 and Stat91L, while at a high concentration (40 μM), 113Y-p prevented the gel shift bands almost completely (FIG. 21, lane 8–10).

We prepared a phosphotyrosyl peptide (SrcY-p), EPQY*EEIPIYL (SEQ. ID NO:21) which is known to interact with the Src SH2 domain with a high affinity (50). This peptide showed no effect on the Stat91 dimer formation (FIG. 21, lane 11–13). Thus, it seems that Stat91 dimerization involves SH2 interaction with tyrosine residues in specific peptide sequence.

Figure 22B:
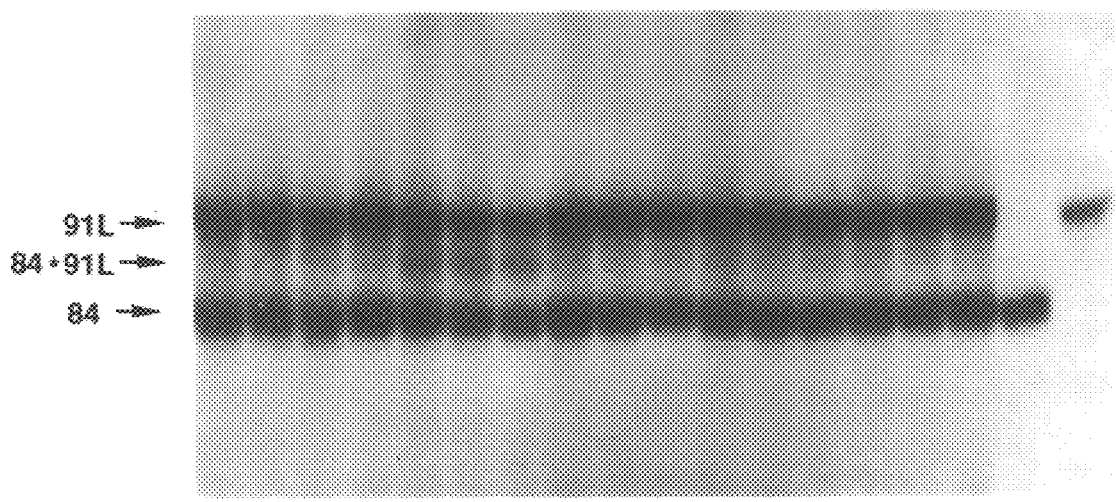

To test further the specificity of Stat91 dimerization mediated through specific-phosphotyrosyl-peptide SH2 interaction, a fusion product of glutathione-S-transferase with the Stat91-SH2 domain (GST-91SH2) was prepared (FIG. 22A) and used in the in vitro dissociation reassociation assay. At concentrations of 0.5 to 5 μM, the Stat91-SH2 domain promoted the formation of a heterodimer (FIG. 22B, lanes 5–7). In contrast, neither GST alone, nor fusion products with a mutant ($R^{602}$->$L^{602}$) Stat91-SH2 domain (GST 91mSH2) that renders Stat91 non-functional in vivo, a Stat91 SH3 domain (GST-91SH3), nor the Src SH2 domain (GST-SrcSH2), induced the exchange of subunits between the Stat84 and Stat91L homodimers (FIG. 22B).

Discussion

The initial sequence analysis of the Stat91 and Stat113 proteins revealed the presence of SH2 like domains (see 13,38). Further it was found that STAT proteins themselves are phosphorylated on single tyrosine residues during their activation (15,31). Single amino acid mutations either removing the Stat91 phosphorylation site, Tyr-701, or converting Arg-702 to Leu in the highly conserved "pocket" region of the SH2 domain abolished the activity of Stat91 (45). Thus it seemed highly likely that one possible role of the STAT SH2 domains would be to bind the phosphotyrosine residues in one of the JAK kinases.

Since the activated STATs have phosphotyrosine residues and SH2 domains, a second suggested role for SH2 domains was in protein-protein interactions within the STAT family. By two physical criteria—electrophoresis in native gels and sedimentation on gradients—Stat91 in untreated cells is a monomer and in treated cells is a dimer (FIGS. 16–18). Since phosphotyrosyl peptides from Stat91 or Stat113 and the SH2 domain of Stat91 could efficiently promote the formation of heterodimers between Stat91L and Stat84 in a disassociation and reassociation assay, we conclude that dimerization of Stat91 involves SH2-phosphotyrosyl peptide interactions.

The possibility of an SH2 domain in Stat91 was indicated initially by the presence of highly conserved amino acid stretches between the Stat91 and Stat113 sequences in the 569 to 700 residue region, several of which, especially the FLLR sequence in the amino terminal end of the region, are characteristic of -SH2 domains. The C-terminal half of the SH2 domains are less well conserved in general (39); this was also true for the STAT proteins compared to other proteins, although Stat91 and Stat113 are quite similar in this region (38, 13, FIG. 23). The available structures of lck, src, abl, and p85a SH2's permit identification of structurally conserved regions (SCR's), and detailed alignment of amino acid sequences of several proteins (FIG. 23) is based on these.

The characteristic W (in βA1) is preceded by hydrophilic residues and is followed by hydrophobic residues in Stat91, but alignment to the W seems justified, even if the small beta sheet of which the W is part is shifted in Stat91. The three positively charged residues contributing to the phosphotyrosyl binding site are at the positions indicated as alphaA2, betaB5, and betaD5. FIG. 23 shows an alignment which accomplishes this by insertions in the 'AA' and 'CD' regions. This is a different alignment from that previously suggested (38), and gives a satisfactory alignment in the (beta)D region, although, like the previous alignment, it is obviously considerably less similar to the other SH2's in the C-terminus.

This alignment suggests that the SH2 domain in the Stat91 would end in the vicinity of residue 700. In such an alignment, the Tyr-701 occurs almost immediately after the SH2 domain: a distance too short to allow an intramolecular phosphotyrosine -SH2 interaction. Since the data presented earlier strongly implicate that an SH2-phosphotyrosine interaction is involved in dimerization, such an interaction is likely to be between two phospho Stat91 subunits as a reciprocal pTyr-SH2 interaction.

The apparent stability of Stat91 dimer may be due to a high association rate coupled with a high dissociation rate of SH2-phosphotyrosyl peptide interactions as suggested (Felder et al., 1993, Mol. Cell Biol. 13: 1449–1455) coupled with interactions between other domains of Stat91 that may contribute stability to the Stat91 dimer. Interference by homologous phosphopeptides with the -SH2-phosphotyrosine interaction would then lower stability sufficiently to allow complete dissociation and heterodimerization.

The dimer formation between phospho Stat91 is the first case in eukaryotes where dimer formation is regulated by phosphorylation, and the only one thus far dependent on tyrosine phosphorylation. We anticipate that dimerization with the STAT protein family will be important. It seems likely that in cells treated with IFN-α, there is Stat113-Stat91 interaction (15). This may well be mediated through SH2 and phosphotyrosyl peptide interactions as described above, leading to a complex (a probable dimer of Stat91-Stat113) which joins with a 48 kD DNA binding protein (a member of another family of DNA binding factors) to make a complex capable of binding to a different DNA site. Furthermore, we have recently cloned two mouse cDNAs which encode other STAT family members that have conserved the same general structure features observed in the Stat91 and Stat1 13 molecules (see Example 5, Supra). (U.S. application Ser. No. 08/126,588, filed Sep. 29, 1993, which is specifically incorporated herein by reference in its entirety). Thus the specificity of STAT-ontaining complexes will almost surely be affected by which proteins are phosphorylated and then available for dimer formation.

The following is a list of references related to the above disclosure and particularly to the experimental procedures and discussions. The references are numbered to correspond to like number references that appear hereinabove.

1. Larner, A. C., Jonak, G., Cheng, Y. S., Korant, B., Knight, E. and Darnell, J. E., Jr. (1984). *Proc. Natl. Acad. Sci. USA* 81: 6733–6737; Larner, A. C., Chaudhuri, A. and Darnell, J. E. (1986). *J. Biol. Chem.* 261: 453–459.
2. Friedman, R. L., Manly, S. P., McMahon, M., Kerr, I. M. and Stark, G. R. (1984). *Cell* 38: 745–755.
3. Levy, D. E., Kessler, D. S., Pine, R., Reich, N. and Darnell, J. E. (1988). *Genes & Dev.* 2: 383–392.
4. Levy, D. E., Kessler, D. S., Pine, R., and Darnell, J. E. (1989). *Genes & Dev.* 3: 1362–1371.
5. Dale, T. C., Iman, A. M. A., Kerr, I. M. and Stark, G. R. (1989). *Proc. Nat. Acad. Sci.* 86: 1203–1207.
6. Kessler, D. S., Veals, S. A., Fu, X. -Y., and Levy, D. E. (1990). *Genes & Dev.* 4: 1753–1765.
7. Fu, X. -Y., Kessler, D. S., Veals, S. A., Levy, D. E. and Darnell, J. E. (1990). *Proc. Natl. Acad. Sci. USA* 87: 8555–8559.
8. Lew, D. J., Decker, T., and Darnell, J. E. (1989). *Mol. Cell. Biol.* 9: 5404–5411.
9. Decker, T., Lew, D. J., Cheng, Y.-S., Levy, D. E. and Darnell, J. E. (1989). *EMBO J.* 8: 2009–2014.
10. Decker, T., Lew, D. J., Mirkovitch, J. and Darnell, J. E., 1991. *EMBO J.* 10: 927–932.
11. Veals, S. A., Schindler, C. W., Fu, X. -Y., Leonard, D., Darnell, J. E. and Levy, D. E. (1992). *Mol. Cell. Biol.* 12.
12. Schindler, C., Fu, X. -Y., Improta, T., Aebersold, R. and Darnell, J. E. (1992). *Proc. Natl. Acad. Sci. USA* 89: 7836–7389.
13. Fu, X. -Y., Schindler, C., Improta, T., Aebersold, R. and Darnell, J. E. (1992). *Proc. Natl. Acad. Sci. USA* 89: 7840–7389.
14. Lew, D. J., Decker, T. and Darnell, J. E. (1991). *Mol. Cell. Biol.* 11: 182–191.
15. Schindler, C., Shuai, K., Fu, X. -Y., Prezioso, V. and Darnell, J. E. (1992). *Science* 257: 809–812.
16. Garner, M. M. and Revan, A. (1981). *Nuc. Acids Res.* 9: 3047–3059; Fried, A., and Crothers, D. M. (1981) *ibid* 6505–6525.
17. Celis, J. E., Justessen, J., Madsun, P. S., Lovmand, J., Ratz, G. P. and Celis, A. (1987). *Leukemia* 1: 800–813.
18. Chodosh, L. A., Carthew, R. W. and Sharp, P. A. (1986). *Mol. Cell. Biol.* 6: 4723–4733.
19. Reich, N. and Pfeffer, L. M. (1990). *Proc. Natl. Acad. Sci. USA* 87: 8761–8765.
20. Kessler, D. S. and levy, D. (1991). *J. Biol. Chem.* 266: 23471–23476.
21. Levy, D., and Darnell, J. E. (1990). *The New Biologist* 2: 923–928.
22. Aguet, J. M., Denbie, Z. and Merlin, G. (1986). *Cell* 55: 273–280.
23. Kaplan, D. R., Martin-Zanca, D. and Parada, L. F. (1991). *Nature* 350: 158–160; Hempstead, G., Kapland, D., Marin-Zanca, D., Parada, L. F. and Chao, M. (1991). *Nature* 350: 678–683.
24. Veillette, A., Bookman, M. A., Horak, E. M., and Bolen, J. B. (1988). *Cell* 55: 301–308; Rudd, C. E. et al. (1988). *Proc. Natl. Acad. Sci. USA* 85: 5190–5194.
25. Evans, R. K., Johnson, J. D. and Haley, B. E. (1986). *Proc. Natl. Acad. Sci. USA* 83: 5382–5386.
26. Walaas, S. I. and Nairn, A. C. (1989). *J. of Mol. Neurosci.* 1: 117–127.
28. Pellegrini, S., John, J., Shearer, M., Kerr, I. M., and Stark, G. R. (1989). *Mol. Cell. Biol.* 9: 4605.
29. McKendry, R. et al. (1991). *Proc. Natl. Acad. Sci. U.S.A.* 88: 11455.
30. Muller, M. et al. (1993), *EMBO. J.*
31. Shuai, K., Schindler, C., Prezioso, V., and Darnell, J. E., Jr. (1992). *Science* 258: 1808.
32. Boyle, W. J., van der Geer, and Hunter, T. (1991). *Methods Enzymol.* 202: 110.
33. Walaas, S. I., and Nairn, A. C. (1989). *J. Mol. Neurosci.* 1: 117.
34. Khan, K. D. et al. (1993). *Proc. Natl. Acad. Sci. U.S.A.* 90: 6806.
35. Qufeshi, S. A. et al. (1991). *J. Biol. Chem.* 266: 20594.
36. Kawasaki, E., (1990). In *PRC Protcols: A Guide to Methods and Applications.* Innis, M., Gelfand, D., Sinisky, J., & White, T., Eds. (San Diego, Calif.: Academic Press), p. 119.
37. Brasier, A. R., Tata, J. E., and Habener, J. F. (1989). *Biotechniques* 7: 1116.
38. Fu, X. -Y. (1992). *Cell* 70: 323–335.
39. Koch, C. A., Anderson, D. Moran, M. F., Ellis, C. and Pawson, T. (1991). *Science* 252: 668–674.
40. Waksman, G. et al. (1992). *Nature* 358: 646–653.
41. Overduin, M. Rios, C. B., Mayer, B. J., Baltimore, D. and Cowburn, D. (1992). *Cell* 70: 697–704.
42. Velazquez et al. (1992). *Cell* 70: 313.
43. Muller et al. (1993). *Nature* 366: 129–135.
44. Watling et al. (1993). *Nature* 366: 166.
45. Shuai, K., Stark, G. R., Kerr, I. M., and Darnell, J. E. (1993). *Science* 261: 1744.
46. Dignam et al. (1983). *Nucl. Acids Res.* 11: 1475.
47. Davis, B. J. (1964). *Ann. N.Y. Acad. Sci.* 121: 404.
48. Bryan, J. K. (1977). *Anal. Biochem.* 78: 513.
49. Amster-Choder, O. and Wright, A. (1992). *Science* 257: 1395.
50. Songyang, Z., Shoelson, S. E., Chaudhuri, M., Gish, G., Pawson, T., Haser, W. G., King, F., Roberts, T., Ratnofsky, et al. (1993). *Cell* 72: 767.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

What is claimed is:

1. An isolated nucleic acid encoding a receptor recognition factor (RRF) selected from the group consisting of Stat1α, and Stat1β.

2. The isolated nucleic acid of claim 1 wherein the RRF contains one or more of the boxed regions in FIG. 8B.

3. A recombinant DNA molecule comprising a DNA sequence encoding a receptor recognition factor (RRF) selected from the group consisting of Stat1α, and Stat1β.

4. The recombinant DNA molecule of claim 3 wherein said receptor recognition factor is a Stat1α having the amino acid sequence of SEQ ID NO:4.

5. The recombinant DNA molecule of claim 4 wherein the DNA sequence is the coding region of SEQ ID NO:3.

6. The recombinant DNA molecule of claim 3 wherein said receptor recognition factor is a Stat1α having the amino acid sequence of SEQ ID NO:8.

7. The recombinant DNA molecule of claim 6 wherein the DNA sequence is the coding region of SEQ ID NO;7.

8. The recombinant DNA molecule of claim 3 wherein said receptor recognition factor is a Stat1β having the amino acid sequence of SEQ ID NO:6.

9. The recombinant DNA molecule of claim 8 wherein the DNA sequence is the coding region of SEQ ID NO:5.

10. The recombinant DNA molecule of claim 3 wherein the RRF contains one or more of the boxed regions in FIG. 8B.

11. The recombinant DNA molecule of claim 10 wherein the RRF comprises a highly negative charged domain at its C-terminal end.

12. The recombinant DNA molecule of claim 10 wherein the RRF comprises an SH2 domain.

13. The recombinant DNA molecule of claim 12 wherein the SH2 domain contains an arginine at an amino acid corresponding to 602 of SEQ ID NO:4.

14. The recombinant DNA molecule of claim 10 wherein said DNA sequence is operatively linked to an expression control sequence.

15. An expression vector containing the recombinant DNA molecule of claim 14.

16. A method of expressing a recombinant receptor recognition factor in a cell containing the expression vector of claim 15 comprising culturing the cell in an appropriate cell culture medium under conditions that provide for expression of the receptor recognition factor by the cell, wherein said receptor recognition factor is selected from the group consisting of Stat1α, and Stat1β.

17. The method of claim 16 further comprising the step of purifying the recombinant receptor recognition factor.

18. The method of claim 16 wherein said receptor recognition factor is a Stat1α having the amino acid sequence of SEQ ID NO:4.

19. The method of claim 16 wherein said receptor recognition factor is a Stat1α having the amino acid sequence of SEQ ID NO:8.

20. The method of claim 16 wherein said receptor recognition factor is a Stat1β having the amino acid sequence of SEQ ID NO:6.

21. A recombinant DNA molecule encoding a Stat1α or Stat1β, wherein the recombinant DNA molecule hybridizes under standard hybridization conditions of 5X SSC and 65° C. to a nucleic acid complementary to a DNA sequence selected from the group consisting of SEQ ID NO:3, SEQ ID NO:5, and SEQ ID NO:7.

22. The recombinant DNA molecule of claim 21 wherein the nucleic acid is complementary to the DNA sequence of SEQ ID NO:3.

23. The recombinant DNA molecule of claim 21 wherein the nucleic acid is complementary to the DNA sequence of SEQ ID NO:5.

24. The recombinant DNA molecule of claim 21 wherein the nucleic acid is complementary to the DNA sequence of SEQ ID NO:7.

25. A recombinant DNA molecule comprising the coding region of a DNA sequence encoding a receptor recognition factor (RRF); wherein the DNA sequence is selected from the group consisting of SEQ ID NO:3, SEQ ID NO:5, and SEQ ID NO:7; and wherein the coding region of the DNA sequence is operatively linked to an expression control sequence.

26. An expression vector containing the recombinant DNA molecule of claim 25.

27. A method of expressing a recombinant receptor recognition factor in a cell containing the expression vector of claim 26 comprising culturing the cell in an appropriate cell culture medium under conditions that provide for expression of the receptor recognition factor by the cell.

28. The method of claim 27 further comprising the step of purifying the recombinant receptor recognition factor.

29. A recombinant DNA molecule comprising 25 contiguous nucleotides from a nucleic acid encoding a Stat1α or Stat1β receptor recognition factor, wherein said nucleic acid has a nucleotide sequence selected from the group consisting of the coding region of SEQ ID NO:3, the coding region of SEQ ID NO:5, and the coding region of SEQ ID NO:7.

30. The recombinant DNA molecule of claim 29 wherein said nucleic acid has the nucleotide sequence of the coding region of SEQ ID NO:3.

31. The recombinant DNA molecule of claim 29 wherein said nucleic acid has the nucleotide sequence of the coding region of SEQ ID NO:5.

32. The recombinant DNA molecule of claim 29 wherein said nucleic acid has the nucleotide sequence of the coding region of SEQ ID NO:7.

33. The recombinant DNA molecule of claim 29 that is operatively linked to an expression control sequence.

34. An expression vector containing the recombinant DNA molecule of claim 33.

35. A method of expressing a recombinant receptor recognition factor in a cell containing the expression vector of claim 34 comprising culturing the cell in an appropriate cell culture medium under conditions that provide for expression of the receptor recognition factor by the cell.

36. The method of claim 35 further comprising the step of purifying the recombinant receptor recognition factor.

* * * * *

UNITED STATES PATENT AND TRADEMARK OFFICE
CERTIFICATE OF CORRECTION

PATENT NO.   : 5,976,835
DATED        : November 2, 1999
INVENTOR(S)  : James E. Darnell, Jr.; Christian W. Schindler; Xin-Yuan Fu; Zilong Wen; and Zhong Zhong It is certified that error appears in the above-identified patent and that said Letters Patent is hereby corrected as shown below:

ON THE TITLE PAGE:

Item [75]

The Inventorship of this Application has been changed by deletion of Zilong Wen and Zhong Zhong. The Inventors are: James E. Darnell, Jr.; Christian W. Schindler; and Xin-Yuan Fu.

Signed and Sealed this

Eighth Day of August, 2000

Attest:

Q. TODD DICKINSON

Attesting Officer

Director of Patents and Trademarks

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
      (A) LENGTH: 3268 base pairs
      (B) TYPE: nucleic acid
      (C) STRANDEDNESS: both
      (D) TOPOLOGY: unknown (ii) MOLECULE TYPE: cDNA (iii) HYPOTHETICAL: NO (iv) ANTI-SENSE: NO (vi) ORIGINAL SOURCE:
      (A) ORGANISM: Homo sapiens (vii) IMMEDIATE SOURCE:
      (B) CLONE: HeLa (ix) FEATURE:
      (A) NAME/KEY: CDS
      (B) LOCATION: 25..2577

(xi) SEQUENCE DESCRIPTION: SEQ ID NO:1:

```
ACTGCAACCC TAATCAGAGC CCAA ATG GCG CAG TGG GAA ATG CTG CAG AAT         51
                          Met Ala Gln Trp Glu Met Leu Gln Asn
                           1               5

CTT GAC AGC CCC TTT CAG GAT CAG CTG CAC CAG CTT TAC TCG CAC AGC         99
Leu Asp Ser Pro Phe Gln Asp Gln Leu His Gln Leu Tyr Ser His Ser
 10                  15                  20                  25

CTC CTG CCT GTG GAC ATT CGA CAG TAC TTG GCT GTC TGG ATT GAA GAC        147
Leu Leu Pro Val Asp Ile Arg Gln Tyr Leu Ala Val Trp Ile Glu Asp
                 30                  35                  40

CAG AAC TGG CAG GAA GCT GCA CTT GGG AGT GAT GAT TCC AAG GCT ACC        195
Gln Asn Trp Gln Glu Ala Ala Leu Gly Ser Asp Asp Ser Lys Ala Thr
             45                  50                  55

ATG CTA TTC TTC CAC TTC TTG GAT CAG CTG AAC TAT GAG TGT GGC CGT        243
Met Leu Phe Phe His Phe Leu Asp Gln Leu Asn Tyr Glu Cys Gly Arg
         60                  65                  70

TGC AGC CAG GAC CCA GAG TCC TTG TTG CTG CAG CAC AAT TTG CGG AAA        291
Cys Ser Gln Asp Pro Glu Ser Leu Leu Leu Gln His Asn Leu Arg Lys
     75                  80                  85

TTC TGC CGG GAC ATT CAG CCC TTT TCC CAG GAT CCT ACC CAG TTG GCT        339
Phe Cys Arg Asp Ile Gln Pro Phe Ser Gln Asp Pro Thr Gln Leu Ala
 90                  95                 100                 105

GAG ATG ATC TTT AAC CTC CTT CTG GAA GAA AAA AGA ATT TTG ATC CAG        387
Glu Met Ile Phe Asn Leu Leu Leu Glu Glu Lys Arg Ile Leu Ile Gln
                110                 115                 120

GCT CAG AGG GCC CAA TTG GAA CAA GGA GAG CCA GTT CTC GAA ACA CCT        435
Ala Gln Arg Ala Gln Leu Glu Gln Gly Glu Pro Val Leu Glu Thr Pro
            125                 130                 135

GTG GAG AGC CAG CAA CAT GAG ATT GAA TCC CGG ATC CTG GAT TTA AGG        483
Val Glu Ser Gln Gln His Glu Ile Glu Ser Arg Ile Leu Asp Leu Arg
        140                 145                 150

GCT ATG ATG GAG AAG CTG GTA AAA TCC ATC AGC CAA CTG AAA GAC CAG        531
Ala Met Met Glu Lys Leu Val Lys Ser Ile Ser Gln Leu Lys Asp Gln
    155                 160                 165

CAG GAT GTC TTC TGC TTC CGA TAT AAG ATC CAG GCC AAA GGG AAG ACA        579
Gln Asp Val Phe Cys Phe Arg Tyr Lys Ile Gln Ala Lys Gly Lys Thr
```

-continued

```
     170                 175                 180                 185
CCC TCT CTG GAC CCC CAT CAG ACC AAA GAG CAG AAG ATT CTG CAG GAA     627
Pro Ser Leu Asp Pro His Gln Thr Lys Glu Gln Lys Ile Leu Gln Glu
            190                 195                 200

ACT CTC AAT GAA CTG GAC AAA AGG AGA AAG GAG GTG CTG GAT GCC TCC     675
Thr Leu Asn Glu Leu Asp Lys Arg Arg Lys Glu Val Leu Asp Ala Ser
            205                 210                 215

AAA GCA CTG CTA GGC CGA TTA ACT ACC CTA ATC GAG CTA CTG CCA         723
Lys Ala Leu Leu Gly Arg Leu Thr Thr Leu Ile Glu Leu Leu Pro
            220                 225                 230

AAG TTG GAG GAG TGG AAG GCC CAG CAG CAA AAA GCC TGC ATC AGA GCT     771
Lys Leu Glu Glu Trp Lys Ala Gln Gln Gln Lys Ala Cys Ile Arg Ala
            235                 240                 245

CCC ATT GAC CAC GGG TTG GAA CAG CTG GAG ACA TGG TTC ACA GCT GGA     819
Pro Ile Asp His Gly Leu Glu Gln Leu Glu Thr Trp Phe Thr Ala Gly
250                 255                 260                 265

GCA AAG CTG TTG TTT CAC CTG AGG CAG CTG CTG AAG GAG CTG AAG GGA     867
Ala Lys Leu Leu Phe His Leu Arg Gln Leu Leu Lys Glu Leu Lys Gly
                270                 275                 280

CTG AGT TGC CTG GTT AGC TAT CAG GAT GAC CCT CTG ACC AAA GGG GTG     915
Leu Ser Cys Leu Val Ser Tyr Gln Asp Asp Pro Leu Thr Lys Gly Val
            285                 290                 295

GAC CTA CGC AAC GCC CAG GTC ACA GAG TTG CTA CAG CGT CTG CTC CAC     963
Asp Leu Arg Asn Ala Gln Val Thr Glu Leu Leu Gln Arg Leu Leu His
            300                 305                 310

AGA GCC TTT GTG GTA GAA ACC CAG CCC TGC ATG CCC CAA ACT CCC CAT    1011
Arg Ala Phe Val Val Glu Thr Gln Pro Cys Met Pro Gln Thr Pro His
            315                 320                 325

CGA CCC CTC ATC CTC AAG ACT GGC AGC AAG TTC ACC GTC CGA ACA AGG    1059
Arg Pro Leu Ile Leu Lys Thr Gly Ser Lys Phe Thr Val Arg Thr Arg
330                 335                 340                 345

CTG CTG GTG AGA CTC CAG GAA GGC AAT GAG TCA CTG ACT GTG GAA GTC    1107
Leu Leu Val Arg Leu Gln Glu Gly Asn Glu Ser Leu Thr Val Glu Val
                350                 355                 360

TCC ATT GAC AGG AAT CCT CCT CAA TTA CAA GGC TTC CGG AAG TTC AAC    1155
Ser Ile Asp Arg Asn Pro Pro Gln Leu Gln Gly Phe Arg Lys Phe Asn
            365                 370                 375

ATT CTG ACT TCA AAC CAG AAA ACT TTG ACC CCC GAG AAG GGG CAG AGT    1203
Ile Leu Thr Ser Asn Gln Lys Thr Leu Thr Pro Glu Lys Gly Gln Ser
            380                 385                 390

CAG GGT TTG ATT TGG GAC TTT GGT TAC CTG ACT CTG GTG GAG CAA CGT    1251
Gln Gly Leu Ile Trp Asp Phe Gly Tyr Leu Thr Leu Val Glu Gln Arg
395                 400                 405

TCA GGT GGT TCA GGA AAG GGC AGC AAT AAG GGG CCA CTA GGT GTG ACA    1299
Ser Gly Gly Ser Gly Lys Gly Ser Asn Lys Gly Pro Leu Gly Val Thr
410                 415                 420                 425

GAG GAA CTG CAC ATC ATC AGC TTC ACG GTC AAA TAT ACC TAC CAG GGT    1347
Glu Glu Leu His Ile Ile Ser Phe Thr Val Lys Tyr Thr Tyr Gln Gly
                430                 435                 440

CTG AAG CAG GAG CTG AAA ACG GAC ACC CTC CCT GTG GTG ATT ATT TCC    1395
Leu Lys Gln Glu Leu Lys Thr Asp Thr Leu Pro Val Val Ile Ile Ser
            445                 450                 455

AAC ATG AAC CAG CTC TCA ATT GCC TGG GCT TCA GTT CTC TGG TTC AAT    1443
Asn Met Asn Gln Leu Ser Ile Ala Trp Ala Ser Val Leu Trp Phe Asn
            460                 465                 470

TTG CTC AGC CCA AAC CTT CAG AAC CAG CAG TTC TTC TCC AAC CCC CCC    1491
Leu Leu Ser Pro Asn Leu Gln Asn Gln Gln Phe Phe Ser Asn Pro Pro
            475                 480                 485

AAG GCC CCC TGG AGC TTG CTG GGC CCT GCT CTC AGT TGG CAG TTC TCC    1539
Lys Ala Pro Trp Ser Leu Leu Gly Pro Ala Leu Ser Trp Gln Phe Ser
```

-continued

| | | | | | | | | | | | | | | | |
|---|---|---|---|---|---|---|---|---|---|---|---|---|---|---|---|
| 490 | | | | | 495 | | | | | 500 | | | | | 505 |

```
TCC TAT GTT GGC CGA GGC CTC AAC TCA GAC CAG CTG AGC ATG CTG AGA     1587
Ser Tyr Val Gly Arg Gly Leu Asn Ser Asp Gln Leu Ser Met Leu Arg
            510                 515                 520

AAC AAG CTG TTC GGG CAG AAC TGT AGG ACT GAG GAT CCA TTA TTG TCC     1635
Asn Lys Leu Phe Gly Gln Asn Cys Arg Thr Glu Asp Pro Leu Leu Ser
            525                 530                 535

TGG GCT GAC TTC ACT AAG CGA GAG AGC CCT CCT GGC AAG TTA CCA TTC     1683
Trp Ala Asp Phe Thr Lys Arg Glu Ser Pro Pro Gly Lys Leu Pro Phe
            540                 545                 550

TGG ACA TGG CTG GAC AAA ATT CTG GAG TTG GTA CAT GAC CAC CTG AAG     1731
Trp Thr Trp Leu Asp Lys Ile Leu Glu Leu Val His Asp His Leu Lys
        555                 560                 565

GAT CTC TGG AAT GAT GGA CGC ATC ATG GGC TTT GTG AGT CGG AGC CAG     1779
Asp Leu Trp Asn Asp Gly Arg Ile Met Gly Phe Val Ser Arg Ser Gln
570                 575                 580                 585

GAG CGC CGG CTG CTG AAG AAG ACC ATG TCT GGC ACC TTT CTA CTG CGC     1827
Glu Arg Arg Leu Leu Lys Lys Thr Met Ser Gly Thr Phe Leu Leu Arg
                590                 595                 600

TTC AGT GAA TCG TCA GAA GGG GGC ATT ACC TGC TCC TGG GTG GAG CAC     1875
Phe Ser Glu Ser Ser Glu Gly Gly Ile Thr Cys Ser Trp Val Glu His
            605                 610                 615

CAG GAT GAT GAC AAG GTG CTC ATC TAC TCT GTG CAA CCG TAC ACG AAG     1923
Gln Asp Asp Asp Lys Val Leu Ile Tyr Ser Val Gln Pro Tyr Thr Lys
            620                 625                 630

GAG GTG CTG CAG TCA CTC CCG CTG ACT GAA ATC ATC CGC CAT TAC CAG     1971
Glu Val Leu Gln Ser Leu Pro Leu Thr Glu Ile Ile Arg His Tyr Gln
    635                 640                 645

TTG CTC ACT GAG GAG AAT ATA CCT GAA AAC CCA CTG CGC TTC CTC TAT     2019
Leu Leu Thr Glu Glu Asn Ile Pro Glu Asn Pro Leu Arg Phe Leu Tyr
650                 655                 660                 665

CCC CGA ATC CCC CGG GAT GAA GCT TTT GGG TGC TAC TAC CAG GAG AAA     2067
Pro Arg Ile Pro Arg Asp Glu Ala Phe Gly Cys Tyr Tyr Gln Glu Lys
                670                 675                 680

GTT AAT CTC CAG GAA CGG AGG AAA TAC CTG AAA CAC AGG CTC ATT GTG     2115
Val Asn Leu Gln Glu Arg Arg Lys Tyr Leu Lys His Arg Leu Ile Val
            685                 690                 695

GTC TCT AAT AGA CAG GTG GAT GAA CTG CAA CAA CCG CTG GAG CTT AAG     2163
Val Ser Asn Arg Gln Val Asp Glu Leu Gln Gln Pro Leu Glu Leu Lys
        700                 705                 710

CCA GAG CCA GAG CTG GAG TCA TTA GAG CTG GAA CTA GGG CTG GTG CCA     2211
Pro Glu Pro Glu Leu Glu Ser Leu Glu Leu Glu Leu Gly Leu Val Pro
    715                 720                 725

GAG CCA GAG CTC AGC CTG GAC TTA GAG CCA CTG CTG AAG GCA GGG CTG     2259
Glu Pro Glu Leu Ser Leu Asp Leu Glu Pro Leu Leu Lys Ala Gly Leu
730                 735                 740                 745

GAT CTG GGG CCA GAG CTA GAG TCT GTG CTG GAG TCC ACT CTG GAG CCT     2307
Asp Leu Gly Pro Glu Leu Glu Ser Val Leu Glu Ser Thr Leu Glu Pro
                750                 755                 760

GTG ATA GAG CCC ACA CTA TGC ATG GTA TCA CAA ACA GTG CCA GAG CCA     2355
Val Ile Glu Pro Thr Leu Cys Met Val Ser Gln Thr Val Pro Glu Pro
            765                 770                 775

GAC CAA GGA CCT GTA TCA CAG CCA GTG CCA GAG CCA GAT TTG CCC TGT     2403
Asp Gln Gly Pro Val Ser Gln Pro Val Pro Glu Pro Asp Leu Pro Cys
            780                 785                 790

GAT CTG AGA CAT TTG AAC ACT GAG CCA ATG GAA ATC TTC AGA AAC TGT     2451
Asp Leu Arg His Leu Asn Thr Glu Pro Met Glu Ile Phe Arg Asn Cys
        795                 800                 805

GTA AAG ATT GAA GAA ATC ATG CCG AAT GGT GAC CCA CTG TTG GCT GGC     2499
Val Lys Ile Glu Glu Ile Met Pro Asn Gly Asp Pro Leu Leu Ala Gly
```

-continued

```
       810                 815                 820                 825
CAG AAC ACC GTG GAT GAG GTT TAC GTC TCC CGC CCC AGC CAC TTC TAC           2547
Gln Asn Thr Val Asp Glu Val Tyr Val Ser Arg Pro Ser His Phe Tyr
                830                 835                 840

ACT GAT GGA CCC TTG ATG CCT TCT GAC TTC TAGGAACCAC ATTTCCTCTG             2597
Thr Asp Gly Pro Leu Met Pro Ser Asp Phe
                845                 850

TTCTTTTCAT ATCTCTTTGC CCTTCCTACT CCTCATAGCA TGATATTGTT CTCCAAGGAT         2657

GGGAATCAGG CATGTGTCCC TTCCAAGCTG TGTTAACTGT TCAAACTCAG GCCTGTGTGA         2717

CTCCATTGGG GTGAGAGGTG AAAGCATAAC ATGGGTACAG AGGGGACAAC AATGAATCAG         2777

AACAGATGCT GAGCCATAGG TCTAAATAGG ATCCTGGAGG CTGCCTGCTG TGCTGGGAGG         2837

TATAGGGGTC CTGGGGCAG GCCAGGGCAG TTGACAGGTA CTTGGAGGGC TCAGGGCAGT          2897

GGCTTCTTTC CAGTATGGAA GGATTTCAAC ATTTTAATAG TTGGTTAGGC TAAACTGGTG         2957

CATACTGGCA TTGGCCTTGG TGGGAGCAC AGACACAGGA TAGGACTCCA TTTCTTTCTT          3017

CCATTCCTTC ATGTCTAGGA TAACTTGCTT TCTTCTTTCC TTTACTCCTG GCTCAAGCCC         3077

TGAATTTCTT CTTTTCCTGC AGGGGTTGAG AGCTTTCTGC CTTAGCCTAC CATGTGAAAC         3137

TCTACCCTGA AGAAAGGGAT GGATAGGAAG TAGACCTCTT TTTCTTACCA GTCTCCTCCC         3197

CTACTCTGCC CCCTAAGCTG GCTGTACCTG TTCCTCCCCC ATAAAATGAT CCTGCCAATC         3257

TAAAAAAAA A                                                               3268
```

(2) INFORMATION FOR SEQ ID NO:2:

(i) SEQUENCE CHARACTERISTICS:
        (A) LENGTH: 851 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Gln Trp Glu Met Leu Gln Asn Leu Asp Ser Pro Phe Gln Asp
 1               5                  10                  15

Gln Leu His Gln Leu Tyr Ser His Ser Leu Leu Pro Val Asp Ile Arg
                20                  25                  30

Gln Tyr Leu Ala Val Trp Ile Glu Asp Gln Asn Trp Gln Glu Ala Ala
            35                  40                  45

Leu Gly Ser Asp Asp Ser Lys Ala Thr Met Leu Phe Phe His Phe Leu
        50                  55                  60

Asp Gln Leu Asn Tyr Glu Cys Gly Arg Cys Ser Gln Asp Pro Glu Ser
    65                  70                  75                  80

Leu Leu Leu Gln His Asn Leu Arg Lys Phe Cys Arg Asp Ile Gln Pro
                85                  90                  95

Phe Ser Gln Asp Pro Thr Gln Leu Ala Glu Met Ile Phe Asn Leu Leu
                100                 105                 110

Leu Glu Glu Lys Arg Ile Leu Ile Gln Ala Gln Arg Ala Gln Leu Glu
            115                 120                 125

Gln Gly Glu Pro Val Leu Glu Thr Pro Val Glu Ser Gln Gln His Glu
        130                 135                 140

Ile Glu Ser Arg Ile Leu Asp Leu Arg Ala Met Met Glu Lys Leu Val
145                 150                 155                 160

Lys Ser Ile Ser Gln Leu Lys Asp Gln Gln Asp Val Phe Cys Phe Arg
                165                 170                 175

Tyr Lys Ile Gln Ala Lys Gly Lys Thr Pro Ser Leu Asp Pro His Gln
```

```
                    180                 185                 190
Thr Lys Glu Gln Lys Ile Leu Gln Glu Thr Leu Asn Glu Leu Asp Lys
                195                 200                 205
Arg Arg Lys Glu Val Leu Asp Ala Ser Lys Ala Leu Leu Gly Arg Leu
            210                 215                 220
Thr Thr Leu Ile Glu Leu Leu Pro Lys Leu Glu Glu Trp Lys Ala
225                 230                 235                 240
Gln Gln Gln Lys Ala Cys Ile Arg Ala Pro Ile Asp His Gly Leu Glu
                245                 250                 255
Gln Leu Glu Thr Trp Phe Thr Ala Gly Ala Lys Leu Leu Phe His Leu
            260                 265                 270
Arg Gln Leu Leu Lys Glu Leu Lys Gly Leu Ser Cys Leu Val Ser Tyr
        275                 280                 285
Gln Asp Asp Pro Leu Thr Lys Gly Val Asp Leu Arg Asn Ala Gln Val
    290                 295                 300
Thr Glu Leu Leu Gln Arg Leu Leu His Arg Ala Phe Val Val Glu Thr
305                 310                 315                 320
Gln Pro Cys Met Pro Gln Thr Pro His Arg Pro Leu Ile Leu Lys Thr
                325                 330                 335
Gly Ser Lys Phe Thr Val Arg Thr Arg Leu Leu Val Arg Leu Gln Glu
            340                 345                 350
Gly Asn Glu Ser Leu Thr Val Glu Val Ser Ile Asp Arg Asn Pro Pro
        355                 360                 365
Gln Leu Gln Gly Phe Arg Lys Phe Asn Ile Leu Thr Ser Asn Gln Lys
    370                 375                 380
Thr Leu Thr Pro Glu Lys Gly Gln Ser Gln Gly Leu Ile Trp Asp Phe
385                 390                 395                 400
Gly Tyr Leu Thr Leu Val Glu Gln Arg Ser Gly Ser Gly Lys Gly
                405                 410                 415
Ser Asn Lys Gly Pro Leu Gly Val Thr Glu Glu Leu His Ile Ile Ser
            420                 425                 430
Phe Thr Val Lys Tyr Thr Tyr Gln Gly Leu Lys Gln Glu Leu Lys Thr
        435                 440                 445
Asp Thr Leu Pro Val Val Ile Ile Ser Asn Met Asn Gln Leu Ser Ile
    450                 455                 460
Ala Trp Ala Ser Val Leu Trp Phe Asn Leu Leu Ser Pro Asn Leu Gln
465                 470                 475                 480
Asn Gln Gln Phe Phe Ser Asn Pro Pro Lys Ala Pro Trp Ser Leu Leu
                485                 490                 495
Gly Pro Ala Leu Ser Trp Gln Phe Ser Ser Tyr Val Gly Arg Gly Leu
            500                 505                 510
Asn Ser Asp Gln Leu Ser Met Leu Arg Asn Lys Leu Phe Gly Gln Asn
        515                 520                 525
Cys Arg Thr Glu Asp Pro Leu Leu Ser Trp Ala Asp Phe Thr Lys Arg
    530                 535                 540
Glu Ser Pro Pro Gly Lys Leu Pro Phe Trp Thr Trp Leu Asp Lys Ile
545                 550                 555                 560
Leu Glu Leu Val His Asp His Leu Lys Asp Leu Trp Asn Asp Gly Arg
                565                 570                 575
Ile Met Gly Phe Val Ser Arg Ser Gln Glu Arg Arg Leu Leu Lys Lys
            580                 585                 590
Thr Met Ser Gly Thr Phe Leu Leu Arg Phe Ser Glu Ser Ser Glu Gly
        595                 600                 605
```

```
Gly Ile Thr Cys Ser Trp Val Glu His Gln Asp Asp Lys Val Leu
    610                 615                 620
Ile Tyr Ser Val Gln Pro Tyr Thr Lys Glu Val Leu Gln Ser Leu Pro
625                 630                 635                 640
Leu Thr Glu Ile Ile Arg His Tyr Gln Leu Leu Thr Glu Glu Asn Ile
                645                 650                 655
Pro Glu Asn Pro Leu Arg Phe Leu Tyr Pro Arg Ile Pro Arg Asp Glu
            660                 665                 670
Ala Phe Gly Cys Tyr Tyr Gln Glu Lys Val Asn Leu Gln Glu Arg Arg
        675                 680                 685
Lys Tyr Leu Lys His Arg Leu Ile Val Val Ser Asn Arg Gln Val Asp
690                 695                 700
Glu Leu Gln Gln Pro Leu Glu Leu Lys Pro Glu Pro Glu Leu Glu Ser
705                 710                 715                 720
Leu Glu Leu Glu Leu Gly Leu Val Pro Glu Pro Glu Leu Ser Leu Asp
                725                 730                 735
Leu Glu Pro Leu Leu Lys Ala Gly Leu Asp Leu Gly Pro Glu Leu Glu
            740                 745                 750
Ser Val Leu Glu Ser Thr Leu Glu Pro Val Ile Glu Pro Thr Leu Cys
        755                 760                 765
Met Val Ser Gln Thr Val Pro Glu Pro Asp Gln Gly Pro Val Ser Gln
770                 775                 780
Pro Val Pro Glu Pro Asp Leu Pro Cys Asp Leu Arg His Leu Asn Thr
785                 790                 795                 800
Glu Pro Met Glu Ile Phe Arg Asn Cys Val Lys Ile Glu Glu Ile Met
                805                 810                 815
Pro Asn Gly Asp Pro Leu Leu Ala Gly Gln Asn Thr Val Asp Glu Val
            820                 825                 830
Tyr Val Ser Arg Pro Ser His Phe Tyr Thr Asp Gly Pro Leu Met Pro
        835                 840                 845
Ser Asp Phe
    850

(2) INFORMATION FOR SEQ ID NO:3:

(i) SEQUENCE CHARACTERISTICS:
        (A) LENGTH: 3943 base pairs
        (B) TYPE: nucleic acid
        (C) STRANDEDNESS: both
        (D) TOPOLOGY: unknown (ii) MOLECULE TYPE: cDNA (iii) HYPOTHETICAL: NO (iv) ANTI-SENSE: NO (vi) ORIGINAL SOURCE:
        (A) ORGANISM: Homo sapiens (vii) IMMEDIATE SOURCE:
        (B) CLONE: Human Stat91

(ix) FEATURE:
        (A) NAME/KEY: CDS
        (B) LOCATION: 197..2449

(xi) SEQUENCE DESCRIPTION: SEQ ID NO:3:

ATTAAACCTC TCGCCGAGCC CCTCCGCAGA CTCTGCGCCG GAAAGTTTCA TTTGCTGTAT        60

GCCATCCTCG AGAGCTGTCT AGGTTAACGT TCGCACTCTG TGTATATAAC CTCGACAGTC       120

TTGGCACCTA ACGTGCTGTG CGTAGCTGCT CCTTTGGTTG AATCCCCAGG CCCTTGTTGG       180
```

```
GGCACAAGGT GGCAGG ATG TCT CAG TGG TAC GAA CTT CAG CAG CTT GAC              229
               Met Ser Gln Trp Tyr Glu Leu Gln Gln Leu Asp
                 1               5                  10

TCA AAA TTC CTG GAG CAG GTT CAC CAG CTT TAT GAT GAC AGT TTT CCC            277
Ser Lys Phe Leu Glu Gln Val His Gln Leu Tyr Asp Asp Ser Phe Pro
         15                  20                  25

ATG GAA ATC AGA CAG TAC CTG GCA CAG TGG TTA GAA AAG CAA GAC TGG            325
Met Glu Ile Arg Gln Tyr Leu Ala Gln Trp Leu Glu Lys Gln Asp Trp
             30                  35                  40

GAG CAC GCT GCC AAT GAT GTT TCA TTT GCC ACC ATC CGT TTT CAT GAC            373
Glu His Ala Ala Asn Asp Val Ser Phe Ala Thr Ile Arg Phe His Asp
         45                  50                  55

CTC CTG TCA CAG CTG GAT GAT CAA TAT AGT CGC TTT TCT TTG GAG AAT            421
Leu Leu Ser Gln Leu Asp Asp Gln Tyr Ser Arg Phe Ser Leu Glu Asn
 60                  65                  70                  75

AAC TTC TTG CTA CAG CAT AAC ATA AGG AAA AGC AAG CGT AAT CTT CAG            469
Asn Phe Leu Leu Gln His Asn Ile Arg Lys Ser Lys Arg Asn Leu Gln
                 80                  85                  90

GAT AAT TTT CAG GAA GAC CCA ATC CAG ATG TCT ATG ATC ATT TAC AGC            517
Asp Asn Phe Gln Glu Asp Pro Ile Gln Met Ser Met Ile Ile Tyr Ser
             95                 100                 105

TGT CTG AAG GAA GAA AGG AAA ATT CTG GAA AAC GCC CAG AGA TTT AAT            565
Cys Leu Lys Glu Glu Arg Lys Ile Leu Glu Asn Ala Gln Arg Phe Asn
        110                 115                 120

CAG GCT CAG TCG GGG AAT ATT CAG AGC ACA GTG ATG TTA GAC AAA CAG            613
Gln Ala Gln Ser Gly Asn Ile Gln Ser Thr Val Met Leu Asp Lys Gln
    125                 130                 135

AAA GAG CTT GAC AGT AAA GTC AGA AAT GTG AAG GAC AAG GTT ATG TGT            661
Lys Glu Leu Asp Ser Lys Val Arg Asn Val Lys Asp Lys Val Met Cys
140                 145                 150                 155

ATA GAG CAT GAA ATC AAG AGC CTG GAA GAT TTA CAA GAT GAA TAT GAC            709
Ile Glu His Glu Ile Lys Ser Leu Glu Asp Leu Gln Asp Glu Tyr Asp
                160                 165                 170

TTC AAA TGC AAA ACC TTG CAG AAC AGA GAA CAC GAG ACC AAT GGT GTG            757
Phe Lys Cys Lys Thr Leu Gln Asn Arg Glu His Glu Thr Asn Gly Val
            175                 180                 185

GCA AAG AGT GAT CAG AAA CAA GAA CAG CTG TTA CTC AAG AAG ATG TAT            805
Ala Lys Ser Asp Gln Lys Gln Glu Gln Leu Leu Leu Lys Lys Met Tyr
        190                 195                 200

TTA ATG CTT GAC AAT AAG AGA AAG GAA GTA GTT CAC AAA ATA ATA GAG            853
Leu Met Leu Asp Asn Lys Arg Lys Glu Val Val His Lys Ile Ile Glu
205                 210                 215

TTG CTG AAT GTC ACT GAA CTT ACC CAG AAT GCC CTG ATT AAT GAT GAA            901
Leu Leu Asn Val Thr Glu Leu Thr Gln Asn Ala Leu Ile Asn Asp Glu
220                 225                 230                 235

CTA GTG GAG TGG AAG CGG AGA CAG CAG AGC GCC TGT ATT GGG GGG CCG            949
Leu Val Glu Trp Lys Arg Arg Gln Gln Ser Ala Cys Ile Gly Gly Pro
                240                 245                 250

CCC AAT GCT TGC TTG GAT CAG CTG CAG AAC TGG TTC ACT ATA GTT GCG            997
Pro Asn Ala Cys Leu Asp Gln Leu Gln Asn Trp Phe Thr Ile Val Ala
            255                 260                 265

GAG AGT CTG CAG CAA GTT CGG CAG CAG CTT AAA AAG TTG GAG GAA TTG           1045
Glu Ser Leu Gln Gln Val Arg Gln Gln Leu Lys Lys Leu Glu Glu Leu
        270                 275                 280

GAA CAG AAA TAC ACC TAC GAA CAT GAC CCT ATC ACA AAA AAC AAA CAA           1093
Glu Gln Lys Tyr Thr Tyr Glu His Asp Pro Ile Thr Lys Asn Lys Gln
285                 290                 295

GTG TTA TGG GAC CGC ACC TTC AGT CTT TTC CAG CAG CTC ATT CAG AGC           1141
Val Leu Trp Asp Arg Thr Phe Ser Leu Phe Gln Gln Leu Ile Gln Ser
300                 305                 310                 315
```

```
TCG TTT GTG GTG GAA AGA CAG CCC TGC ATG CCA ACG CAC CCT CAG AGG        1189
Ser Phe Val Val Glu Arg Gln Pro Cys Met Pro Thr His Pro Gln Arg
            320                 325                 330

CCG CTG GTC TTG AAG ACA GGG GTC CAG TTC ACT GTG AAG TTG AGA CTG        1237
Pro Leu Val Leu Lys Thr Gly Val Gln Phe Thr Val Lys Leu Arg Leu
            335                 340                 345

TTG GTG AAA TTG CAA GAG CTG AAT TAT AAT TTG AAA GTC AAA GTC TTA        1285
Leu Val Lys Leu Gln Glu Leu Asn Tyr Asn Leu Lys Val Lys Val Leu
            350                 355                 360

TTT GAT AAA GAT GTG AAT GAG AGA AAT ACA GTA AAA GGA TTT AGG AAG        1333
Phe Asp Lys Asp Val Asn Glu Arg Asn Thr Val Lys Gly Phe Arg Lys
            365                 370                 375

TTC AAC ATT TTG GGC ACG CAC ACA AAA GTG ATG AAC ATG GAG GAG TCC        1381
Phe Asn Ile Leu Gly Thr His Thr Lys Val Met Asn Met Glu Glu Ser
380                 385                 390                 395

ACC AAT GGC AGT CTG GCG GCT GAA TTT CGG CAC CTG CAA TTG AAA GAA        1429
Thr Asn Gly Ser Leu Ala Ala Glu Phe Arg His Leu Gln Leu Lys Glu
                    400                 405                 410

CAG AAA AAT GCT GGC ACC AGA ACG AAT GAG GGT CCT CTC ATC GTT ACT        1477
Gln Lys Asn Ala Gly Thr Arg Thr Asn Glu Gly Pro Leu Ile Val Thr
            415                 420                 425

GAA GAG CTT CAC TCC CTT AGT TTT GAA ACC CAA TTG TGC CAG CCT GGT        1525
Glu Glu Leu His Ser Leu Ser Phe Glu Thr Gln Leu Cys Gln Pro Gly
            430                 435                 440

TTG GTA ATT GAC CTC GAG ACG ACC TCT CTG CCC GTT GTG GTG ATC TCC        1573
Leu Val Ile Asp Leu Glu Thr Thr Ser Leu Pro Val Val Val Ile Ser
            445                 450                 455

AAC GTC AGC CAG CTC CCG AGC GGT TGG GCC TCC ATC CTT TGG TAC AAC        1621
Asn Val Ser Gln Leu Pro Ser Gly Trp Ala Ser Ile Leu Trp Tyr Asn
460                 465                 470                 475

ATG CTG GTG GCG GAA CCC AGG AAT CTG TCC TTC TTC CTG ACT CCA CCA        1669
Met Leu Val Ala Glu Pro Arg Asn Leu Ser Phe Phe Leu Thr Pro Pro
                    480                 485                 490

TGT GCA CGA TGG GCT CAG CTT TCA GAA GTG CTG AGT TGG CAG TTT TCT        1717
Cys Ala Arg Trp Ala Gln Leu Ser Glu Val Leu Ser Trp Gln Phe Ser
            495                 500                 505

TCT GTC ACC AAA AGA GGT CTC AAT GTG GAC CAG CTG AAC ATG TTG GGA        1765
Ser Val Thr Lys Arg Gly Leu Asn Val Asp Gln Leu Asn Met Leu Gly
            510                 515                 520

GAG AAG CTT CTT GGT CCT AAC GCC AGC CCC GAT GGT CTC ATT CCG TGG        1813
Glu Lys Leu Leu Gly Pro Asn Ala Ser Pro Asp Gly Leu Ile Pro Trp
525                 530                 535

ACG AGG TTT TGT AAG GAA AAT ATA AAT GAT AAA AAT TTT CCC TTC TGG        1861
Thr Arg Phe Cys Lys Glu Asn Ile Asn Asp Lys Asn Phe Pro Phe Trp
540                 545                 550                 555

CTT TGG ATT GAA AGC ATC CTA GAA CTC ATT AAA AAA CAC CTG CTC CCT        1909
Leu Trp Ile Glu Ser Ile Leu Glu Leu Ile Lys Lys His Leu Leu Pro
                    560                 565                 570

CTC TGG AAT GAT GGG TGC ATC ATG GGC TTC ATC AGC AAG GAG CGA GAG        1957
Leu Trp Asn Asp Gly Cys Ile Met Gly Phe Ile Ser Lys Glu Arg Glu
            575                 580                 585

CGT GCC CTG TTG AAG GAC CAG CAG CCG GGG ACC TTC CTG CTG CGG TTC        2005
Arg Ala Leu Leu Lys Asp Gln Gln Pro Gly Thr Phe Leu Leu Arg Phe
            590                 595                 600

AGT GAG AGC TCC CGG GAA GGG GCC ATC ACA TTC ACA TGG GTG GAG CGG        2053
Ser Glu Ser Ser Arg Glu Gly Ala Ile Thr Phe Thr Trp Val Glu Arg
            605                 610                 615

TCC CAG AAC GGA GGC GAA CCT GAC TTC CAT GCG GTT GAA CCC TAC ACG        2101
Ser Gln Asn Gly Gly Glu Pro Asp Phe His Ala Val Glu Pro Tyr Thr
620                 625                 630                 635
```

-continued

```
AAG AAA GAA CTT TCT GCT GTT ACT TTC CCT GAC ATC ATT CGC AAT TAC      2149
Lys Lys Glu Leu Ser Ala Val Thr Phe Pro Asp Ile Ile Arg Asn Tyr
                640                 645                 650

AAA GTC ATG GCT GCT GAG AAT ATT CCT GAG AAT CCC CTG AAG TAT CTG      2197
Lys Val Met Ala Ala Glu Asn Ile Pro Glu Asn Pro Leu Lys Tyr Leu
                655                 660                 665

TAT CCA AAT ATT GAC AAA GAC CAT GCC TTT GGA AAG TAT TAC TCC AGG      2245
Tyr Pro Asn Ile Asp Lys Asp His Ala Phe Gly Lys Tyr Tyr Ser Arg
                670                 675                 680

CCA AAG GAA GCA CCA GAG CCA ATG GAA CTT GAT GGC CCT AAA GGA ACT      2293
Pro Lys Glu Ala Pro Glu Pro Met Glu Leu Asp Gly Pro Lys Gly Thr
            685                 690                 695

GGA TAT ATC AAG ACT GAG TTG ATT TCT GTG TCT GAA GTT CAC CCT TCT      2341
Gly Tyr Ile Lys Thr Glu Leu Ile Ser Val Ser Glu Val His Pro Ser
700                 705                 710                 715

AGA CTT CAG ACC ACA GAC AAC CTG CTC CCC ATG TCT CCT GAG GAG TTT      2389
Arg Leu Gln Thr Thr Asp Asn Leu Leu Pro Met Ser Pro Glu Glu Phe
                720                 725                 730

GAC GAG GTG TCT CGG ATA GTG GGC TCT GTA GAA TTC GAC AGT ATG ATG      2437
Asp Glu Val Ser Arg Ile Val Gly Ser Val Glu Phe Asp Ser Met Met
                735                 740                 745

AAC ACA GTA TAGAGCATGA ATTTTTTTCA TCTTCTCTGG CGACAGTTTT              2486
Asn Thr Val
        750

CCTTCTCATC TGTGATTCCC TCCTGCTACT CTGTTCCTTC ACATCCTGTG TTTCTAGGGA    2546

AATGAAAGAA AGGCCAGCAA ATTCGCTGCA ACCTGTTGAT AGCAAGTGAA TTTTTCTCTA    2606

ACTCAGAAAC ATCAGTTACT CTGAAGGGCA TCATGCATCT TACTGAAGGT AAAATTGAAA    2666

GGCATTCTCT GAAGAGTGGG TTTCACAAGT GAAAAACATC CAGATACACC CAAAGTATCA    2726

GGACGAGAAT GAGGGTCCTT TGGGAAAGGA GAAGTTAAGC AACATCTAGC AAATGTTATG    2786

CATAAAGTCA GTGCCCAACT GTTATAGGTT GTTGGATAAA TCAGTGGTTA TTTAGGGAAC    2846

TGCTTGACGT AGGAACGGTA AATTTCTGTG GGAGAATTCT TACATGTTTT CTTTGCTTTA    2906

AGTGTAACTG GCAGTTTTCC ATTGGTTTAC CTGTGAAATA GTTCAAAGCC AAGTTTATAT    2966

ACAATTATAT CAGTCCTCTT TCAAAGGTAG CCATCATGGA TCTGGTAGGG GGAAAATGTG    3026

TATTTTATTA CATCTTTCAC ATTGGCTATT TAAAGACAAA GACAAATTCT GTTTCTTGAG    3086

AAGAGAACAT TTCCAAATTC ACAAGTTGTG TTTGATATCC AAAGCTGAAT ACATTCTGCT    3146

TTCATCTTGG TCACATACAA TTATTTTTAC AGTTCTCCCA AGGGAGTTAG CTATTCACA    3206

ACCACTCATT CAAAAGTTGA AATTAACCAT AGATGTAGAT AAACTCAGAA ATTTAATTCA    3266

TGTTTCTTAA ATGGGCTACT TTGTCCTTTT TGTTATTAGG GTGGTATTTA GTCTATTAGC    3326

CACAAAATTG GGAAAGGAGT AGAAAAAGCA GTAACTGACA ACTTGAATAA TACACCAGAG    3386

ATAATATGAG AATCAGATCA TTTCAAAACT CATTTCCTAT GTAACTGCAT TGAGAACTGC    3446

ATATGTTTCG CTGATATATG TGTTTTTCAC ATTTGCGAAT GGTTCCATTC TCTCTCCTGT    3506

ACTTTTTCCA GACACTTTTT TGAGTGGATG ATGTTTCGTG AAGTATACTG TATTTTTACC    3566

TTTTTCCTTC CTTATCACTG ACACAAAAAG TAGATTAAGA GATGGGTTTG ACAAGGTTCT    3626

TCCCTTTTAC ATACTGCTGT CTATGTGGCT GTATCTTGTT TTTCCACTAC TGCTACCACA    3686

ACTATATTAT CATGCAAATG CTGTATTCTT CTTTGGTGGA GATAAAGATT TCTTGAGTTT    3746

TGTTTTAAAA TTAAAGCTAA AGTATCTGTA TTGCATTAAA TATAATATCG ACACAGTGCT    3806

TTCCGTGGCA CTGCATACAA TCTGAGGCCT CCTCTCTCAG TTTTTATATA GATGGCGAGA    3866

ACCTAAGTTT CAGTTGATTT TACAATTGAA ATGACTAAAA AACAAAGAAG ACAACATTAA    3926
```

AAACAATATT GTTTCTA                                                      3943

(2) INFORMATION FOR SEQ ID NO:4:

(i) SEQUENCE CHARACTERISTICS:
       (A) LENGTH: 750 amino acids
       (B) TYPE: amino acid
       (D) TOPOLOGY: linear (ii) MOLECULE TYPE: protein (xi) SEQUENCE DESCRIPTION: SEQ ID NO:4:

Met Ser Gln Trp Tyr Glu Leu Gln Gln Leu Asp Ser Lys Phe Leu Glu
 1               5                  10                  15

Gln Val His Gln Leu Tyr Asp Asp Ser Phe Pro Met Glu Ile Arg Gln
            20                  25                  30

Tyr Leu Ala Gln Trp Leu Glu Lys Gln Asp Trp Glu His Ala Ala Asn
        35                  40                  45

Asp Val Ser Phe Ala Thr Ile Arg Phe His Asp Leu Leu Ser Gln Leu
 50                  55                  60

Asp Asp Gln Tyr Ser Arg Phe Ser Leu Glu Asn Asn Phe Leu Leu Gln
 65                  70                  75                  80

His Asn Ile Arg Lys Ser Lys Arg Asn Leu Gln Asp Asn Phe Gln Glu
            85                  90                  95

Asp Pro Ile Gln Met Ser Met Ile Ile Tyr Ser Cys Leu Lys Glu Glu
           100                 105                 110

Arg Lys Ile Leu Glu Asn Ala Gln Arg Phe Asn Gln Ala Gln Ser Gly
       115                 120                 125

Asn Ile Gln Ser Thr Val Met Leu Asp Lys Gln Lys Glu Leu Asp Ser
130                 135                 140

Lys Val Arg Asn Val Lys Asp Lys Val Met Cys Ile Glu His Glu Ile
145                 150                 155                 160

Lys Ser Leu Glu Asp Leu Gln Asp Glu Tyr Asp Phe Lys Cys Lys Thr
           165                 170                 175

Leu Gln Asn Arg Glu His Glu Thr Asn Gly Val Ala Lys Ser Asp Gln
       180                 185                 190

Lys Gln Glu Gln Leu Leu Leu Lys Lys Met Tyr Leu Met Leu Asp Asn
    195                 200                 205

Lys Arg Lys Glu Val Val His Lys Ile Ile Glu Leu Leu Asn Val Thr
210                 215                 220

Glu Leu Thr Gln Asn Ala Leu Ile Asn Asp Glu Leu Val Glu Trp Lys
225                 230                 235                 240

Arg Arg Gln Gln Ser Ala Cys Ile Gly Gly Pro Pro Asn Ala Cys Leu
           245                 250                 255

Asp Gln Leu Gln Asn Trp Phe Thr Ile Val Ala Glu Ser Leu Gln Gln
       260                 265                 270

Val Arg Gln Gln Leu Lys Lys Leu Glu Glu Leu Glu Gln Lys Tyr Thr
    275                 280                 285

Tyr Glu His Asp Pro Ile Thr Lys Asn Lys Gln Val Leu Trp Asp Arg
290                 295                 300

Thr Phe Ser Leu Phe Gln Gln Leu Ile Gln Ser Ser Phe Val Val Glu
305                 310                 315                 320

Arg Gln Pro Cys Met Pro Thr His Pro Gln Arg Pro Leu Val Leu Lys
           325                 330                 335

Thr Gly Val Gln Phe Thr Val Lys Leu Arg Leu Leu Val Lys Leu Gln
       340                 345                 350

```
Glu Leu Asn Tyr Asn Leu Lys Val Lys Val Leu Phe Asp Lys Asp Val
            355                 360                 365

Asn Glu Arg Asn Thr Val Lys Gly Phe Arg Lys Phe Asn Ile Leu Gly
370                 375                 380

Thr His Thr Lys Val Met Asn Met Glu Glu Ser Thr Asn Gly Ser Leu
385                 390                 395                 400

Ala Ala Glu Phe Arg His Leu Gln Leu Lys Gln Lys Asn Ala Gly
                405                 410                 415

Thr Arg Thr Asn Glu Gly Pro Leu Ile Val Thr Glu Leu His Ser
                420                 425                 430

Leu Ser Phe Glu Thr Gln Leu Cys Gln Pro Gly Leu Val Ile Asp Leu
            435                 440                 445

Glu Thr Thr Ser Leu Pro Val Val Ile Ser Asn Val Ser Gln Leu
            450                 455                 460

Pro Ser Gly Trp Ala Ser Ile Leu Trp Tyr Asn Met Leu Val Ala Glu
465                 470                 475                 480

Pro Arg Asn Leu Ser Phe Phe Leu Thr Pro Pro Cys Ala Arg Trp Ala
                485                 490                 495

Gln Leu Ser Glu Val Leu Ser Trp Gln Phe Ser Ser Val Thr Lys Arg
            500                 505                 510

Gly Leu Asn Val Asp Gln Leu Asn Met Leu Gly Glu Lys Leu Leu Gly
            515                 520                 525

Pro Asn Ala Ser Pro Asp Gly Leu Ile Pro Trp Thr Arg Phe Cys Lys
530                 535                 540

Glu Asn Ile Asn Asp Lys Asn Phe Pro Phe Trp Leu Trp Ile Glu Ser
545                 550                 555                 560

Ile Leu Glu Leu Ile Lys Lys His Leu Leu Pro Leu Trp Asn Asp Gly
                565                 570                 575

Cys Ile Met Gly Phe Ile Ser Lys Glu Arg Glu Arg Ala Leu Leu Lys
                580                 585                 590

Asp Gln Gln Pro Gly Thr Phe Leu Leu Arg Phe Ser Glu Ser Ser Arg
            595                 600                 605

Glu Gly Ala Ile Thr Phe Thr Trp Val Glu Arg Ser Gln Asn Gly Gly
610                 615                 620

Glu Pro Asp Phe His Ala Val Glu Pro Tyr Thr Lys Lys Glu Leu Ser
625                 630                 635                 640

Ala Val Thr Phe Pro Asp Ile Ile Arg Asn Tyr Lys Val Met Ala Ala
                645                 650                 655

Glu Asn Ile Pro Glu Asn Pro Leu Lys Tyr Leu Tyr Pro Asn Ile Asp
                660                 665                 670

Lys Asp His Ala Phe Gly Lys Tyr Tyr Ser Arg Pro Lys Glu Ala Pro
            675                 680                 685

Glu Pro Met Glu Leu Asp Gly Pro Lys Gly Thr Gly Tyr Ile Lys Thr
            690                 695                 700

Glu Leu Ile Ser Val Ser Glu Val His Pro Ser Arg Leu Gln Thr Thr
705                 710                 715                 720

Asp Asn Leu Leu Pro Met Ser Pro Glu Glu Phe Asp Glu Val Ser Arg
                725                 730                 735

Ile Val Gly Ser Val Glu Phe Asp Ser Met Met Asn Thr Val
                740                 745                 750
```

(2) INFORMATION FOR SEQ ID NO:5:

(i) SEQUENCE CHARACTERISTICS:

-continued

```
         (A) LENGTH: 2607 base pairs
         (B) TYPE: nucleic acid
         (C) STRANDEDNESS: both
         (D) TOPOLOGY: unknown (ii) MOLECULE TYPE: cDNA (iii) HYPOTHETICAL: NO (iv) ANTI-SENSE: NO (vi) ORIGINAL SOURCE:
         (A) ORGANISM: Homo sapiens (ix) FEATURE:
         (A) NAME/KEY: CDS
         (B) LOCATION: 197..2335

(xi) SEQUENCE DESCRIPTION: SEQ ID NO:5:
```

| | |
|---|---:|
| ATTAAACCTC TCGCCGAGCC CCTCCGCAGA CTCTGCGCCG GAAAGTTTCA TTTGCTGTAT | 60 |
| GCCATCCTCG AGAGCTGTCT AGGTTAACGT TCGCACTCTG TGTATATAAC CTCGACAGTC | 120 |
| TTGGCACCTA ACGTGCTGTG CGTAGCTGCT CCTTTGGTTG AATCCCCAGG CCCTTGTTGG | 180 |

```
GGCACAAGGT GGCAGG ATG TCT CAG TGG TAC GAA CTT CAG CAG CTT GAC          229
               Met Ser Gln Trp Tyr Glu Leu Gln Gln Leu Asp
                 1               5                  10

TCA AAA TTC CTG GAG CAG GTT CAC CAG CTT TAT GAT GAC AGT TTT CCC        277
Ser Lys Phe Leu Glu Gln Val His Gln Leu Tyr Asp Asp Ser Phe Pro
         15                  20                  25

ATG GAA ATC AGA CAG TAC CTG GCA CAG TGG TTA GAA AAG CAA GAC TGG        325
Met Glu Ile Arg Gln Tyr Leu Ala Gln Trp Leu Glu Lys Gln Asp Trp
             30                  35                  40

GAG CAC GCT GCC AAT GAT GTT TCA TTT GCC ACC ATC CGT TTT CAT GAC        373
Glu His Ala Ala Asn Asp Val Ser Phe Ala Thr Ile Arg Phe His Asp
 45                  50                  55

CTC CTG TCA CAG CTG GAT GAT CAA TAT AGT CGC TTT TCT TTG GAG AAT        421
Leu Leu Ser Gln Leu Asp Asp Gln Tyr Ser Arg Phe Ser Leu Glu Asn
 60                  65                  70                  75

AAC TTC TTG CTA CAG CAT AAC ATA AGG AAA AGC AAG CGT AAT CTT CAG        469
Asn Phe Leu Leu Gln His Asn Ile Arg Lys Ser Lys Arg Asn Leu Gln
                 80                  85                  90

GAT AAT TTT CAG GAA GAC CCA ATC CAG ATG TCT ATG ATC ATT TAC AGC        517
Asp Asn Phe Gln Glu Asp Pro Ile Gln Met Ser Met Ile Ile Tyr Ser
         95                 100                 105

TGT CTG AAG GAA GAA AGG AAA ATT CTG GAA AAC GCC CAG AGA TTT AAT        565
Cys Leu Lys Glu Glu Arg Lys Ile Leu Glu Asn Ala Gln Arg Phe Asn
            110                 115                 120

CAG GCT CAG TCG GGG AAT ATT CAG AGC ACA GTG ATG TTA GAC AAA CAG        613
Gln Ala Gln Ser Gly Asn Ile Gln Ser Thr Val Met Leu Asp Lys Gln
125                 130                 135

AAA GAG CTT GAC AGT AAA GTC AGA AAT GTG AAG GAC AAG GTT ATG TGT        661
Lys Glu Leu Asp Ser Lys Val Arg Asn Val Lys Asp Lys Val Met Cys
140                 145                 150                 155

ATA GAG CAT GAA ATC AAG AGC CTG GAA GAT TTA CAA GAT GAA TAT GAC        709
Ile Glu His Glu Ile Lys Ser Leu Glu Asp Leu Gln Asp Glu Tyr Asp
                160                 165                 170

TTC AAA TGC AAA ACC TTG CAG AAC AGA GAA CAC GAG ACC AAT GGT GTG        757
Phe Lys Cys Lys Thr Leu Gln Asn Arg Glu His Glu Thr Asn Gly Val
        175                 180                 185

GCA AAG AGT GAT CAG AAA CAA GAA CAG CTG TTA CTC AAG AAG ATG TAT        805
Ala Lys Ser Asp Gln Lys Gln Glu Gln Leu Leu Leu Lys Lys Met Tyr
    190                 195                 200

TTA ATG CTT GAC AAT AAG AGA AAG GAA GTA GTT CAC AAA ATA ATA GAG        853
Leu Met Leu Asp Asn Lys Arg Lys Glu Val Val His Lys Ile Ile Glu
```

```
                205                     210                     215
TTG CTG AAT GTC ACT GAA CTT ACC CAG AAT GCC CTG ATT AAT GAT GAA      901
Leu Leu Asn Val Thr Glu Leu Thr Gln Asn Ala Leu Ile Asn Asp Glu
220                 225                 230                 235

CTA GTG GAG TGG AAG CGG AGA CAG CAG AGC GCC TGT ATT GGG GGG CCG      949
Leu Val Glu Trp Lys Arg Arg Gln Gln Ser Ala Cys Ile Gly Gly Pro
                240                 245                 250

CCC AAT GCT TGC TTG GAT CAG CTG CAG AAC TGG TTC ACT ATA GTT GCG      997
Pro Asn Ala Cys Leu Asp Gln Leu Gln Asn Trp Phe Thr Ile Val Ala
            255                 260                 265

GAG AGT CTG CAG CAA GTT CGG CAG CAG CTT AAA AAG TTG GAG GAA TTG      1045
Glu Ser Leu Gln Gln Val Arg Gln Gln Leu Lys Lys Leu Glu Glu Leu
        270                 275                 280

GAA CAG AAA TAC ACC TAC GAA CAT GAC CCT ATC ACA AAA AAC AAA CAA      1093
Glu Gln Lys Tyr Thr Tyr Glu His Asp Pro Ile Thr Lys Asn Lys Gln
    285                 290                 295

GTG TTA TGG GAC CGC ACC TTC AGT CTT TTC CAG CAG CTC ATT CAG AGC      1141
Val Leu Trp Asp Arg Thr Phe Ser Leu Phe Gln Gln Leu Ile Gln Ser
300                 305                 310                 315

TCG TTT GTG GTG GAA AGA CAG CCC TGC ATG CCA ACG CAC CCT CAG AGG      1189
Ser Phe Val Val Glu Arg Gln Pro Cys Met Pro Thr His Pro Gln Arg
                320                 325                 330

CCG CTG GTC TTG AAG ACA GGG GTC CAG TTC ACT GTG AAG TTG AGA CTG      1237
Pro Leu Val Leu Lys Thr Gly Val Gln Phe Thr Val Lys Leu Arg Leu
            335                 340                 345

TTG GTG AAA TTG CAA GAG CTG AAT TAT AAT TTG AAA GTC AAA GTC TTA      1285
Leu Val Lys Leu Gln Glu Leu Asn Tyr Asn Leu Lys Val Lys Val Leu
        350                 355                 360

TTT GAT AAA GAT GTG AAT GAG AGA AAT ACA GTA AAA GGA TTT AGG AAG      1333
Phe Asp Lys Asp Val Asn Glu Arg Asn Thr Val Lys Gly Phe Arg Lys
    365                 370                 375

TTC AAC ATT TTG GGC ACG CAC ACA AAA GTG ATG AAC ATG GAG GAG TCC      1381
Phe Asn Ile Leu Gly Thr His Thr Lys Val Met Asn Met Glu Glu Ser
380                 385                 390                 395

ACC AAT GGC AGT CTG GCG GCT GAA TTT CGG CAC CTG CAA TTG AAA GAA      1429
Thr Asn Gly Ser Leu Ala Ala Glu Phe Arg His Leu Gln Leu Lys Glu
                400                 405                 410

CAG AAA AAT GCT GGC ACC AGA ACG AAT GAG GGT CCT CTC ATC GTT ACT      1477
Gln Lys Asn Ala Gly Thr Arg Thr Asn Glu Gly Pro Leu Ile Val Thr
            415                 420                 425

GAA GAG CTT CAC TCC CTT AGT TTT GAA ACC CAA TTG TGC CAG CCT GGT      1525
Glu Glu Leu His Ser Leu Ser Phe Glu Thr Gln Leu Cys Gln Pro Gly
        430                 435                 440

TTG GTA ATT GAC CTC GAG ACG ACC TCT CTG CCC GTT GTG GTG ATC TCC      1573
Leu Val Ile Asp Leu Glu Thr Thr Ser Leu Pro Val Val Val Ile Ser
    445                 450                 455

AAC GTC AGC CAG CTC CCG AGC GGT TGG GCC TCC ATC CTT TGG TAC AAC      1621
Asn Val Ser Gln Leu Pro Ser Gly Trp Ala Ser Ile Leu Trp Tyr Asn
460                 465                 470                 475

ATG CTG GTG GCG GAA CCC AGG AAT CTG TCC TTC TTC CTG ACT CCA CCA      1669
Met Leu Val Ala Glu Pro Arg Asn Leu Ser Phe Phe Leu Thr Pro Pro
                480                 485                 490

TGT GCA CGA TGG GCT CAG CTT TCA GAA GTG CTG AGT TGG CAG TTT TCT      1717
Cys Ala Arg Trp Ala Gln Leu Ser Glu Val Leu Ser Trp Gln Phe Ser
            495                 500                 505

TCT GTC ACC AAA AGA GGT CTC AAT GTG GAC CAG CTG AAC ATG TTG GGA      1765
Ser Val Thr Lys Arg Gly Leu Asn Val Asp Gln Leu Asn Met Leu Gly
        510                 515                 520

GAG AAG CTT CTT GGT CCT AAC GCC AGC CCC GAT GGT CTC ATT CCG TGG      1813
Glu Lys Leu Leu Gly Pro Asn Ala Ser Pro Asp Gly Leu Ile Pro Trp
```

```
                525                 530                 535
ACG AGG TTT TGT AAG GAA AAT ATA AAT GAT AAA AAT TTT CCC TTC TGG    1861
Thr Arg Phe Cys Lys Glu Asn Ile Asn Asp Lys Asn Phe Pro Phe Trp
540                 545                 550                 555

CTT TGG ATT GAA AGC ATC CTA GAA CTC ATT AAA AAA CAC CTG CTC CCT    1909
Leu Trp Ile Glu Ser Ile Leu Glu Leu Ile Lys Lys His Leu Leu Pro
                560                 565                 570

CTC TGG AAT GAT GGG TGC ATC ATG GGC TTC ATC AGC AAG GAG CGA GAG    1957
Leu Trp Asn Asp Gly Cys Ile Met Gly Phe Ile Ser Lys Glu Arg Glu
            575                 580                 585

CGT GCC CTG TTG AAG GAC CAG CAG CCG GGG ACC TTC CTG CTG CGG TTC    2005
Arg Ala Leu Leu Lys Asp Gln Gln Pro Gly Thr Phe Leu Leu Arg Phe
        590                 595                 600

AGT GAG AGC TCC CGG GAA GGG GCC ATC ACA TTC ACA TGG GTG GAG CGG    2053
Ser Glu Ser Ser Arg Glu Gly Ala Ile Thr Phe Thr Trp Val Glu Arg
    605                 610                 615

TCC CAG AAC GGA GGC GAA CCT GAC TTC CAT GCG GTT GAA CCC TAC ACG    2101
Ser Gln Asn Gly Gly Glu Pro Asp Phe His Ala Val Glu Pro Tyr Thr
620                 625                 630                 635

AAG AAA GAA CTT TCT GCT GTT ACT TTC CCT GAC ATC ATT CGC AAT TAC    2149
Lys Lys Glu Leu Ser Ala Val Thr Phe Pro Asp Ile Ile Arg Asn Tyr
                640                 645                 650

AAA GTC ATG GCT GCT GAG AAT ATT CCT GAG AAT CCC CTG AAG TAT CTG    2197
Lys Val Met Ala Ala Glu Asn Ile Pro Glu Asn Pro Leu Lys Tyr Leu
            655                 660                 665

TAT CCA AAT ATT GAC AAA GAC CAT GCC TTT GGA AAG TAT TAC TCC AGG    2245
Tyr Pro Asn Ile Asp Lys Asp His Ala Phe Gly Lys Tyr Tyr Ser Arg
        670                 675                 680

CCA AAG GAA GCA CCA GAG CCA ATG GAA CTT GAT GGC CCT AAA GGA ACT    2293
Pro Lys Glu Ala Pro Glu Pro Met Glu Leu Asp Gly Pro Lys Gly Thr
    685                 690                 695

GGA TAT ATC AAG ACT GAG TTG ATT TCT GTG TCT GAA GTG TAAGTGAACA     2342
Gly Tyr Ile Lys Thr Glu Leu Ile Ser Val Ser Glu Val
700                 705                 710

CAGAAGAGTG ACATGTTTAC AAACCTCAAG CCAGCCTTGC TCCTGGCTGG GGCCTGTTGA  2402

AGATGCTTGT ATTTTACTTT TCCATTGTAA TTGCTATCGC CATCACAGCT GAACTTGTTG  2462

AGATCCCCGT GTTACTGCCT ATCAGCATTT TACTACTTTA AAAAAAAAAA AAAAAGCCAA  2522

AAACCAAATT TGTATTTAAG GTATATAAAT TTTCCAAAA CTGATACCCT TGAAAAAGT    2582

ATAAATAAAA TGAGCAAAAG TTGAA                                        2607

(2) INFORMATION FOR SEQ ID NO:6:

(i) SEQUENCE CHARACTERISTICS:
        (A) LENGTH: 712 amino acids
        (B) TYPE: amino acid
        (D) TOPOLOGY: linear (ii) MOLECULE TYPE: protein (xi) SEQUENCE DESCRIPTION: SEQ ID NO:6:

Met Ser Gln Trp Tyr Glu Leu Gln Gln Leu Asp Ser Lys Phe Leu Glu
 1               5                  10                  15

Gln Val His Gln Leu Tyr Asp Asp Ser Phe Pro Met Glu Ile Arg Gln
            20                  25                  30

Tyr Leu Ala Gln Trp Leu Glu Lys Gln Asp Trp Glu His Ala Ala Asn
        35                  40                  45

Asp Val Ser Phe Ala Thr Ile Arg Phe His Asp Leu Leu Ser Gln Leu
    50                  55                  60
```

```
Asp Asp Gln Tyr Ser Arg Phe Ser Leu Glu Asn Asn Phe Leu Leu Gln
 65              70                  75                  80

His Asn Ile Arg Lys Ser Lys Arg Asn Leu Gln Asp Asn Phe Gln Glu
                 85                  90                  95

Asp Pro Ile Gln Met Ser Met Ile Ile Tyr Ser Cys Leu Lys Glu Glu
                100                 105                 110

Arg Lys Ile Leu Glu Asn Ala Gln Arg Phe Asn Gln Ala Gln Ser Gly
            115                 120                 125

Asn Ile Gln Ser Thr Val Met Leu Asp Lys Gln Lys Glu Leu Asp Ser
        130                 135                 140

Lys Val Arg Asn Val Lys Asp Lys Val Met Cys Ile Glu His Glu Ile
145                 150                 155                 160

Lys Ser Leu Glu Asp Leu Gln Asp Glu Tyr Asp Phe Lys Cys Lys Thr
                165                 170                 175

Leu Gln Asn Arg Glu His Glu Thr Asn Gly Val Ala Lys Ser Asp Gln
                180                 185                 190

Lys Gln Glu Gln Leu Leu Lys Lys Met Tyr Leu Met Leu Asp Asn
            195                 200                 205

Lys Arg Lys Glu Val Val His Lys Ile Ile Glu Leu Leu Asn Val Thr
        210                 215                 220

Glu Leu Thr Gln Asn Ala Leu Ile Asn Asp Glu Leu Val Glu Trp Lys
225                 230                 235                 240

Arg Arg Gln Gln Ser Ala Cys Ile Gly Gly Pro Pro Asn Ala Cys Leu
                245                 250                 255

Asp Gln Leu Gln Asn Trp Phe Thr Ile Val Ala Glu Ser Leu Gln Gln
                260                 265                 270

Val Arg Gln Gln Leu Lys Lys Leu Glu Glu Leu Glu Gln Lys Tyr Thr
            275                 280                 285

Tyr Glu His Asp Pro Ile Thr Lys Asn Lys Gln Val Leu Trp Asp Arg
        290                 295                 300

Thr Phe Ser Leu Phe Gln Gln Leu Ile Gln Ser Ser Phe Val Val Glu
305                 310                 315                 320

Arg Gln Pro Cys Met Pro Thr His Pro Gln Arg Pro Leu Val Leu Lys
                325                 330                 335

Thr Gly Val Gln Phe Thr Val Lys Leu Arg Leu Leu Val Lys Leu Gln
                340                 345                 350

Glu Leu Asn Tyr Asn Leu Lys Val Lys Val Leu Phe Asp Lys Asp Val
            355                 360                 365

Asn Glu Arg Asn Thr Val Lys Gly Phe Arg Lys Phe Asn Ile Leu Gly
        370                 375                 380

Thr His Thr Lys Val Met Asn Met Glu Glu Ser Thr Asn Gly Ser Leu
385                 390                 395                 400

Ala Ala Glu Phe Arg His Leu Gln Leu Lys Glu Gln Lys Asn Ala Gly
                405                 410                 415

Thr Arg Thr Asn Glu Gly Pro Leu Ile Val Thr Glu Glu Leu His Ser
                420                 425                 430

Leu Ser Phe Glu Thr Gln Leu Cys Gln Pro Gly Leu Val Ile Asp Leu
            435                 440                 445

Glu Thr Thr Ser Leu Pro Val Val Val Ile Ser Asn Val Ser Gln Leu
        450                 455                 460

Pro Ser Gly Trp Ala Ser Ile Leu Trp Tyr Asn Met Leu Val Ala Glu
465                 470                 475                 480

Pro Arg Asn Leu Ser Phe Phe Leu Thr Pro Cys Ala Arg Trp Ala
                485                 490                 495
```

```
Gln Leu Ser Glu Val Leu Ser Trp Gln Phe Ser Ser Val Thr Lys Arg
        500                 505                 510

Gly Leu Asn Val Asp Gln Leu Asn Met Leu Gly Glu Lys Leu Leu Gly
        515                 520                 525

Pro Asn Ala Ser Pro Asp Gly Leu Ile Pro Trp Thr Arg Phe Cys Lys
        530                 535                 540

Glu Asn Ile Asn Asp Lys Asn Phe Pro Phe Trp Leu Trp Ile Glu Ser
545                 550                 555                 560

Ile Leu Glu Leu Ile Lys Lys His Leu Leu Pro Leu Trp Asn Asp Gly
                565                 570                 575

Cys Ile Met Gly Phe Ile Ser Lys Glu Arg Glu Arg Ala Leu Leu Lys
        580                 585                 590

Asp Gln Gln Pro Gly Thr Phe Leu Leu Arg Phe Ser Glu Ser Ser Arg
        595                 600                 605

Glu Gly Ala Ile Thr Phe Thr Trp Val Glu Arg Ser Gln Asn Gly Gly
        610                 615                 620

Glu Pro Asp Phe His Ala Val Glu Pro Tyr Thr Lys Lys Glu Leu Ser
625                 630                 635                 640

Ala Val Thr Phe Pro Asp Ile Ile Arg Asn Tyr Lys Val Met Ala Ala
                645                 650                 655

Glu Asn Ile Pro Glu Asn Pro Leu Lys Tyr Leu Tyr Pro Asn Ile Asp
                660                 665                 670

Lys Asp His Ala Phe Gly Lys Tyr Tyr Ser Arg Pro Lys Glu Ala Pro
        675                 680                 685

Glu Pro Met Glu Leu Asp Gly Pro Lys Gly Thr Gly Tyr Ile Lys Thr
        690                 695                 700

Glu Leu Ile Ser Val Ser Glu Val
705                 710

(2) INFORMATION FOR SEQ ID NO:7:

(i) SEQUENCE CHARACTERISTICS:
        (A) LENGTH: 2277 base pairs
        (B) TYPE: nucleic acid
        (C) STRANDEDNESS: both
        (D) TOPOLOGY: unknown (ii) MOLECULE TYPE: cDNA (iii) HYPOTHETICAL: NO (iv) ANTI-SENSE: NO (vi) ORIGINAL SOURCE:
        (A) ORGANISM: Mouse (vii) IMMEDIATE SOURCE:
        (B) CLONE: Murine Stat91

(ix) FEATURE:
        (A) NAME/KEY: CDS
        (B) LOCATION: 5..2251

(xi) SEQUENCE DESCRIPTION: SEQ ID NO:7:

CAGG ATG TCA CAG TGG TTC GAG CTT CAG CAG CTG GAC TCC AAG TTC CTG        49
     Met Ser Gln Trp Phe Glu Leu Gln Gln Leu Asp Ser Lys Phe Leu
     1               5                   10                  15

GAG CAG GTC CAC CAG CTG TAC GAT GAC AGT TTC CCC ATG GAA ATC AGA        97
Glu Gln Val His Gln Leu Tyr Asp Asp Ser Phe Pro Met Glu Ile Arg
                20                  25                  30

CAG TAC CTG GCC CAG TGG CTG GAA AAG CAA GAC TGG GAG CAC GCT GCC       145
Gln Tyr Leu Ala Gln Trp Leu Glu Lys Gln Asp Trp Glu His Ala Ala
```

|  |  |  |  |  |  |  |  |  |  |  |  |  |  |  |  |
|---|---|---|---|---|---|---|---|---|---|---|---|---|---|---|---|
|  |  |  | 35 |  |  |  | 40 |  |  |  | 45 |  |  |  |  |

```
TAT GAT GTC TCG TTT GCG ACC ATC CGC TTC CAT GAC CTC CTC TCA CAG       193
Tyr Asp Val Ser Phe Ala Thr Ile Arg Phe His Asp Leu Leu Ser Gln
         50                  55                  60

CTG GAC GAC CAG TAC AGC CGC TTT TCT CTG GAG AAT AAT TTC TTG TTG       241
Leu Asp Asp Gln Tyr Ser Arg Phe Ser Leu Glu Asn Asn Phe Leu Leu
         65                  70                  75

CAG CAC AAC ATA CGG AAA AGC AAG CGT AAT CTC CAG GAT AAC TTC CAA       289
Gln His Asn Ile Arg Lys Ser Lys Arg Asn Leu Gln Asp Asn Phe Gln
 80                  85                  90                  95

GAA GAT CCC GTA CAG ATG TCC ATG ATC ATC TAC AAC TGT CTG AAG GAA       337
Glu Asp Pro Val Gln Met Ser Met Ile Ile Tyr Asn Cys Leu Lys Glu
                100                 105                 110

GAA AGG AAG ATT TTG GAA AAT GCC CAA AGA TTT AAT CAG GCC CAG GAG       385
Glu Arg Lys Ile Leu Glu Asn Ala Gln Arg Phe Asn Gln Ala Gln Glu
            115                 120                 125

GGA AAT ATT CAG AAC ACT GTG ATG TTA GAT AAA CAG AAG GAG CTG GAC       433
Gly Asn Ile Gln Asn Thr Val Met Leu Asp Lys Gln Lys Glu Leu Asp
        130                 135                 140

AGT AAA GTC AGA AAT GTG AAG GAT CAA GTC ATG TGC ATA GAG CAG GAA       481
Ser Lys Val Arg Asn Val Lys Asp Gln Val Met Cys Ile Glu Gln Glu
145                 150                 155

ATC AAG ACC CTA GAA GAA TTA CAA GAT GAA TAT GAC TTT AAA TGC AAA       529
Ile Lys Thr Leu Glu Glu Leu Gln Asp Glu Tyr Asp Phe Lys Cys Lys
160                 165                 170                 175

ACC TCT CAG AAC AGA GAA GGT GAA GCC AAT GGT GTG GCG AAG AGC GAC       577
Thr Ser Gln Asn Arg Glu Gly Glu Ala Asn Gly Val Ala Lys Ser Asp
                180                 185                 190

CAA AAA CAG GAA CAG CTG CTG CTC CAC AAG ATG TTT TTA ATG CTT GAC       625
Gln Lys Gln Glu Gln Leu Leu Leu His Lys Met Phe Leu Met Leu Asp
            195                 200                 205

AAT AAG AGA AAG GAG ATA ATT CAC AAA ATC AGA GAG TTG CTG AAT TCC       673
Asn Lys Arg Lys Glu Ile Ile His Lys Ile Arg Glu Leu Leu Asn Ser
        210                 215                 220

ATC GAG CTC ACT CAG AAC ACT CTG ATT AAT GAC GAG CTC GTG GAG TGG       721
Ile Glu Leu Thr Gln Asn Thr Leu Ile Asn Asp Glu Leu Val Glu Trp
    225                 230                 235

AAG CGA AGG CAG CAG AGC GCC TGC ATC GGG GGA CCG CCC AAC GCC TGC       769
Lys Arg Arg Gln Gln Ser Ala Cys Ile Gly Gly Pro Pro Asn Ala Cys
240                 245                 250                 255

CTG GAT CAG CTG CAA ACG TGG TTC ACC ATT GTT GCA GAG ACC CTG CAG       817
Leu Asp Gln Leu Gln Thr Trp Phe Thr Ile Val Ala Glu Thr Leu Gln
                260                 265                 270

CAG ATC CGT CAG CAG CTT AAA AAG CTG GAG GAG TTG GAA CAG AAA TTC       865
Gln Ile Arg Gln Gln Leu Lys Lys Leu Glu Glu Leu Glu Gln Lys Phe
            275                 280                 285

ACC TAT GAG CCC GAC CCT ATT ACA AAA AAC AAG CAG GTG TTG TCA GAT       913
Thr Tyr Glu Pro Asp Pro Ile Thr Lys Asn Lys Gln Val Leu Ser Asp
        290                 295                 300

CGA ACC TTC CTC CTC TTC CAG CAG CTC ATT CAG AGC TCC TTC GTG GTA       961
Arg Thr Phe Leu Leu Phe Gln Gln Leu Ile Gln Ser Ser Phe Val Val
    305                 310                 315

GAA CGA CAG CCG TGC ATG CCC ACT CAC CCG CAG AGG CCC TTG GTC TTG      1009
Glu Arg Gln Pro Cys Met Pro Thr His Pro Gln Arg Pro Leu Val Leu
320                 325                 330                 335

AAG ACT GGG GTA CAG TTC ACT GTC AAG TCG AGA CTG TTG GTG AAA TTG      1057
Lys Thr Gly Val Gln Phe Thr Val Lys Ser Arg Leu Leu Val Lys Leu
                340                 345                 350

CAA GAG TCG AAT CTA TTA ACG AAA GTG AAA TGT CAC TTT GAC AAA GAT      1105
Gln Glu Ser Asn Leu Leu Thr Lys Val Lys Cys His Phe Asp Lys Asp
```

-continued

```
                355                 360                 365
GTG AAC GAG AAA AAC ACA GTT AAA GGA TTT CGG AAG TTC AAC ATC TTG        1153
Val Asn Glu Lys Asn Thr Val Lys Gly Phe Arg Lys Phe Asn Ile Leu
            370                 375                 380

GGT ACG CAC ACA AAA GTG ATG AAC ATG GAA GAA TCC ACC AAC GGA AGT        1201
Gly Thr His Thr Lys Val Met Asn Met Glu Glu Ser Thr Asn Gly Ser
385                 390                 395

CTG GCA GCT GAG CTC CGA CAC CTG CAA CTG AAG GAA CAG AAA AAC GCT        1249
Leu Ala Ala Glu Leu Arg His Leu Gln Leu Lys Glu Gln Lys Asn Ala
400                 405                 410                 415

GGG AAC AGA ACT AAT GAG GGG CCT CTC ATT GTC ACC GAA GAA CTT CAC        1297
Gly Asn Arg Thr Asn Glu Gly Pro Leu Ile Val Thr Glu Glu Leu His
            420                 425                 430

TCT CTT AGC TTT GAA ACC CAG TTG TGC CAG CCA GGC TTG GTG ATT GAC        1345
Ser Leu Ser Phe Glu Thr Gln Leu Cys Gln Pro Gly Leu Val Ile Asp
            435                 440                 445

CTG GAG ACC ACC TCT CTT CCT GTC GTG GTG ATC TCC AAC GTC AGC CAG        1393
Leu Glu Thr Thr Ser Leu Pro Val Val Val Ile Ser Asn Val Ser Gln
            450                 455                 460

CTC CCC AGT GGC TGG GCG TCT ATC CTG TGG TAC AAC ATG CTG GTG ACA        1441
Leu Pro Ser Gly Trp Ala Ser Ile Leu Trp Tyr Asn Met Leu Val Thr
465                 470                 475

GAG CCC AGG AAT CTC TCC TTC TTC CTG AAC CCC CCG TGC GCG TGG TGG        1489
Glu Pro Arg Asn Leu Ser Phe Phe Leu Asn Pro Pro Cys Ala Trp Trp
480                 485                 490                 495

TCC CAG CTC TCA GAG GTG TTG AGT TGG CAG TTT TCA TCA GTC ACC AAG        1537
Ser Gln Leu Ser Glu Val Leu Ser Trp Gln Phe Ser Ser Val Thr Lys
            500                 505                 510

AGA GGT CTG AAC GCA GAC CAG CTG AGC ATG CTG GGA GAG AAG CTG CTG        1585
Arg Gly Leu Asn Ala Asp Gln Leu Ser Met Leu Gly Glu Lys Leu Leu
            515                 520                 525

GGC CCT AAT GCT GGC CCT GAT GGT CTT ATT CCA TGG ACA AGG TTT TGT        1633
Gly Pro Asn Ala Gly Pro Asp Gly Leu Ile Pro Trp Thr Arg Phe Cys
            530                 535                 540

AAG GAA AAT ATT AAT GAT AAA AAT TTC TCC TTC TGG CCT TGG ATT GAC        1681
Lys Glu Asn Ile Asn Asp Lys Asn Phe Ser Phe Trp Pro Trp Ile Asp
545                 550                 555

ACC ATC CTA GAG CTC ATT AAG AAC GAC CTG CTG TGC CTC TGG AAT GAT        1729
Thr Ile Leu Glu Leu Ile Lys Asn Asp Leu Leu Cys Leu Trp Asn Asp
560                 565                 570                 575

GGG TGC ATT ATG GGC TTC ATC AGC AAG GAG CGA GAA CGC GCT CTG CTC        1777
Gly Cys Ile Met Gly Phe Ile Ser Lys Glu Arg Glu Arg Ala Leu Leu
                580                 585                 590

AAG GAC CAG CAG CCA GGG ACG TTC CTG CTT AGA TTC AGT GAG AGC TCC        1825
Lys Asp Gln Gln Pro Gly Thr Phe Leu Leu Arg Phe Ser Glu Ser Ser
            595                 600                 605

CGG GAA GGG GCC ATC ACA TTC ACA TGG GTG GAA CGG TCC CAG AAC GGA        1873
Arg Glu Gly Ala Ile Thr Phe Thr Trp Val Glu Arg Ser Gln Asn Gly
            610                 615                 620

GGT GAA CCT GAC TTC CAT GCC GTG GAG CCC TAC ACG AAA AAA GAA CTT        1921
Gly Glu Pro Asp Phe His Ala Val Glu Pro Tyr Thr Lys Lys Glu Leu
625                 630                 635

TCA GCT GTT ACT TTC CCA GAT ATT ATT CGC AAC TAC AAA GTC ATG GCT        1969
Ser Ala Val Thr Phe Pro Asp Ile Ile Arg Asn Tyr Lys Val Met Ala
640                 645                 650                 655

GCC GAG AAC ATA CCA GAG AAT CCC CTG AAG TAT CTG TAC CCC AAT ATT        2017
Ala Glu Asn Ile Pro Glu Asn Pro Leu Lys Tyr Leu Tyr Pro Asn Ile
                660                 665                 670

GAC AAA GAC CAC GCC TTT GGG AAG TAT TAT TCC AGA CCA AAG GAA GCA        2065
Asp Lys Asp His Ala Phe Gly Lys Tyr Tyr Ser Arg Pro Lys Glu Ala
```

|  | 675 |  |  |  | 680 |  |  |  | 685 |  |  |  |  |
|---|---|---|---|---|---|---|---|---|---|---|---|---|---|
| CCA | GAA | CCG | ATG | GAG | CTT | GAC | GAC | CCT | AAG | CGA | ACT | GGA | TAC ATC AAG | 2113 |
| Pro | Glu | Pro | Met | Glu | Leu | Asp | Asp | Pro | Lys | Arg | Thr | Gly | Tyr Ile Lys |  |
|  | 690 |  |  |  | 695 |  |  |  | 700 |  |  |  |  |
| ACT | GAG | TTG | ATT | TCT | GTG | TCT | GAA | GTC | CAC | CCT | TCT | AGA | CTT CAG ACC | 2161 |
| Thr | Glu | Leu | Ile | Ser | Val | Ser | Glu | Val | His | Pro | Ser | Arg | Leu Gln Thr |  |
| 705 |  |  |  |  | 710 |  |  |  | 715 |  |  |  |  |
| ACA | GAC | AAC | CTG | CTT | CCC | ATG | TCT | CCA | GAG | GAG | TTT | GAT | GAG ATG TCC | 2209 |
| Thr | Asp | Asn | Leu | Leu | Pro | Met | Ser | Pro | Glu | Glu | Phe | Asp | Glu Met Ser |  |
| 720 |  |  |  | 725 |  |  |  | 730 |  |  |  |  | 735 |
| CGG | ATA | GTG | GGC | CCC | GAA | TTT | GAC | AGT | ATG | ATG | AGC | ACA | GTA | 2251 |
| Arg | Ile | Val | Gly | Pro | Glu | Phe | Asp | Ser | Met | Met | Ser | Thr | Val |  |
|  |  |  | 740 |  |  |  | 745 |  |  |  |  |  |  |

TAAACACGAA TTTCTCTCTG GCGACA  2277

(2) INFORMATION FOR SEQ ID NO:8:

(i) SEQUENCE CHARACTERISTICS:
        (A) LENGTH: 749 amino acids
        (B) TYPE: amino acid
        (D) TOPOLOGY: linear (ii) MOLECULE TYPE: protein (xi) SEQUENCE DESCRIPTION: SEQ ID NO:8:

```
Met Ser Gln Trp Phe Glu Leu Gln Gln Leu Asp Ser Lys Phe Leu Glu
 1               5                  10                  15

Gln Val His Gln Leu Tyr Asp Asp Ser Phe Pro Met Glu Ile Arg Gln
            20                  25                  30

Tyr Leu Ala Gln Trp Leu Glu Lys Gln Asp Trp Glu His Ala Ala Tyr
        35                  40                  45

Asp Val Ser Phe Ala Thr Ile Arg Phe His Asp Leu Leu Ser Gln Leu
    50                  55                  60

Asp Asp Gln Tyr Ser Arg Phe Ser Leu Glu Asn Asn Phe Leu Leu Gln
65                  70                  75                  80

His Asn Ile Arg Lys Ser Lys Arg Asn Leu Gln Asp Asn Phe Gln Glu
                85                  90                  95

Asp Pro Val Gln Met Ser Met Ile Ile Tyr Asn Cys Leu Lys Glu Glu
            100                 105                 110

Arg Lys Ile Leu Glu Asn Ala Gln Arg Phe Asn Gln Ala Gln Glu Gly
        115                 120                 125

Asn Ile Gln Asn Thr Val Met Leu Asp Lys Gln Lys Glu Leu Asp Ser
    130                 135                 140

Lys Val Arg Asn Val Lys Asp Gln Val Met Cys Ile Glu Gln Glu Ile
145                 150                 155                 160

Lys Thr Leu Glu Glu Leu Gln Asp Glu Tyr Asp Phe Lys Cys Lys Thr
                165                 170                 175

Ser Gln Asn Arg Glu Gly Glu Ala Asn Gly Val Ala Lys Ser Asp Gln
            180                 185                 190

Lys Gln Glu Gln Leu Leu Leu His Lys Met Phe Leu Met Leu Asp Asn
        195                 200                 205

Lys Arg Lys Glu Ile Ile His Lys Ile Arg Glu Leu Leu Asn Ser Ile
    210                 215                 220

Glu Leu Thr Gln Asn Thr Leu Ile Asn Asp Glu Leu Val Glu Trp Lys
225                 230                 235                 240

Arg Arg Gln Gln Ser Ala Cys Ile Gly Gly Pro Pro Asn Ala Cys Leu
                245                 250                 255
```

-continued

```
Asp Gln Leu Gln Thr Trp Phe Thr Ile Val Ala Glu Thr Leu Gln Gln
        260                 265                 270

Ile Arg Gln Gln Leu Lys Lys Leu Glu Glu Leu Glu Gln Lys Phe Thr
        275                 280                 285

Tyr Glu Pro Asp Pro Ile Thr Lys Asn Lys Gln Val Leu Ser Asp Arg
290                 295                 300

Thr Phe Leu Leu Phe Gln Gln Leu Ile Gln Ser Ser Phe Val Val Glu
305                 310                 315                 320

Arg Gln Pro Cys Met Pro Thr His Pro Gln Arg Pro Leu Val Leu Lys
                325                 330                 335

Thr Gly Val Gln Phe Thr Val Lys Ser Arg Leu Leu Val Lys Leu Gln
                340                 345                 350

Glu Ser Asn Leu Leu Thr Lys Val Lys Cys His Phe Asp Lys Asp Val
        355                 360                 365

Asn Glu Lys Asn Thr Val Lys Gly Phe Arg Lys Phe Asn Ile Leu Gly
        370                 375                 380

Thr His Thr Lys Val Met Asn Met Glu Glu Ser Thr Asn Gly Ser Leu
385                 390                 395                 400

Ala Ala Glu Leu Arg His Leu Gln Leu Lys Glu Gln Lys Asn Ala Gly
                405                 410                 415

Asn Arg Thr Asn Glu Gly Pro Leu Ile Val Thr Glu Glu Leu His Ser
                420                 425                 430

Leu Ser Phe Glu Thr Gln Leu Cys Gln Pro Gly Leu Val Ile Asp Leu
        435                 440                 445

Glu Thr Thr Ser Leu Pro Val Val Val Ile Ser Asn Val Ser Gln Leu
450                 455                 460

Pro Ser Gly Trp Ala Ser Ile Leu Trp Tyr Asn Met Leu Val Thr Glu
465                 470                 475                 480

Pro Arg Asn Leu Ser Phe Phe Leu Asn Pro Pro Cys Ala Trp Trp Ser
                485                 490                 495

Gln Leu Ser Glu Val Leu Ser Trp Gln Phe Ser Ser Val Thr Lys Arg
        500                 505                 510

Gly Leu Asn Ala Asp Gln Leu Ser Met Leu Gly Glu Lys Leu Leu Gly
        515                 520                 525

Pro Asn Ala Gly Pro Asp Gly Leu Ile Pro Trp Thr Arg Phe Cys Lys
530                 535                 540

Glu Asn Ile Asn Asp Lys Asn Phe Ser Phe Trp Pro Trp Ile Asp Thr
545                 550                 555                 560

Ile Leu Glu Leu Ile Lys Asn Asp Leu Leu Cys Leu Trp Asn Asp Gly
                565                 570                 575

Cys Ile Met Gly Phe Ile Ser Lys Glu Arg Glu Arg Ala Leu Leu Lys
                580                 585                 590

Asp Gln Gln Pro Gly Thr Phe Leu Leu Arg Phe Ser Glu Ser Ser Arg
        595                 600                 605

Glu Gly Ala Ile Thr Phe Thr Trp Val Glu Arg Ser Gln Asn Gly Gly
610                 615                 620

Glu Pro Asp Phe His Ala Val Glu Pro Tyr Thr Lys Lys Glu Leu Ser
625                 630                 635                 640

Ala Val Thr Phe Pro Asp Ile Ile Arg Asn Tyr Lys Val Met Ala Ala
                645                 650                 655

Glu Asn Ile Pro Glu Asn Pro Leu Lys Tyr Leu Tyr Pro Asn Ile Asp
                660                 665                 670

Lys Asp His Ala Phe Gly Lys Tyr Tyr Ser Arg Pro Lys Glu Ala Pro
        675                 680                 685
```

```
Glu Pro Met Glu Leu Asp Asp Pro Lys Arg Thr Gly Tyr Ile Lys Thr
    690             695                 700
Glu Leu Ile Ser Val Ser Glu Val His Pro Ser Arg Leu Gln Thr Thr
705             710                 715                 720
Asp Asn Leu Leu Pro Met Ser Pro Glu Glu Phe Asp Glu Met Ser Arg
            725                 730                 735
Ile Val Gly Pro Glu Phe Asp Ser Met Met Ser Thr Val
            740                 745
```

(2) INFORMATION FOR SEQ ID NO:9:

(i) SEQUENCE CHARACTERISTICS:
        (A) LENGTH: 2375 base pairs
        (B) TYPE: nucleic acid
        (C) STRANDEDNESS: both
        (D) TOPOLOGY: unknown (ii) MOLECULE TYPE: cDNA (iii) HYPOTHETICAL: NO (iv) ANTI-SENSE: NO (vi) ORIGINAL SOURCE:
        (A) ORGANISM: Mouse (vii) IMMEDIATE SOURCE:
        (A) LIBRARY: splenic/thymic
        (B) CLONE: Murine 13sf1

(ix) FEATURE:
        (A) NAME/KEY: CDS
        (B) LOCATION: 34..2277

(xi) SEQUENCE DESCRIPTION: SEQ ID NO:9:

```
TGCCACTACC TGGACGGAGA GAGAGAGAGC AGC ATG TCT CAG TGG AAT CAA GTC        54
                                    Met Ser Gln Trp Asn Gln Val
                                      1               5

CAA CAA TTA GAA ATC AAG TTT TTG GAG CAA GTA GAT CAG TTC TAT GAT        102
Gln Gln Leu Glu Ile Lys Phe Leu Glu Gln Val Asp Gln Phe Tyr Asp
        10                  15                  20

GAC AAC TTT CCT ATG GAA ATC CGG CAT CTG CTA GCT CAG TGG ATT GAG        150
Asp Asn Phe Pro Met Glu Ile Arg His Leu Leu Ala Gln Trp Ile Glu
    25                  30                  35

ACT CAA GAC TGG GAA GTA GCT TCT AAC AAT GAA ACT ATG GCA ACA ATT        198
Thr Gln Asp Trp Glu Val Ala Ser Asn Asn Glu Thr Met Ala Thr Ile
40                  45                  50                  55

CTG CTT CAA AAC TTA CTA ATA CAA TTG GAT GAA CAG TTG GGG CGG GTT        246
Leu Leu Gln Asn Leu Leu Ile Gln Leu Asp Glu Gln Leu Gly Arg Val
                60                  65                  70

TCC AAA GAA AAA AAT CTG CTA TTG ATT CAC AAT CTA AAG AGA ATT AGA        294
Ser Lys Glu Lys Asn Leu Leu Leu Ile His Asn Leu Lys Arg Ile Arg
            75                  80                  85

AAA GTT CTT CAG GGC AAG TTT CAT GGA AAT CCA ATG CAT GTA GCT GTG        342
Lys Val Leu Gln Gly Lys Phe His Gly Asn Pro Met His Val Ala Val
        90                  95                 100

GTA ATT TCA AAT TGC TTA AGG GAA GAG AGG AGA ATA TTG GCT GCA GCC        390
Val Ile Ser Asn Cys Leu Arg Glu Glu Arg Arg Ile Leu Ala Ala Ala
    105                 110                 115

AAC ATG CCT ATC CAG GGA CCT CTG GAG AAA TCC TTA CAG AGT TCT TCA        438
Asn Met Pro Ile Gln Gly Pro Leu Glu Lys Ser Leu Gln Ser Ser Ser
120                 125                 130                 135

GTT TCT GAA AGA CAA AGG AAT GTG GAA CAC AAA GTG TCT GCC ATT AAA        486
Val Ser Glu Arg Gln Arg Asn Val Glu His Lys Val Ser Ala Ile Lys
                140                 145                 150
```

```
AAC AGT GTG CAG ATG ACA GAA CAA GAT ACC AAA TAC TTA GAA GAC CTG      534
Asn Ser Val Gln Met Thr Glu Gln Asp Thr Lys Tyr Leu Glu Asp Leu
            155                 160                 165

CAA GAT GAG TTT GAC TAC AGG TAT AAA ACA ATT CAG ACA ATG GAT CAG      582
Gln Asp Glu Phe Asp Tyr Arg Tyr Lys Thr Ile Gln Thr Met Asp Gln
        170                 175                 180

GGT GAC AAA AAC AGT ATC CTG GTG AAC CAG GAA GTT TTG ACA CTG CTG      630
Gly Asp Lys Asn Ser Ile Leu Val Asn Gln Glu Val Leu Thr Leu Leu
    185                 190                 195

CAA GAA ATG CTT AAT AGT CTG GAC TTC AAG AGA AAG GAA GCA CTC AGT      678
Gln Glu Met Leu Asn Ser Leu Asp Phe Lys Arg Lys Glu Ala Leu Ser
200                 205                 210                 215

AAG ATG ACG CAG ATA GTG AAC GAG ACA GAC CTG CTC ATG AAC AGC ATG      726
Lys Met Thr Gln Ile Val Asn Glu Thr Asp Leu Leu Met Asn Ser Met
                220                 225                 230

CTT CTA GAA GAG CTG CAG GAC TGG AAA AAG CGG CAC AGG ATT GCC TGC      774
Leu Leu Glu Glu Leu Gln Asp Trp Lys Lys Arg His Arg Ile Ala Cys
            235                 240                 245

ATT GGT GGC CCG CTC CAC AAT GGG CTG GAC CAG CTT CAG AAC TGC TTT      822
Ile Gly Gly Pro Leu His Asn Gly Leu Asp Gln Leu Gln Asn Cys Phe
        250                 255                 260

ACC CTA CTG GCA GAG AGT CTT TTC CAA CTC AGA CAG CAA CTG GAG AAA      870
Thr Leu Leu Ala Glu Ser Leu Phe Gln Leu Arg Gln Gln Leu Glu Lys
    265                 270                 275

CTA CAG GAG CAA TCT ACT AAA ATG ACC TAT GAA GGG GAT CCC ATC CCT      918
Leu Gln Glu Gln Ser Thr Lys Met Thr Tyr Glu Gly Asp Pro Ile Pro
280                 285                 290                 295

GCT CAA AGA GCA CAC CTC CTG GAA AGA GCT ACC TTC CTG ATC TAC AAC      966
Ala Gln Arg Ala His Leu Leu Glu Arg Ala Thr Phe Leu Ile Tyr Asn
                300                 305                 310

CTT TTC AAG AAC TCA TTT GTG GTC GAG CGA CAC GCA TGC ATG CCA ACG     1014
Leu Phe Lys Asn Ser Phe Val Val Glu Arg His Ala Cys Met Pro Thr
            315                 320                 325

CAC CCT CAG AGG CCG ATG GTA CTT AAA ACC CTC ATT CAG TTC ACT GTA     1062
His Pro Gln Arg Pro Met Val Leu Lys Thr Leu Ile Gln Phe Thr Val
        330                 335                 340

AAA CTG AGA TTA CTA ATA AAA TTG CCG GAA CTA AAC TAT CAG GTG AAA     1110
Lys Leu Arg Leu Leu Ile Lys Leu Pro Glu Leu Asn Tyr Gln Val Lys
    345                 350                 355

GTA AAG GCG TCC ATT GAC AAG AAT GTT TCA ACT CTA AGC AAT AGA AGA     1158
Val Lys Ala Ser Ile Asp Lys Asn Val Ser Thr Leu Ser Asn Arg Arg
360                 365                 370                 375

TTT GTG CTT TGT GGA ACT CAC GTC AAA GCT ATG TCC AGT GAG GAA TCT     1206
Phe Val Leu Cys Gly Thr His Val Lys Ala Met Ser Ser Glu Glu Ser
                380                 385                 390

TCC AAT GGG AGC CTC TCA GTG GAG TTA GAC ATT GCA ACC CAA GGA GAT     1254
Ser Asn Gly Ser Leu Ser Val Glu Leu Asp Ile Ala Thr Gln Gly Asp
            395                 400                 405

GAA GTG CAG TAC TGG AGT AAA GGA AAC GAG GGC TGC CAC ATG GTG ACA     1302
Glu Val Gln Tyr Trp Ser Lys Gly Asn Glu Gly Cys His Met Val Thr
        410                 415                 420

GAG GAG TTG CAT TCC ATA ACC TTT GAG ACC CAG ATC TGC CTC TAT GGC     1350
Glu Glu Leu His Ser Ile Thr Phe Glu Thr Gln Ile Cys Leu Tyr Gly
    425                 430                 435

CTC ACC ATT AAC CTA GAG ACC AGC TCA TTA CCT GTC GTG ATG ATT TCT     1398
Leu Thr Ile Asn Leu Glu Thr Ser Ser Leu Pro Val Val Met Ile Ser
440                 445                 450                 455

AAT GTC AGC CAA CTA CCT AAT GCA TGG GCA TCC ATC ATT TGG TAC AAT     1446
Asn Val Ser Gln Leu Pro Asn Ala Trp Ala Ser Ile Ile Trp Tyr Asn
                460                 465                 470
```

```
GTA TCA ACT AAC GAC TCC CAG AAC TTG GTT TTC TTT AAT AAC CCT CCA         1494
Val Ser Thr Asn Asp Ser Gln Asn Leu Val Phe Phe Asn Asn Pro Pro
            475                 480                 485

TCT GTC ACT TTG GGC CAA CTC CTG GAA GTG ATG AGC TGG CAA TTT TCA         1542
Ser Val Thr Leu Gly Gln Leu Leu Glu Val Met Ser Trp Gln Phe Ser
            490                 495                 500

TCC TAT GTC GGT CGT GGC CTT AAT TCA GAG CAG CTC AAC ATG CTG GCA         1590
Ser Tyr Val Gly Arg Gly Leu Asn Ser Glu Gln Leu Asn Met Leu Ala
            505                 510                 515

GAG AAG CTC ACA GTT CAG TCT AAC TAC AAT GAT GGT CAC CTC ACC TGG         1638
Glu Lys Leu Thr Val Gln Ser Asn Tyr Asn Asp Gly His Leu Thr Trp
520                 525                 530                 535

GCC AAG TTC TGC AAG GAA CAT TTG CCT GGC AAA ACA TTT ACC TTC TGG         1686
Ala Lys Phe Cys Lys Glu His Leu Pro Gly Lys Thr Phe Thr Phe Trp
            540                 545                 550

ACT TGG CTT GAA GCA ATA TTG GAC CTA ATT AAA AAA CAT ATT CTT CCC         1734
Thr Trp Leu Glu Ala Ile Leu Asp Leu Ile Lys Lys His Ile Leu Pro
            555                 560                 565

CTC TGG ATT GAT GGG TAC ATC ATG GGA TTT GTT AGT AAA GAG AAG GAA         1782
Leu Trp Ile Asp Gly Tyr Ile Met Gly Phe Val Ser Lys Glu Lys Glu
            570                 575                 580

CGG CTT CTG CTC AAA GAT AAA ATG CCT GGG ACA TTT TTG TTA AGA TTC         1830
Arg Leu Leu Leu Lys Asp Lys Met Pro Gly Thr Phe Leu Leu Arg Phe
585                 590                 595

AGT GAG AGC CAT CTT GGA GGG ATA ACC TTC ACC TGG GTG GAC CAA TCT         1878
Ser Glu Ser His Leu Gly Gly Ile Thr Phe Thr Trp Val Asp Gln Ser
600                 605                 610                 615

GAA AAT GGA GAA GTG AGA TTC CAC TCT GTA GAA CCC TAC AAC AAA GGG         1926
Glu Asn Gly Glu Val Arg Phe His Ser Val Glu Pro Tyr Asn Lys Gly
            620                 625                 630

AGA CTG TCG GCT CTG GCC TTC GCT GAC ATC CTG CGA GAC TAC AAG GTT         1974
Arg Leu Ser Ala Leu Ala Phe Ala Asp Ile Leu Arg Asp Tyr Lys Val
            635                 640                 645

ATC ATG GCT GAA AAC ATC CCT GAA AAC CCT CTG AAG TAC CTC TAC CCT         2022
Ile Met Ala Glu Asn Ile Pro Glu Asn Pro Leu Lys Tyr Leu Tyr Pro
            650                 655                 660

GAC ATT CCC AAA GAC AAA GCC TTT GGC AAA CAC TAC AGC TCC CAG CCG         2070
Asp Ile Pro Lys Asp Lys Ala Phe Gly Lys His Tyr Ser Ser Gln Pro
            665                 670                 675

TGC GAA GTC TCA AGA CCA ACC GAA CGG GGA GAC AAG GGT TAC GTC CCC         2118
Cys Glu Val Ser Arg Pro Thr Glu Arg Gly Asp Lys Gly Tyr Val Pro
680                 685                 690                 695

TCT GTT TTT ATC CCC ATT TCA ACA ATC CGA AGC GAT TCC ACG GAG CCA         2166
Ser Val Phe Ile Pro Ile Ser Thr Ile Arg Ser Asp Ser Thr Glu Pro
                700                 705                 710

CAA TCT CCT TCA GAC CTT CTC CCC ATG TCT CCA AGT GCA TAT GCT GTG         2214
Gln Ser Pro Ser Asp Leu Leu Pro Met Ser Pro Ser Ala Tyr Ala Val
            715                 720                 725

CTG AGA GAA AAC CTG AGC CCA ACG ACA ATT GAA ACT GCA ATG AAT TCC         2262
Leu Arg Glu Asn Leu Ser Pro Thr Thr Ile Glu Thr Ala Met Asn Ser
            730                 735                 740

CCA TAT TCT GCT GAA TGACGGTGCA AACGGACACT TTAAAGAAGG AAGCAGATGA         2317
Pro Tyr Ser Ala Glu
        745

AACTGGAGAG TGTTCTTTAC CATAGATCAC AATTTATTTC TTCGGCTTTG TAAATACC        2375
```

(2) INFORMATION FOR SEQ ID NO:10:

(i) SEQUENCE CHARACTERISTICS:
        (A) LENGTH: 748 amino acids (B) TYPE: amino acid
(D) TOPOLOGY: linear (ii) MOLECULE TYPE: protein (xi) SEQUENCE DESCRIPTION: SEQ ID NO:10:

```
Met Ser Gln Trp Asn Gln Val Gln Gln Leu Glu Ile Lys Phe Leu Glu
 1               5                  10                  15

Gln Val Asp Gln Phe Tyr Asp Asp Asn Phe Pro Met Glu Ile Arg His
            20                  25                  30

Leu Leu Ala Gln Trp Ile Glu Thr Gln Asp Trp Glu Val Ala Ser Asn
        35                  40                  45

Asn Glu Thr Met Ala Thr Ile Leu Leu Gln Asn Leu Leu Ile Gln Leu
    50                  55                  60

Asp Glu Gln Leu Gly Arg Val Ser Lys Glu Lys Asn Leu Leu Leu Ile
65                  70                  75                  80

His Asn Leu Lys Arg Ile Arg Lys Val Leu Gln Gly Lys Phe His Gly
                85                  90                  95

Asn Pro Met His Val Ala Val Val Ile Ser Asn Cys Leu Arg Glu Glu
            100                 105                 110

Arg Arg Ile Leu Ala Ala Ala Asn Met Pro Ile Gln Gly Pro Leu Glu
        115                 120                 125

Lys Ser Leu Gln Ser Ser Val Ser Glu Arg Gln Arg Asn Val Glu
    130                 135                 140

His Lys Val Ser Ala Ile Lys Asn Ser Val Gln Met Thr Glu Gln Asp
145                 150                 155                 160

Thr Lys Tyr Leu Glu Asp Leu Gln Asp Glu Phe Asp Tyr Arg Tyr Lys
                165                 170                 175

Thr Ile Gln Thr Met Asp Gln Gly Asp Lys Asn Ser Ile Leu Val Asn
            180                 185                 190

Gln Glu Val Leu Thr Leu Leu Gln Glu Met Leu Asn Ser Leu Asp Phe
        195                 200                 205

Lys Arg Lys Glu Ala Leu Ser Lys Met Thr Gln Ile Val Asn Glu Thr
    210                 215                 220

Asp Leu Leu Met Asn Ser Met Leu Leu Glu Glu Leu Gln Asp Trp Lys
225                 230                 235                 240

Lys Arg His Arg Ile Ala Cys Ile Gly Gly Pro Leu His Asn Gly Leu
                245                 250                 255

Asp Gln Leu Gln Asn Cys Phe Thr Leu Leu Ala Glu Ser Leu Phe Gln
            260                 265                 270

Leu Arg Gln Gln Leu Glu Lys Leu Gln Glu Gln Ser Thr Lys Met Thr
        275                 280                 285

Tyr Glu Gly Asp Pro Ile Pro Ala Gln Arg Ala His Leu Leu Glu Arg
    290                 295                 300

Ala Thr Phe Leu Ile Tyr Asn Leu Phe Lys Asn Ser Phe Val Val Glu
305                 310                 315                 320

Arg His Ala Cys Met Pro Thr His Pro Gln Arg Pro Met Val Leu Lys
                325                 330                 335

Thr Leu Ile Gln Phe Thr Val Lys Leu Arg Leu Leu Ile Lys Leu Pro
            340                 345                 350

Glu Leu Asn Tyr Gln Val Lys Val Lys Ala Ser Ile Asp Lys Asn Val
        355                 360                 365

Ser Thr Leu Ser Asn Arg Arg Phe Val Leu Cys Gly Thr His Val Lys
    370                 375                 380

Ala Met Ser Ser Glu Glu Ser Ser Asn Gly Ser Leu Ser Val Glu Leu
```

```
385                 390                 395                 400

Asp Ile Ala Thr Gln Gly Asp Glu Val Gln Tyr Trp Ser Lys Gly Asn
                405                 410                 415

Glu Gly Cys His Met Val Thr Glu Glu Leu His Ser Ile Thr Phe Glu
                420                 425                 430

Thr Gln Ile Cys Leu Tyr Gly Leu Thr Ile Asn Leu Glu Thr Ser Ser
                435                 440                 445

Leu Pro Val Val Met Ile Ser Asn Val Ser Gln Leu Pro Asn Ala Trp
            450                 455                 460

Ala Ser Ile Ile Trp Tyr Asn Val Ser Thr Asn Asp Ser Gln Asn Leu
465                 470                 475                 480

Val Phe Phe Asn Asn Pro Pro Ser Val Thr Leu Gly Gln Leu Leu Glu
                485                 490                 495

Val Met Ser Trp Gln Phe Ser Ser Tyr Val Gly Arg Gly Leu Asn Ser
                500                 505                 510

Glu Gln Leu Asn Met Leu Ala Glu Lys Leu Thr Val Gln Ser Asn Tyr
                515                 520                 525

Asn Asp Gly His Leu Thr Trp Ala Lys Phe Cys Lys Glu His Leu Pro
            530                 535                 540

Gly Lys Thr Phe Thr Phe Trp Thr Trp Leu Glu Ala Ile Leu Asp Leu
545                 550                 555                 560

Ile Lys Lys His Ile Leu Pro Leu Trp Ile Asp Gly Tyr Ile Met Gly
                565                 570                 575

Phe Val Ser Lys Glu Lys Glu Arg Leu Leu Lys Asp Lys Met Pro
                580                 585                 590

Gly Thr Phe Leu Leu Arg Phe Ser Glu Ser His Leu Gly Gly Ile Thr
                595                 600                 605

Phe Thr Trp Val Asp Gln Ser Glu Asn Gly Glu Val Arg Phe His Ser
            610                 615                 620

Val Glu Pro Tyr Asn Lys Gly Arg Leu Ser Ala Leu Ala Phe Ala Asp
625                 630                 635                 640

Ile Leu Arg Asp Tyr Lys Val Ile Met Ala Glu Asn Ile Pro Glu Asn
                645                 650                 655

Pro Leu Lys Tyr Leu Tyr Pro Asp Ile Pro Lys Asp Lys Ala Phe Gly
                660                 665                 670

Lys His Tyr Ser Ser Gln Pro Cys Glu Val Ser Arg Pro Thr Glu Arg
                675                 680                 685

Gly Asp Lys Gly Tyr Val Pro Ser Val Phe Ile Pro Ile Ser Thr Ile
            690                 695                 700

Arg Ser Asp Ser Thr Glu Pro Gln Ser Pro Ser Asp Leu Leu Pro Met
705                 710                 715                 720

Ser Pro Ser Ala Tyr Ala Val Leu Arg Glu Asn Leu Ser Pro Thr Thr
                725                 730                 735

Ile Glu Thr Ala Met Asn Ser Pro Tyr Ser Ala Glu
                740                 745

(2) INFORMATION FOR SEQ ID NO:11:

(i) SEQUENCE CHARACTERISTICS:
        (A) LENGTH: 2869 base pairs
        (B) TYPE: nucleic acid
        (C) STRANDEDNESS: both
        (D) TOPOLOGY: unknown (ii) MOLECULE TYPE: cDNA (iii) HYPOTHETICAL: NO
```

(iv) ANTI-SENSE: NO (vi) ORIGINAL SOURCE:
             (A) ORGANISM: Mouse (vii) IMMEDIATE SOURCE:
             (A) LIBRARY: splenic/thymic
             (B) CLONE: Murine 19sf6

(ix) FEATURE:
             (A) NAME/KEY: CDS
             (B) LOCATION: 69..2378

(xi) SEQUENCE DESCRIPTION: SEQ ID NO:11:

```
GCCGCGACCA GCCAGGCCGG CCAGTCGGGC TCAGCCCGGA GACAGTCGAG ACCCCTGACT        60

GCAGCAGG ATG GCT CAG TGG AAC CAG CTG CAG CAG CTG GAC ACA CGC TAC       110
         Met Ala Gln Trp Asn Gln Leu Gln Gln Leu Asp Thr Arg Tyr
           1               5                  10

CTG AAG CAG CTG CAC CAG CTG TAC AGC GAC ACG TTC CCC ATG GAG CTG        158
Leu Lys Gln Leu His Gln Leu Tyr Ser Asp Thr Phe Pro Met Glu Leu
 15              20                  25                  30

CGG CAG TTC CTG GCA CCT TGG ATT GAG AGT CAA GAC TGG GCA TAT GCA        206
Arg Gln Phe Leu Ala Pro Trp Ile Glu Ser Gln Asp Trp Ala Tyr Ala
                 35                  40                  45

GCC AGC AAA GAG TCA CAT GCC ACG TTG GTG TTT CAT AAT CTC TTG GGT        254
Ala Ser Lys Glu Ser His Ala Thr Leu Val Phe His Asn Leu Leu Gly
             50                  55                  60

GAA ATT GAC CAG CAA TAT AGC CGA TTC CTG CAA GAG TCC AAT GTC CTC        302
Glu Ile Asp Gln Gln Tyr Ser Arg Phe Leu Gln Glu Ser Asn Val Leu
         65                  70                  75

TAT CAG CAC AAC CTT CGA AGA ATC AAG CAG TTT CTG CAG AGC AGG TAT        350
Tyr Gln His Asn Leu Arg Arg Ile Lys Gln Phe Leu Gln Ser Arg Tyr
     80                  85                  90

CTT GAG AAG CCA ATG GAA ATT GCC CGG ATC GTG GCC CGA TGC CTG TGG        398
Leu Glu Lys Pro Met Glu Ile Ala Arg Ile Val Ala Arg Cys Leu Trp
 95                 100                 105                 110

GAA GAG TCT CGC CTC CTC CAG ACG GCA GCC ACG GCA GCC CAG CAA GGG        446
Glu Glu Ser Arg Leu Leu Gln Thr Ala Ala Thr Ala Ala Gln Gln Gly
                115                 120                 125

GGC CAG GCC AAC CAC CCA ACA GCC GCC GTA GTG ACA GAG AAG CAG CAG        494
Gly Gln Ala Asn His Pro Thr Ala Ala Val Val Thr Glu Lys Gln Gln
            130                 135                 140

ATG TTG GAG CAG CAT CTT CAG GAT GTC CGG AAG CGA GTG CAG GAT CTA        542
Met Leu Glu Gln His Leu Gln Asp Val Arg Lys Arg Val Gln Asp Leu
        145                 150                 155

GAA CAG AAA ATG AAG GTG GTG GAG AAC CTC CAG GAC GAC TTT GAT TTC        590
Glu Gln Lys Met Lys Val Val Glu Asn Leu Gln Asp Asp Phe Asp Phe
    160                 165                 170

AAC TAC AAA ACC CTC AAG AGC CAA GGA GAC ATG CAG GAT CTG AAT GGA        638
Asn Tyr Lys Thr Leu Lys Ser Gln Gly Asp Met Gln Asp Leu Asn Gly
175                 180                 185                 190

AAC AAC CAG TCT GTG ACC AGA CAG AAG ATG CAG CAG CTG GAA CAG ATG        686
Asn Asn Gln Ser Val Thr Arg Gln Lys Met Gln Gln Leu Glu Gln Met
                195                 200                 205

CTC ACA GCC CTG GAC CAG ATG CGG AGA AGC ATT GTG AGT GAG CTG GCG        734
Leu Thr Ala Leu Asp Gln Met Arg Arg Ser Ile Val Ser Glu Leu Ala
            210                 215                 220

GGG CTC TTG TCA GCA ATG GAG TAC GTG CAG AAG ACA CTG ACT GAT GAA        782
Gly Leu Leu Ser Ala Met Glu Tyr Val Gln Lys Thr Leu Thr Asp Glu
        225                 230                 235

GAG CTG GCT GAC TGG AAG AGG CGG CCA GAG ATC GCG TGC ATC GGA GGC        830
Glu Leu Ala Asp Trp Lys Arg Arg Pro Glu Ile Ala Cys Ile Gly Gly
```

```
              240                 245                 250
CCT CCC AAC ATC TGC CTG GAC CGT CTG GAA AAC TGG ATA ACT TCA TTA      878
Pro Pro Asn Ile Cys Leu Asp Arg Leu Glu Asn Trp Ile Thr Ser Leu
255                 260                 265                 270

GCA GAA TCT CAA CTT CAG ACC CGC CAA CAA ATT AAG AAA CTG GAG GAG      926
Ala Glu Ser Gln Leu Gln Thr Arg Gln Gln Ile Lys Lys Leu Glu Glu
                275                 280                 285

CTG CAG CAG AAA GTG TCC TAC AAG GGC GAC CCT ATC GTG CAG CAC CGG      974
Leu Gln Gln Lys Val Ser Tyr Lys Gly Asp Pro Ile Val Gln His Arg
            290                 295                 300

CCC ATG CTG GAG GAG AGG ATC GTG GAG CTG TTC AGA AAC TTA ATG AAG     1022
Pro Met Leu Glu Glu Arg Ile Val Glu Leu Phe Arg Asn Leu Met Lys
        305                 310                 315

AGT GCC TTC GTG GTG GAG CGG CAG CCC TGC ATG CCC ATG CAC CCG GAC     1070
Ser Ala Phe Val Val Glu Arg Gln Pro Cys Met Pro Met His Pro Asp
    320                 325                 330

CGG CCC TTA GTC ATC AAG ACT GGT GTC CAG TTT ACC ACG AAA GTC AGG     1118
Arg Pro Leu Val Ile Lys Thr Gly Val Gln Phe Thr Thr Lys Val Arg
335                 340                 345                 350

TTG CTG GTC AAA TTT CCT GAG TTG AAT TAT CAG CTT AAA ATT AAA GTG     1166
Leu Leu Val Lys Phe Pro Glu Leu Asn Tyr Gln Leu Lys Ile Lys Val
                355                 360                 365

TGC ATT GAT AAA GAC TCT GGG GAT GTT GCT GCC CTC AGA GGG TCT CGG     1214
Cys Ile Asp Lys Asp Ser Gly Asp Val Ala Ala Leu Arg Gly Ser Arg
            370                 375                 380

AAA TTT AAC ATT CTG GGC ACG AAC ACA AAA GTG ATG AAC ATG GAG GAG     1262
Lys Phe Asn Ile Leu Gly Thr Asn Thr Lys Val Met Asn Met Glu Glu
        385                 390                 395

TCT AAC AAC GGC AGC CTG TCT GCA GAG TTC AAG CAC CTG ACC CTT AGG     1310
Ser Asn Asn Gly Ser Leu Ser Ala Glu Phe Lys His Leu Thr Leu Arg
    400                 405                 410

GAG CAG AGA TGT GGG AAT GGA GGC CGT GCC AAT TGT GAT GCC TCC TTG     1358
Glu Gln Arg Cys Gly Asn Gly Gly Arg Ala Asn Cys Asp Ala Ser Leu
415                 420                 425                 430

ATC GTG ACT GAG GAG CTG CAC CTG ATC ACC TTC GAG ACT GAG GTG TAC     1406
Ile Val Thr Glu Glu Leu His Leu Ile Thr Phe Glu Thr Glu Val Tyr
                435                 440                 445

CAC CAA GGC CTC AAG ATT GAC CTA GAG ACC CAC TCC TTG CCA GTT GTG     1454
His Gln Gly Leu Lys Ile Asp Leu Glu Thr His Ser Leu Pro Val Val
            450                 455                 460

GTG ATC TCC AAC ATC TGT CAG ATG CCA AAT GCT TGG GCA TCA ATC CTG     1502
Val Ile Ser Asn Ile Cys Gln Met Pro Asn Ala Trp Ala Ser Ile Leu
        465                 470                 475

TGG TAT AAC ATG CTG ACC AAT AAC CCC AAG AAC GTG AAC TTC TTC ACT     1550
Trp Tyr Asn Met Leu Thr Asn Asn Pro Lys Asn Val Asn Phe Phe Thr
    480                 485                 490

AAG CCG CCA ATT GGA ACC TGG GAC CAA GTG GCC GAG GTG CTC AGC TGG     1598
Lys Pro Pro Ile Gly Thr Trp Asp Gln Val Ala Glu Val Leu Ser Trp
495                 500                 505                 510

CAG TTC TCG TCC ACC ACC AAG CGA GGG CTG AGC ATC GAG CAG CTG ACA     1646
Gln Phe Ser Ser Thr Thr Lys Arg Gly Leu Ser Ile Glu Gln Leu Thr
                515                 520                 525

ACG CTG GCT GAG AAG CTC CTA GGG CCT GGT GTG AAC TAC TCA GGG TGT     1694
Thr Leu Ala Glu Lys Leu Leu Gly Pro Gly Val Asn Tyr Ser Gly Cys
            530                 535                 540

CAG ATC ACA TGG GCT AAA TTC TGC AAA GAA AAC ATG GCT GGC AAG GGC     1742
Gln Ile Thr Trp Ala Lys Phe Cys Lys Glu Asn Met Ala Gly Lys Gly
        545                 550                 555

TTC TCC TTC TGG GTC TGG CTA GAC AAT ATC ATC GAC CTT GTG AAA AAG     1790
Phe Ser Phe Trp Val Trp Leu Asp Asn Ile Ile Asp Leu Val Lys Lys
```

```
                560                 565                 570
TAT ATC TTG GCC CTT TGG AAT GAA GGG TAC ATC ATG GGT TTC ATC AGC      1838
Tyr Ile Leu Ala Leu Trp Asn Glu Gly Tyr Ile Met Gly Phe Ile Ser
575                 580                 585                 590

AAG GAG CGG GAG CGG GCC ATC CTA AGC ACA AAG CCC CCG GGC ACC TTC      1886
Lys Glu Arg Glu Arg Ala Ile Leu Ser Thr Lys Pro Pro Gly Thr Phe
                595                 600                 605

CTA CTG CGC TTC AGC GAG AGC AGC AAA GAA GGA GGG GTC ACT TTC ACT      1934
Leu Leu Arg Phe Ser Glu Ser Ser Lys Glu Gly Gly Val Thr Phe Thr
            610                 615                 620

TGG GTG GAA AAG GAC ATC AGT GGC AAG ACC CAG ATC CAG TCT GTA GAG      1982
Trp Val Glu Lys Asp Ile Ser Gly Lys Thr Gln Ile Gln Ser Val Glu
        625                 630                 635

CCA TAC ACC AAG CAG CAG CTG AAC AAC ATG TCA TTT GCT GAA ATC ATC      2030
Pro Tyr Thr Lys Gln Gln Leu Asn Asn Met Ser Phe Ala Glu Ile Ile
    640                 645                 650

ATG GGC TAT AAG ATC ATG GAT GCG ACC AAC ATC CTG GTG TCT CCA CTT      2078
Met Gly Tyr Lys Ile Met Asp Ala Thr Asn Ile Leu Val Ser Pro Leu
655                 660                 665                 670

GTC TAC CTC TAC CCC GAC ATT CCC AAG GAG GAG GCA TTT GGA AAG TAC      2126
Val Tyr Leu Tyr Pro Asp Ile Pro Lys Glu Glu Ala Phe Gly Lys Tyr
                675                 680                 685

TGT AGG CCC GAG AGC CAG GAG CAC CCC GAA GCC GAC CCA GGT AGT GCT      2174
Cys Arg Pro Glu Ser Gln Glu His Pro Glu Ala Asp Pro Gly Ser Ala
            690                 695                 700

GCC CCG TAC CTG AAG ACC AAG TTC ATC TGT GTG ACA CCA ACG ACC TGC      2222
Ala Pro Tyr Leu Lys Thr Lys Phe Ile Cys Val Thr Pro Thr Thr Cys
        705                 710                 715

AGC AAT ACC ATT GAC CTG CCG ATG TCC CCC CGC ACT TTA GAT TCA TTG      2270
Ser Asn Thr Ile Asp Leu Pro Met Ser Pro Arg Thr Leu Asp Ser Leu
    720                 725                 730

ATG CAG TTT GGA AAT AAC GGT GAA GGT GCT GAG CCC TCA GCA GGA GGG      2318
Met Gln Phe Gly Asn Asn Gly Glu Gly Ala Glu Pro Ser Ala Gly Gly
735                 740                 745                 750

CAG TTT GAG TCG CTC ACG TTT GAC ATG GAT CTG ACC TCG GAG TGT GCT      2366
Gln Phe Glu Ser Leu Thr Phe Asp Met Asp Leu Thr Ser Glu Cys Ala
                755                 760                 765

ACC TCC CCC ATG TGAGGAGCTG AAACCAGAAG CTGCAGAGAC GTGACTTGAG          2418
Thr Ser Pro Met
            770

ACACCTGCCC CGTGCTCCAC CCCTAAGCAG CCGAACCCCA TATCGTCTGA AACTCCTAAC    2478

TTTGTGGTTC CAGATTTTTT TTTTTAATTT CCTACTTCTG CTATCTTTGG GCAATCTGGG    2538

CACTTTTTAA AAGAGAGAAA TGAGTGAGTG TGGGTGATAA ACTGTTATGT AAAGAGGAGA    2598

GACCTCTGAG TCTGGGGATG GGGCTGAGAG CAGAAGGGAG GCAAAGGGGA ACACCTCCTG    2658

TCCTGCCCGC CTGCCCTCCT TTTTCAGCAG CTCGGGGGTT GGTTGTTAGA CAAGTGCCTC    2718

CTGGTGCCCA TGGCTACCTG TTGCCCCACT CTGTGAGCTG ATACCCCATT CTGGGAACTC    2778

CTGGCTCTGC ACTTTCAACC TTGCTAATAT CCACATAGAA GCTAGGACTA AGCCCAGGAG    2838

GTTCCTCTTT AAATTAAAAA AAAAAAAAA A                                   2869

(2) INFORMATION FOR SEQ ID NO:12:

(i) SEQUENCE CHARACTERISTICS:
        (A) LENGTH: 770 amino acids
        (B) TYPE: amino acid
        (D) TOPOLOGY: linear (ii) MOLECULE TYPE: protein
```

(xi) SEQUENCE DESCRIPTION: SEQ ID NO:12:

```
Met Ala Gln Trp Asn Gln Leu Gln Gln Leu Asp Thr Arg Tyr Leu Lys
 1               5                  10                  15
Gln Leu His Gln Leu Tyr Ser Asp Thr Phe Pro Met Glu Leu Arg Gln
            20                  25                  30
Phe Leu Ala Pro Trp Ile Glu Ser Gln Asp Trp Ala Tyr Ala Ala Ser
        35                  40                  45
Lys Glu Ser His Ala Thr Leu Val Phe His Asn Leu Leu Gly Glu Ile
    50                  55                  60
Asp Gln Gln Tyr Ser Arg Phe Leu Gln Glu Ser Asn Val Leu Tyr Gln
 65                  70                  75                  80
His Asn Leu Arg Arg Ile Lys Gln Phe Leu Gln Ser Arg Tyr Leu Glu
                85                  90                  95
Lys Pro Met Glu Ile Ala Arg Ile Val Ala Arg Cys Leu Trp Glu Glu
            100                 105                 110
Ser Arg Leu Leu Gln Thr Ala Ala Thr Ala Ala Gln Gln Gly Gly Gln
        115                 120                 125
Ala Asn His Pro Thr Ala Ala Val Val Thr Glu Lys Gln Gln Met Leu
    130                 135                 140
Glu Gln His Leu Gln Asp Val Arg Lys Arg Val Gln Asp Leu Glu Gln
145                 150                 155                 160
Lys Met Lys Val Val Glu Asn Leu Gln Asp Asp Phe Asp Phe Asn Tyr
                165                 170                 175
Lys Thr Leu Lys Ser Gln Gly Asp Met Gln Asp Leu Asn Gly Asn Asn
            180                 185                 190
Gln Ser Val Thr Arg Gln Lys Met Gln Gln Leu Glu Gln Met Leu Thr
        195                 200                 205
Ala Leu Asp Gln Met Arg Arg Ser Ile Val Ser Glu Leu Ala Gly Leu
    210                 215                 220
Leu Ser Ala Met Glu Tyr Val Gln Lys Thr Leu Thr Asp Glu Glu Leu
225                 230                 235                 240
Ala Asp Trp Lys Arg Arg Pro Glu Ile Ala Cys Ile Gly Gly Pro Pro
                245                 250                 255
Asn Ile Cys Leu Asp Arg Leu Glu Asn Trp Ile Thr Ser Leu Ala Glu
            260                 265                 270
Ser Gln Leu Gln Thr Arg Gln Gln Ile Lys Lys Leu Glu Glu Leu Gln
        275                 280                 285
Gln Lys Val Ser Tyr Lys Gly Asp Pro Ile Val Gln His Arg Pro Met
    290                 295                 300
Leu Glu Glu Arg Ile Val Glu Leu Phe Arg Asn Leu Met Lys Ser Ala
305                 310                 315                 320
Phe Val Val Glu Arg Gln Pro Cys Met Pro Met His Pro Asp Arg Pro
                325                 330                 335
Leu Val Ile Lys Thr Gly Val Gln Phe Thr Thr Lys Val Arg Leu Leu
            340                 345                 350
Val Lys Phe Pro Glu Leu Asn Tyr Gln Leu Lys Ile Lys Val Cys Ile
        355                 360                 365
Asp Lys Asp Ser Gly Asp Val Ala Ala Leu Arg Gly Ser Arg Lys Phe
    370                 375                 380
Asn Ile Leu Gly Thr Asn Thr Lys Val Met Asn Met Glu Glu Ser Asn
385                 390                 395                 400
Asn Gly Ser Leu Ser Ala Glu Phe Lys His Leu Thr Leu Arg Glu Gln
                405                 410                 415
```

```
Arg Cys Gly Asn Gly Gly Arg Ala Asn Cys Asp Ala Ser Leu Ile Val
        420                 425                 430

Thr Glu Glu Leu His Leu Ile Thr Phe Glu Thr Glu Val Tyr His Gln
        435                 440                 445

Gly Leu Lys Ile Asp Leu Glu Thr His Ser Leu Pro Val Val Val Ile
        450                 455                 460

Ser Asn Ile Cys Gln Met Pro Asn Ala Trp Ala Ser Ile Leu Trp Tyr
465                 470                 475                 480

Asn Met Leu Thr Asn Asn Pro Lys Asn Val Asn Phe Phe Thr Lys Pro
                485                 490                 495

Pro Ile Gly Thr Trp Asp Gln Val Ala Glu Val Leu Ser Trp Gln Phe
                500                 505                 510

Ser Ser Thr Thr Lys Arg Gly Leu Ser Ile Glu Gln Leu Thr Thr Leu
            515                 520                 525

Ala Glu Lys Leu Leu Gly Pro Gly Val Asn Tyr Ser Gly Cys Gln Ile
        530                 535                 540

Thr Trp Ala Lys Phe Cys Lys Glu Asn Met Ala Gly Lys Gly Phe Ser
545                 550                 555                 560

Phe Trp Val Trp Leu Asp Asn Ile Ile Asp Leu Val Lys Lys Tyr Ile
                565                 570                 575

Leu Ala Leu Trp Asn Glu Gly Tyr Ile Met Gly Phe Ile Ser Lys Glu
                580                 585                 590

Arg Glu Arg Ala Ile Leu Ser Thr Lys Pro Pro Gly Thr Phe Leu Leu
            595                 600                 605

Arg Phe Ser Glu Ser Ser Lys Glu Gly Gly Val Thr Phe Thr Trp Val
        610                 615                 620

Glu Lys Asp Ile Ser Gly Lys Thr Gln Ile Gln Ser Val Glu Pro Tyr
625                 630                 635                 640

Thr Lys Gln Gln Leu Asn Asn Met Ser Phe Ala Glu Ile Ile Met Gly
                645                 650                 655

Tyr Lys Ile Met Asp Ala Thr Asn Ile Leu Val Ser Pro Leu Val Tyr
                660                 665                 670

Leu Tyr Pro Asp Ile Pro Lys Glu Glu Ala Phe Gly Lys Tyr Cys Arg
            675                 680                 685

Pro Glu Ser Gln Glu His Pro Glu Ala Asp Pro Gly Ser Ala Ala Pro
        690                 695                 700

Tyr Leu Lys Thr Lys Phe Ile Cys Val Thr Pro Thr Thr Cys Ser Asn
705                 710                 715                 720

Thr Ile Asp Leu Pro Met Ser Pro Arg Thr Leu Asp Ser Leu Met Gln
                725                 730                 735

Phe Gly Asn Asn Gly Glu Gly Ala Glu Pro Ser Ala Gly Gly Gln Phe
                740                 745                 750

Glu Ser Leu Thr Phe Asp Met Asp Leu Thr Ser Glu Cys Ala Thr Ser
            755                 760                 765

Pro Met
    770

(2) INFORMATION FOR SEQ ID NO:13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA
```

```
    (iii) HYPOTHETICAL: NO (iv) ANTI-SENSE: NO (vi) ORIGINAL SOURCE:
         (A) ORGANISM: Homo sapiens (xi) SEQUENCE DESCRIPTION: SEQ ID NO:13:

AAYACNGARC CNATGGARAT YATT                                           24

(2) INFORMATION FOR SEQ ID NO:14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
         (A) ORGANISM: Homo sapiens (xi) SEQUENCE DESCRIPTION: SEQ ID NO:14:

AAYGTNGAYC ARYTNAAYAT G                                              21

(2) INFORMATION FOR SEQ ID NO:15:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
         (A) ORGANISM: Homo sapiens (xi) SEQUENCE DESCRIPTION: SEQ ID NO:15:

RTCDATRTTN GRGTANAR                                                  18

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
         (A) ORGANISM: Homo sapiens (xi) SEQUENCE DESCRIPTION: SEQ ID NO:16:

GTAYAANTYR AYCAGNGYAA                                                20

(2) INFORMATION FOR SEQ ID NO:17:
```

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:17:

GATCGAGATG TATTTCCCAG AAAAG                                                    25

(2) INFORMATION FOR SEQ ID NO:18:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:18:

Leu Asp Gly Pro Lys Gly Thr Gly Tyr Ile Lys Thr Glu Leu Ile
1               5                   10                  15

(2) INFORMATION FOR SEQ ID NO:19:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:19:

Gly Tyr Ile Lys Thr Glu
1               5

(2) INFORMATION FOR SEQ ID NO:20:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:20:

Lys Val Asn Leu Gln Glu Arg Arg Lys Tyr Leu Lys His Arg

```
1           5              10
```

(2) INFORMATION FOR SEQ ID NO:21:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:21:

```
Glu Pro Gln Tyr Glu Glu Ile Pro Ile Tyr Leu
1               5                   10
```

(2) INFORMATION FOR SEQ ID NO:22:

(i) SEQUENCE CHARACTERISTICS:
        (A) LENGTH: 105 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vii) IMMEDIATE SOURCE:
        (B) CLONE: Src (x) PUBLICATION INFORMATION:
        (A) AUTHORS: Waksman, et al.
        (C) JOURNAL: Nature
        (D) VOLUME: 358
        (F) PAGES: 646-653
        (G) DATE: 1992

(xi) SEQUENCE DESCRIPTION: SEQ ID NO:22:

```
Ala Glu Glu Trp Tyr Phe Gly Lys Ile Thr Arg Arg Glu Ser Glu Arg
1               5                   10                  15

Leu Leu Leu Asn Pro Glu Asn Pro Arg Gly Thr Phe Leu Val Arg Glu
                20                  25                  30

Ser Glu Thr Thr Lys Gly Ala Tyr Cys Leu Ser Val Ser Asp Phe Phe
            35                  40                  45

Asp Asn Ala Lys Gly Leu Asn Val Lys His Tyr Lys Ile Arg Lys Leu
        50                  55                  60

Asp Ser Gly Gly Phe Tyr Ile Thr Ser Arg Thr Gln Phe Ser Ser Leu
65                  70                  75                  80

Gln Gln Leu Val Ala Tyr Tyr Ser Lys His Ala Asp Gly Leu Cys His
                85                  90                  95

Arg Leu Thr Asn Val Cys Pro Thr Ser
            100                 105
```

(2) INFORMATION FOR SEQ ID NO:23:

(i) SEQUENCE CHARACTERISTICS:
        (A) LENGTH: 99 amino acids
        (B) TYPE: amino acid (C) STRANDEDNESS: single
                (D) TOPOLOGY: linear (ii) MOLECULE TYPE: peptide (iii) HYPOTHETICAL: NO (iv) ANTI-SENSE: NO (v) FRAGMENT TYPE: internal (vii) IMMEDIATE SOURCE:
                (B) CLONE: Abl (x) PUBLICATION INFORMATION:
                (A) AUTHORS: Overduin, et al.
                (C) JOURNAL: Proc. Natl. Acad. Sci. U.S.A.
                (D) VOLUME: 89
                (F) PAGES: 11673-11677
                (G) DATE: 1992

(xi) SEQUENCE DESCRIPTION: SEQ ID NO:23:

Glu Lys His Ser Trp Tyr His Gly Pro Val Ser Arg Asn Ala Ala Glu
1               5                   10                  15

Tyr Leu Leu Ser Ser Gly Ile Asn Gly Ser Phe Leu Val Arg Glu Ser
                20                  25                  30

Asp Arg Arg Pro Gly Gln Arg Ser Ile Ser Leu Arg Tyr Glu Glu Gly
            35                  40                  45

Arg Val Tyr His Tyr Arg Ile Asn Thr Ala Ser Asp Gly Lys Leu Tyr
    50                  55                  60

Val Ser Ser Glu Ser Arg Phe Asn Thr Leu Ala Glu Leu Val His His
65                  70                  75                  80

His Ser Thr Val Ala Asp Gly Leu Ile Thr Thr Leu His Tyr Pro Ala
                85                  90                  95

Pro Lys Arg (2) INFORMATION FOR SEQ ID NO:24:

(i) SEQUENCE CHARACTERISTICS:
                (A) LENGTH: 102 amino acids
                (B) TYPE: amino acid
                (C) STRANDEDNESS: single
                (D) TOPOLOGY: linear (ii) MOLECULE TYPE: peptide (iii) HYPOTHETICAL: NO (iv) ANTI-SENSE: NO (v) FRAGMENT TYPE: internal (vii) IMMEDIATE SOURCE:
                (B) CLONE: Lck (x) PUBLICATION INFORMATION:
                (A) AUTHORS: Eck, et al.
                (C) JOURNAL: Nature
                (D) VOLUME: 362
                (F) PAGES: 87-91
                (G) DATE: 1993

(xi) SEQUENCE DESCRIPTION: SEQ ID NO:24:

Trp Phe Phe Lys Asn Leu Ser Arg Lys Asp Ala Glu Arg Gln Leu Leu
1               5                   10                  15

Ala Pro Gly Asn Thr His Gly Ser Phe Leu Ile Arg Glu Ser Glu Ser
                20                  25                  30

Thr Ala Gly Ser Phe Ser Leu Ser Val Arg Asp Asp Phe Asp Gln Asn
            35                  40                  45

-continued

```
Gln Gly Glu Val Val Lys His Tyr Lys Ile Arg Asn Leu Asp Asn Gly
            50              55                  60

Gly Phe Tyr Ile Ser Pro Arg Ile Thr Phe Pro Gly Leu His Asp Leu
 65              70                  75                      80

Val Arg His Tyr Thr Asn Ala Ser Asp Gly Leu Cys Thr Arg Leu Ser
                 85                  90                  95

Arg Pro Cys Gln Thr Gln
                100
```

(2) INFORMATION FOR SEQ ID NO:25:

(i) SEQUENCE CHARACTERISTICS:
      (A) LENGTH: 99 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (v) FRAGMENT TYPE: internal (vii) IMMEDIATE SOURCE:
       (B) CLONE: p85[alpha]N (xi) SEQUENCE DESCRIPTION: SEQ ID NO:25:

```
Gln Asp Ala Glu Trp Tyr Trp Gly Asp Ile Ser Arg Glu Glu Val Asn
 1               5                  10                  15

Glu Lys Leu Arg Asp Thr Ala Asp Gly Thr Phe Leu Val Arg Asp Ala
             20                  25                  30

Ser Thr Lys Met His Gly Asp Tyr Thr Leu Thr Leu Arg Lys Gly Gly
         35                  40                  45

Asn Asn Lys Leu Ile Lys Ile Phe His Arg Asp Gly Lys Tyr Gly Phe
     50                  55                  60

Ser Asp Pro Leu Thr Phe Asn Ser Val Val Glu Leu Ile Asn His Tyr
 65              70                  75                      80

Arg His Glu Ser Leu Ala Gln Tyr Asn Pro Lys Leu Asp Val Lys Leu
                 85                  90                  95

Leu Tyr Pro
```